US011780885B2

(12) United States Patent
Dowd et al.

(10) Patent No.: US 11,780,885 B2
(45) Date of Patent: Oct. 10, 2023

(54) ZIKA VIRAL ANTIGEN CONSTRUCTS

(71) Applicants: GLAXOSMITHKLINE BIOLOGICALS SA, Rixensart (BE); THE UNITED STATES OF AMERICA, AS REPRESENTED BY THE SECRETARY, DEPARTMENT OF HEALTH AND HUMAN SERVICES, Bethesda, MD (US)

(72) Inventors: Kimberly Dowd, Rockville, MD (US); Barney S. Graham, Rockville, MD (US); Sung-Youl Ko, Rockville, MD (US); Wing-Pui Kong, Rockville, MD (US); John Mascola, Rockville, MD (US); Theodore Pierson, Rockville, MD (US); Mayuri Sharma, Cambridge, MA (US); Dong Yu, Rockville, MD (US)

(73) Assignees: GLAXOSMITHKLINE BIOLOGICALS SA, Rixensart (BE); THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 189 days.

(21) Appl. No.: 16/461,503

(22) PCT Filed: Nov. 15, 2017

(86) PCT No.: PCT/EP2017/079343

§ 371 (c)(1),
(2) Date: May 16, 2019

(87) PCT Pub. No.: WO2018/091540

PCT Pub. Date: May 24, 2018

(65) Prior Publication Data

US 2019/0345205 A1 Nov. 14, 2019

Related U.S. Application Data

(60) Provisional application No. 62/568,559, filed on Oct. 5, 2017, provisional application No. 62/485,090, filed (Continued)

(51) Int. Cl.
*C07K 14/005* (2006.01)
*A61K 39/12* (2006.01)

(Continued)

(52) U.S. Cl.
CPC ............ *C07K 14/005* (2013.01); *A61K 39/12* (2013.01); *C12N 7/00* (2013.01); *A61K 2039/53* (2013.01);

(Continued)

(58) Field of Classification Search
None
See application file for complete search history.

(56) References Cited

U.S. PATENT DOCUMENTS

| | | | |
|---|---|---|---|
| 10,653,767 | B2 | 5/2020 | Ciaramella et al. |
| 10,675,342 | B2 | 6/2020 | Ciaramella et al. |

(Continued)

FOREIGN PATENT DOCUMENTS

| | | | |
|---|---|---|---|
| WO | WO 2013/006837 | A1 | 1/2013 |
| WO | WO 2017/015463 | A2 | 1/2017 |

(Continued)

OTHER PUBLICATIONS

Brazzoli et al. Induction of Broad-Based Immunity and Protective Efficacy by Self-amplifying mRNA Vaccines Encoding Influenza Virus Hemagglutinin. Journal of Virology. vol. 90, No. 1, p. 332-344. (Year: 2016).*

(Continued)

*Primary Examiner* — Michelle S Horning
(74) *Attorney, Agent, or Firm* — Birch, Stewart, Kolasch & Birch, LLP

(57) ABSTRACT

Compounds useful as components of immunogenic compositions for the induction of an immunogenic response in a (Continued)

Figure 1:
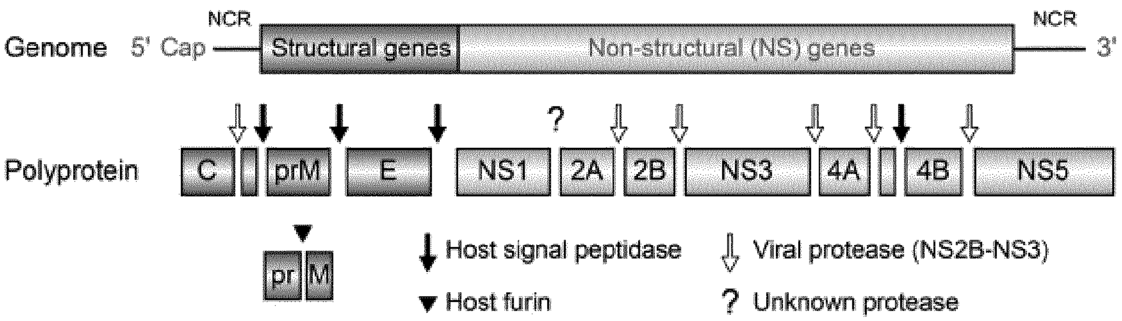

subject against viral infection, methods for their use in treatment, and processes for their manufacture are provided herein. The compounds comprise a nucleic acid construct comprising a sequence which encodes a Zika virus antigen.

19 Claims, 17 Drawing Sheets

Specification includes a Sequence Listing.

Related U.S. Application Data on Apr. 13, 2017, provisional application No. 62/423,398, filed on Nov. 17, 2016.

(51) Int. Cl.
*C12N 7/00* (2006.01)
*A61K 39/00* (2006.01)

(52) U.S. Cl.
CPC .............. *C12N 2770/24122* (2013.01); *C12N 2770/24134* (2013.01)

(56) References Cited

U.S. PATENT DOCUMENTS

2003/0022849 A1* 1/2003 Chang ..................... A61P 31/12 435/339
2019/0099481 A1 4/2019 Ciaramella et al.
2019/0144506 A1* 5/2019 Barouch ................. A61P 31/14 424/139.1

FOREIGN PATENT DOCUMENTS

WO WO 2017-070624 A1 4/2017
WO WO 2017/208191 A1 12/2017
WO WO 2019/055807 A1 3/2019
WO WO 02/081754 A1 10/2022

OTHER PUBLICATIONS

Bogers et al. Potent immune responses in rhesus macaques induced by nonviral delivery of a self-amplifying RNA vaccine expressing HIV type 1 envelope with a cationic nanoemulsion. J Infect Dis Mar. 15, 2015;211(6):947-55. (Year: 2015).*

Chang GJ, Hunt AR, Holmes DA, Springfield T, Chiueh TS, Roehrig JT, Gubler DJ. Enhancing biosynthesis and secretion of premembrane and envelope proteins by the chimeric plasmid of dengue virus type 2 and Japanese encephalitis virus. Virology. Feb. 1, 2003;306(1):170-80. (Year: 2003).*

GenBank: AQS26799.1 (2017) (Year: 2017).*

Chahal et al., "An RNA nanoparticle vaccine against Zika virus elicits antibody and CD8+ T cell responses in a mouse model," Scientific Reports (2017), 7:252, pp. 1-9.

Dowd et al., "Rapid development of a DNA vaccine for Zika virus," Science (2016), vol. 354, Issue 6309, pp. 237-240.

International Search Report dated Feb. 2, 2018, in PCT/EP2017/079343.

Muthumani et al., "In vivo protection against ZIKV infection and pathogensis through passive antibody transfer and active immunisation with a prMEnv DNA vaccine," Npj Vaccines (2016), vol. 1, 16021, pp. 1-11.

Richner et al, "Modified mRNA Vaccines Protect against Zika Virus Infection," Cell (2017), vol. 168, pp. 1114-1125.

Written Opinion dated May 24, 2018, in PCT/EP2017/079343.

European Search Report dated Oct. 24, 2022, in European Patent Application No. 21216477.6.

Extended European Search Report dated Jul. 5, 2022, in European Patent Application No. 21216477.6.

* cited by examiner

FIG.3A

```
                ◄──────────────────────────────────Capsid(C)────────────────
Uganda          MKNPKEEIRRIRIVNMLKRGVARVNPLGGLKRLPAGLLLGHGPIRMVLAILAFLRFTAIK  60
Micronesia      MKNPKEEIRRIRIVNMLKRGVARVSPFGGLKRLPAGLLLGHGPIRMVLAILAFLRFTAIK  60
Natal           MKNPKKKSGGFRIVNMLKRGVARVSPFGGLKRLPAGLLLGHGPIRMVLAILAFLRFTAIK  60
Salvador        MKNPKKKSGGFRIVNMLKRGVARVSPFGGLKRLPAGLLLGHGPIRMVLAILAFLRFTAIK  60
KU365777        MKNPKKKSGGFRIVNMLKRGVARVSPFGGLKRLPAGLLLGHGPIRMVLAILAFLRFTAIK  60
KU365778        MKNPKKKSGGFRIVNMLKRGVARVSPFGGLKRLPAGLLLGHGPIRMVLAILAFLRFTAIK  60
KU365779        MKNPKKKSGGFRIVNMLKRGVARVSPFGGLKRLPAGLLLGHGPIRMVLAILAFLRFTAIK  60
KU365780        MKNPKKKSGGFRIVNMLKRGVARVSPFGGLKRLPAGLLLGHGPIRMVLAILAFLRFTAIK  60
French          MKNPKKKSGGFRIVNMLKRGVARVSPFGGLKRLPAGLLLGHGPIRMVLAILAFLRFTAIK  60
Sao             MKNPKKKSGGFRIVNMLKRGVARVSPFGGLKRLPAGLLLGHGPIRMVLAILAFLRFTAIK  60
                *****::   :*************.*:*********************************

                ────────────────Capsid(C) ─────────────────►◄─prM Signal Sequence
Uganda          PSLGLINRWGSVGKKEAMEIIKKFKKDLAAMLRIINARKERKRRGADTSIGIIGLLLTTA  120
Micronesia      PSLGLINRWGSVGKKEAMEIIKKFKKDLAAMLRIINARKEKKRRGTDTSVGIVGLLLTTA  120
Natal           PSLGLINRWGSVGKKEAMEIIKKFKKDLAAMLRIINARKEKKRRGADTSVGIVGLLLTTA  120
Salvador        PSLGLINRWGSVGKKEAMEIIKKFKKDLAAMLRIINARKEKKRRGADTSVGIVGLLLTTA  120
KU365777        PSLGLINRWGSVGKKEAMEIIKKFKKDLAAMLRIINARKEKKRRGADTSVGIVGLLLTTA  120
KU365778        PSLGLINRWGSVGKKEAMEIIKKFKKDLAAMLRIINARKEKKRRGADTSVGIVGLLLTTA  120
KU365779        PSLGLINRWGSVGKKEAMEIIKKFKKDLAAMLRIINARKEKKRRGADTSVGIVGLLLTTA  120
KU365780        PSLGLINRWGSVGKKEAMEIIKKFKKDLAAMLRIINARKEKKRRGADTSVGIVGLLLTTA  120
French          PSLGLINRWGSVGKKEAMEIIKKFKKDLAAMLRIINARKEKKRRGADTSVGIVGLLLTTA  120
Sao             PSLGLINRWGSVGKKEAMEIIKKFKKDLAAMLRIINARKEKKRRGADTSVGIVGLLLTTA  120
                ****************************************:****:***:**:*******

                ─►◄─────────────────────────────Pre-Membrane(prM)───────────
Uganda          MAAEITRRGSAYYMYLDRSDAGKAISFATTLGVNKCHVQIMDLGHMCDATMSYECPMLDE  180
Micronesia      MAVEVTRRGSAYYMYLDRSDAGEAISFPTTLGMNKCYIQIMDLGHMCDATMSYECPMLDE  180
Natal           MAAEVTRRGSAYYMYLDRNDAGEAISFPTTLGMNKCYIQIMDLGHMCDATMSYECPMLDE  180
Salvador        MAAEVTRRGSAYYMYLDRNDAGEAISFPTTLGMNKCYIQIMDLGHMCDATMSYECPMLDE  180
KU365777        MAAEVTRRGSAYYMYLDRNDAGEAISFPTTLGMNKCYIQIMDLGHMCDATMSYECPMLDE  180
KU365778        MAAEVTRRGSAYYMYLDRNDAGEAISFPTTLGMNKCYIQIMDLGHMCDATMSYECPMLDE  180
KU365779        MAAEVTRRGSAYYMYLDRNDAGEAISFPTTLGMNKCYIQIMDLGHMCDATMSYECPMLDE  180
KU365780        MAAEVTRRGSAYYMYLDRNDAGEAISFPTTLGMNKCYIQIMDLGHMCDATMSYECPMLDE  180
French          MAAEVTRRGSAYYMYLDRNDAGEAISFPTTLGMNKCYIQIMDLGHMCDATMSYECPMLDE  180
Sao             MAAEVTRRGSAYYMYLDRNDAGEAISFPTTLGMNKCYIQIMDLGHMCDATMSYECPMLDE  180
                **.*:*************.***:**** ****:***::**********************

                ───────────────────────────────────────────────(prM)────────
Uganda          GVEPDDVDCWCNTTSTWVVYGTCHHKKGEARRSRRAVTLPSHSTRKLQTRSQTWLESREY  240
Micronesia      GVEPDDVDCWCNTTSTWVVYGTCHHKKGEARRSRRAVTLPSHSTRKLQTRSQTWLESREY  240
Natal           GVEPDDVDCWCNTTSTWVVYGTCHHKKGEARRSRRAVTLPSHSTRKLQTRSQTWLESREY  240
Salvador        GVEPDDVDCWCNTTSTWVVYGTCHHKKGEARRSRRAVTLPSHSTRKLQTRSQTWLESREY  240
KU365777        GVEPDDVDCWCNTTSTWVVYGTCHHKKGEARRSRRAVTLPSHSTRKLQTRSQTWLESREY  240
KU365778        GVEPDDVDCWCNTTSTWVVYGTCHHKKGEARRSRRAVTLPSHSTRKLQTRSQTWLESREY  240
KU365779        GVEPDDVDCWCNTTSTWVVYGTCHHKKGEARRSRRAVTLPSHSTRKLQTRSQTWLESREY  240
KU365780        GVEPDDVDCWCNTTSTWVVYGTCHHKKGEARRSRRAVTLPSHSTRKLQTRSQTWLESREY  240
French          GVEPDDVDCWCNTTSTWVVYGTCHHKKGEARRSRRAVTLPSHSTRKLQTRSQTWLESREY  240
Sao             GVEPDDVDCWCNTTSTWVVYGTCHHKKGEARRSRRAVTLPSHSTRKLQTRSQTWLESREY  240
                ************************************************************
```

FIG.3B

```
               -prM-------->◄-Signal Sequence------------------->◄-Envelope(E)
Uganda         TKHLIKVENWIFRNPGFALVAVAIAWLLGSSTSQKVIYLVMILLIAPAYSIRCIGVSNRD  300
Micronesia     TKHLIRVENWIFRNPGFALAAAAIAWLLGSSTSQKVIYLVMILLIAPAYSIRCIGVSNRD  300
Natal          TKHLIRVENWIFRNPGFALAAAAIAWLLGSSTSQKVIYLVMILLIAPAYSIRCIGVSNRD  300
Salvador       TKHLIRVENWIFRNPGFALAAAAIAWLLGSSTSQKVIYLVMILLIAPAYSIRCIGVSNRD  300
KU365777       TKHLIRVENWIFRNPGFALAAAAIAWLLGSSTSQKVIYLVMILLIAPAYSIRCIGVSNRD  300
KU365778       TKHLIRVENWIFRNPGFALAAAAIAWLLGSSTSQKVIYLVMILLIAPAYSIRCIGVSNRD  300
KU365779       TKHLIRVENWIFRNPGFALAAAAIAWLLGSSTSQKVIYLVMILLIAPAYSIRCIGVSNRD  300
KU365780       TKHLIRVENWIFRNPGFALAAAAIAWLLGSSTSQKVIYLVMILLIAPAYSIRCIGVSNRD  300
French         TKHLIRVENWIFRNPGFALAAAAIAWLLGSSTSQKVIYLVMILLIAPAYSIRCIGVSNRD  300
Sao            TKHLIRVENWIFRNPGFALAAAAIAWLLGSSTSQKVIYLVMILLIAPAYSIRCIGVSNRD  300
               *****:*************.*.**************************************

               -----------------------------------------------(E)----------
Uganda         FVEGMSGGTWVDVVLEHGGCVTVMAQDKPTVDIELVTTTVSNMAEVRSYCYEASISDMAS  360
Micronesia     FVEGMSGGTWVDVVLEHGGCVTVMAQDKPAVDIELVTTTVSNMAEVRSYCYEASISDMAS  360
Natal          FVEGMSGGTWVDVVLEHGGCVTVMAQDKPTVDIELVTTTVSNMAEVRSYCYEASISDMAS  360
Salvador       FVEGMSGGTWVDVVLEHGGCVTVMAQDKPTVDIELVTTTVSNMAEVRSYCYEASISDMAS  360
KU365777       FVEGMSGGTWVDVVLEHGGCVTVMAQDKPTVDIELVTTTVSNMAEVRSYCYEASISDMAS  360
KU365778       FVEGMSGGTWVDVVLEHGGCVTVMAQDKPTVDIELVTTTVSNMAEVRSYCYEASISDMAS  360
KU365779       FVEGMSGGTWVDVVLEHGGCVTVMAQDKPTVDIELVTTTVSNMAEVRSYCYEASISDMAS  360
KU365780       FVEGMSGGTWVDVVLEHGGCVTVMAQDKPTVDIELVTTTVSNMAEVRSYCYEASISDMAS  360
French         FVEGMSGGTWVDVVLEHGGCVTVMAQDKPTVDIELVTTTVSNMAEVRSYCYEASISDMAS  360
Sao            FVEGMSGGTWVDIVLEHGGCVTVMAQDKPTVDIELVTTTVSNMAEVRSYCYEASISDMAS  360
               ************:***************:*******************************

               -----------------------------------------------(E)----------
Uganda         DSRCPTQGEAYLDKQSDTQYVCKRTLVDRGWGNGCGLFGKGSLVTCAKFTCSKKMTGKSI  420
Micronesia     DSRCPTQGEAYLDKQSDTQYVCKRTLVDRGWGNGCGLFGKGSLVTCAKFACSKKMTGKSI  420
Natal          DSRCPTQGEAYLDKQSDTQYVCKRTLVDRGWGNGCGLFGKGSLVTCAKFACSKKMTGKSI  420
Salvador       DSRCPTQGEAYLDKQSDTQYVCKRTLVDRGWGNGCGLFGKGSLVTCAKFACSKKMTGKSI  420
KU365777       DSRCPTQGEAYLDKQSDTQYVCKRTLVDRGWGNGCGLFGKGSLVTCAKFACSKKMTGKSI  420
KU365778       DSRCPTQGEAYLDKQSDTQYVCKRTLVDRGWGNGCGLFGKGSLVTCAKFACSKKMTGKSI  420
KU365779       DSRCPTQGEAYLDKQSDTQYVCKRTLVDRGWGNGCGLFGKGSLVTCAKFACSKKMTGKSI  420
KU365780       DSRCPTQGEAYLDKQSDTQYVCKRTLVDRGWGNGCGLFGKGSLVTCAKFACSKKMTGKSI  420
French         DSRCPTQGEAYLDKQSDTQYVCKRTLVDRGWGNGCGLFGKGSLVTCAKFACSKKMTGKSI  420
Sao            DSRCPTQGEAYLDKQSDTQYVCKRTLVDRGWGNGCGLFGKGSLVTCAKFACSKKMTGKSI  420
               *************************************************:**********

               -----------------------------------------------(E)----------
Uganda         QPENLEYRIMLSVHGSQHSGMI----GYETDEDRAKVEVTPNSPRAEATLGGFGSLGLDC  476
Micronesia     QPENLEYRIMLSVHGSQHSGMIVNDTGHETDENRAKVEITPNSPRAEATLGGFGSLGLDC  480
Natal          QPENLEYRIMLSVHGSQHSGMIVNDTGHETDENRAKVEITPNSPRAEATLGGFGSLGLDC  480
Salvador       QPENLEYRIMLSVHGSQHSGMIVNDTGHETDENRAKVEITPNSPRAEATLGGFGSLGLDC  480
KU365777       QPENLEYRIMLSVHGSQHSGMIVNDTGHETDENRAKVEITPNSPRAEATLGGFGSLGLDC  480
KU365778       QPENLEYRIMLSVHGSQHSGMIVNDTGHETDENRAKVEITPNSPRAEATLGGFGSLGLDC  480
KU365779       QPENLEYRIMLSVHGSQHSGMIVNDTGHETDENRAKVEITPNSPRAEATLGGFGSLGLDC  480
KU365780       QPENLEYRIMLSVHGSQHSGMIVNDTGHETDENRAKVEITPNSPRAEATLGGFGSLGLDC  480
French         QPENLEYRIMLSVHGSQHSGMIVNDTGHETDENRAKVEITPNSPRAEATLGGFGSLGLDC  480
Sao            QPENLEYRIMLSVHGSQHSGMIVNDTGHETDENRAKVEITPNSPRAEATLGGFGSLGLDC  480
               **********************    *:****:*****:*********************
```

FIG.3C

```
                                                                     (E)
Uganda        EPRTGLDFSDLYYLTMNNKHWLVHKEWFHDIPLPWHAGADTGTPHWNNKEALVEFKDAHA   536
Micronesia    EPRTGLDFSDLYYLTMNNKHWLVHKEWFHDIPLPWHAGADTGTPHWNNKEALVEFKDAHA   540
Natal         EPRTGLDFSDLYYLTMNNKHWLVHKEWFHDIPLPWHAGADTGTPHWNNKEALVEFKDAHA   540
Salvador      EPRTGLDFSDLYYLTMNNKHWLVHKEWFHDIPLPWHAGADTGTPHWNNKEALVEFKDAHA   540
KU365777      EPRTGLDFSDLYYLTMNNKHWLVHKEWFHDIPLPWHAGADTGTPHWNNKEALVEFKDAHA   540
KU365778      EPRTGLDFSDLYYLTMNNKHWLVHKEWFHDIPLPWHAGADTGTPHWNNKEALVEFKDAHA   540
KU365779      EPRTGLDFSDLYYLTMNNKHWLVHKEWFHDIPLPWHAGADTGTPHWNNKEALVEFKDAHA   540
KU365780      EPRTGLDFSDLYYLTMNNKHWLVHKEWFHDIPLPWHAGADTGTPHWNNKEALVEFKDAHA   540
French        EPRTGLDFSDLYYLTMNNKHWLVHKEWFHDIPLPWHAGADTGTPHWNNKEALVEFKDAHA   540
Sao           EPRTGLDFSDLYYLTMNNKHWLVHKEWFHDIPLPWHAGADTGTPHWNNKEALVEFKDAHA   540
              ************************************************************

                                                                     (E)
Uganda        KRQTVVVLGSQEGAVHTALAGALEAEMDGAKGRLFSGHLKCRLKMDKLRLKGVSYSLCTA   596
Micronesia    KRQTVVVLGSQEGAVHTALAGALEAEMDGAKGRLSSGHLKCRLKMDKLRLKGVSYSLCTA   600
Natal         KRQTVVVLGSQEGAVHTALAGALEAEMDGAKGRLSSGHLKCRLKMDKLRLKGVSYSLCTA   600
Salvador      KRQTVVVLGSQEGAVHTALAGALEAEMDGAKGRLSSGHLKCRLKMDKLRLKGVSYSLCTA   600
KU365777      KRQTVVVLGSQEGAVHTALAGALEAEMDGAKGRLSSGHLKCRLKMDKLRLKGVSYSLCTA   600
KU365778      KRQTVVVLGSQEGAVHTALAGALEAEMDGAKGRLSSGHLKCRLKMDKLRLKGVSYSLCTA   600
KU365779      KRQTVVVLGSQEGAVHTALAGALEAEMDGAKGRLSSGHLKCRLKMDKLRLKGVSYSLCTA   600
KU365780      KRQTVVVLGSQEGAVHTALAGALEAEMDGAKGRLSSGHLKCRLKMDKLRLKGVSYSLCTA   600
French        KRQTVVVLGSQEGAVHTALAGALEAEMDGAKGRLSSGHLKCRLKMDKLRLKGVSYSLCTA   600
Sao           KRQTVVVLGSQEGAVHTALAGALEAEMDGAKGRLSSGHLKCRLKMDKLRLKGVSYSLCTA   600
              ********************************** *************************

                                                                     (E)
Uganda        AFTFTKVPAETLHGTVTVEVQYAGTDGPCKIPVQMAVDMQTLTPVGRLITANPVITESTE   656
Micronesia    AFTFTKIPAETLHGTVTVEVQYAGTDGPCKVPAQMAVDMQTLTPVGRLITANPVITESTE   660
Natal         AFTFTKIPAETLHGTVTVEVQYAGTDGPCKVPAQMAVDMQTLTPVGRLITANPVITESTE   660
Salvador      AFTFTKIPAETLHGTVTVEVQYAGTDGPCKVPAQMAVDMQTLTPVGRLITANPVITESTE   660
KU365777      AFTFTKIPAETLHGTVTVEVQYAGTDGPCKVPAQMAVDMQTLTPVGRLITANPVITESTE   660
KU365778      AFTFTKIPAETLHGTVTVEVQYAGTDGPCKVPAQMAVDMQTLTPVGRLITANPVITESTE   660
KU365779      AFTFTKIPAETLHGTVTVEVQYAGTDGPCKVPAQMAVDMQTLTPVGRLITANPVITESTE   660
KU365780      AFTFTKIPAETLHGTVTVEVQYAGTDGPCKVPAQMAVDMQTLTPVGRLITANPVITESTE   660
French        AFTFTKIPAETLHGTVTVEVQYAGTDGPCKVPAQMAVDMQTLTPVGRLITANPVITESTE   660
Sao           AFTFTKIPAETLHGTVTVEVQYAGTDGPCKVPAQMAVDMQTLTPVGRLITANPVITESTE   660
              ******:************************:*.**************************

                                                                     (E)
Uganda        NSKMMLELDPPFGDSYIVIGVGDKKITHHWHRSGSTIGKAFEATVRGAKRMAVLGDTAWD   716
Micronesia    NSKMMLELDPPFGDSYIVIGVGEKKITHHWHRSGSTIGKAFEATVRGAKRMAVLGDTAWD   720
Natal         NSKMMLELDPPFGDSYIVIGVGEKKITHHWHRSGSTIGKAFEATVRGAKRMAVLGDTAWD   720
Salvador      NSKMMLELDPPFGDSYIVIGVGEKKITHHWHRSGSTIGKAFEATVRGAKRMAVLGDTAWD   720
KU365777      NSKMMLELDPPFGDSYIVIGVGEKKITHHWHRSGSTIGKAFEATVRGAKRMAVLGDTAWD   720
KU365778      NSKMMLELDPPFGDSYIVIGVGEKKITHHWHRSGSTIGKAFEATVRGAKRMAVLGDTAWD   720
KU365779      NSKMMLELDPPFGDSYIVIGVGEKKITHHWHRSGSTIGKAFEATVRGAKRMAVLGDTAWD   720
KU365780      NSKMMLELDPPFGDSYIVIGVGEKKITHHWHRSGSTIGKAFEATVRGAKRMAVLGDTAWD   720
French        NSKMMLELDPPFGDSYIVIGVGEKKITHHWHRSGSTIGKAFEATVRGAKRMAVLGDTAWD   720
Sao           NSKMMLELDPPFGDSYIVIGVGEKKITHHWHRSGSTIGKAFEATVRGAKRMAVLGDTAWD   720
              **********************:*************************************
```

*FIG.3D*

```
                ──────────────────────────────────────────────────(E)───────
Uganda          FGSVGGVFNSLGKGIHQIFGAAFKSLFGGMSWFSQILIGTLLVWLGLNTKNGSISLTCLA   776
Micronesia      FGSVGGALNSLGKGIHQIFGAAFKSLFGGMSWFSQILIGTLLVWLGLNTKNGSISLTCLA   780
Natal           FGSVGGALNSLGKGIHQIFGAAFKSLFGGMSWFSQILIGTLLMWLGLNTKNGSISLMCLA   780
Salvador        FGSVGGALNSLGKGIHQIFGAAFKSLFGGMSWFSQILIGTLLMWLGLNTKNGSISLMCLA   780
KU365777        FGSVGGALNSLGKGIHQIFGAAFKSLFGGMSWFSQILIGTLLMWLGLNTKNGSISLMCLA   780
KU365778        FGSVGGALNSLGKGIHQIFGAAFKSLFGGMSWFSQILIGTLLMWLGLNTKNGSISLMCLA   780
KU365779        FGSVGGALNSLGKGIHQIFGAAFKSLFGGMSWFSQILIGTLLMWLGLNTKNGSISLMCLA   780
KU365780        FGSVGGALNSLGKGIHQIFGAAFKSLFGGMSWFSQILIGTLLMWLGLNTKNGSISLMCLA   780
French          FGSVGGALNSLGKGIHQIFGAAFKSLFGGMSWFSQILIGTLLMWLGLNTKNGSISLMCLA   780
Sao             FGSVGGALNSLGKGIHQIFGAAFKSLFGGMSWFSQILIGTLLMWLGLNTKNGSISLMCLA   780
                ******.:**********************************:************* ***

                ───(E)──────>
Uganda          LGGVMIFLSTAVSAD     791
Micronesia      LGGVLIFLSTAVSAD     795
Natal           LGGVLIFLSTAVSAD     795
Salvador        LGGVLIFLSTAVSAD     795
KU365777        LGGVLIFLSTAVSAD     795
KU365778        LGGVLIFLSTAVSAD     795
KU365779        LGGVLIFLSTAVSAD     795
KU365780        LGGVLIFLSTAVSAD     795
French          LGGVLIFLSTAVSAD     795
Sao             LGGVLIFLSTAVSAD     795
                ****:**********
```

*FIG.4A*

```
                ◄──────────────────────────────Capsid(C)──────────
Natal           MKNPKKKSGGFRIVNMLKRGVARVSPFGGLKRLPAGLLLGHGPIRMVLAILAFLRFTAIK
Salvador        MKNPKKKSGGFRIVNMLKRGVARVSPFGGLKRLPAGLLLGHGPIRMVLAILAFLRFTAIK
KU365777        MKNPKKKSGGFRIVNMLKRGVARVSPFGGLKRLPAGLLLGHGPIRMVLAILAFLRFTAIK
KU365778        MKNPKKKSGGFRIVNMLKRGVARVSPFGGLKRLPAGLLLGHGPIRMVLAILAFLRFTAIK
KU365779        MKNPKKKSGGFRIVNMLKRGVARVSPFGGLKRLPAGLLLGHGPIRMVLAILAFLRFTAIK
KU365780        MKNPKKKSGGFRIVNMLKRGVARVSPFGGLKRLPAGLLLGHGPIRMVLAILAFLRFTAIK
Sao             MKNPKKKSGGFRIVNMLKRGVARVSPFGGLKRLPAGLLLGHGPIRMVLAILAFLRFTAIK
                ************************************************************

                ────────────────Capsid(C)      ────────────────►◄─prM     Signal
Sequence
Natal           PSLGLINRWGSVGKKEAMEIIKKFKKDLAAMLRIINARKEKKRRGADTSVGIVGLLLTTA
Salvador        PSLGLINRWGSVGKKEAMEIIKKFKKDLAAMLRIINARKEKKRRGADTSVGIVGLLLTTA
KU365777        PSLGLINRWGSVGKKEAMEIIKKFKKDLAAMLRIINARKEKKRRGADTSVGIVGLLLTTA
KU365778        PSLGLINRWGSVGKKEAMEIIKKFKKDLAAMLRIINARKEKKRRGADTSVGIVGLLLTTA
KU365779        PSLGLINRWGSVGKKEAMEIIKKFKKDLAAMLRIINARKEKKRRGADTSVGIVGLLLTTA
KU365780        PSLGLINRWGSVGKKEAMEIIKKFKKDLAAMLRIINARKEKKRRGADTSVGIVGLLLTTA
Sao             PSLGLINRWGSVGKKEAMEIIKKFKKDLAAMLRIINARKEKKRRGADTSVGIVGLLLTTA
                ************************************************************

                ─►◄───────────────────────────Pre-Membrane(prM)────────
Natal           MAAEVTRRGSAYYMYLDRNDAGEAISFPTTLGMNKCYIQIMDLGHMCDATMSYECPMLDE
Salvador        MAAEVTRRGSAYYMYLDRNDAGEAISFPTTLGMNKCYIQIMDLGHMCDATMSYECPMLDE
KU365777        MAAEVTRRGSAYYMYLDRNDAGEAISFPTTLGMNKCYIQIMDLGHMCDATMSYECPMLDE
KU365778        MAAEVTRRGSAYYMYLDRNDAGEAISFPTTLGMNKCYIQIMDLGHMCDATMSYECPMLDE
KU365779        MAAEVTRRGSAYYMYLDRNDAGEAISFPTTLGMNKCYIQIMDLGHMCDATMSYECPMLDE
KU365780        MAAEVTRRGSAYYMYLDRNDAGEAISFPTTLGMNKCYIQIMDLGHMCDATMSYECPMLDE
Sao             MAAEVTRRGSAYYMYLDRNDAGEAISFPTTLGMNKCYIQIMDLGHMCDATMSYECPMLDE
                ************************************************************

                ─────────────────────────────────────────────(prM)──────
Natal           GVEPDDVDCWCNTTSTWVVYGTCHHKKGEARRSRRAVTLPSHSTRKLQTRSQTWLESREY
Salvador        GVEPDDVDCWCNTTSTWVVYGTCHHKKGEARRSRRAVTLPSHSTRKLQTRSQTWLESREY
KU365777        GVEPDDVDCWCNTTSTWVVYGTCHHKKGEARRSRRAVTLPSHSTRKLQTRSQTWLESREY
KU365778        GVEPDDVDCWCNTTSTWVVYGTCHHKKGEARRSRRAVTLPSHSTRKLQTRSQTWLESREY
KU365779        GVEPDDVDCWCNTTSTWVVYGTCHHKKGEARRSRRAVTLPSHSTRKLQTRSQTWLESREY
KU365780        GVEPDDVDCWCNTTSTWVVYGTCHHKKGEARRSRRAVTLPSHSTRKLQTRSQTWLESREY
Sao             GVEPDDVDCWCNTTSTWVVYGTCHHKKGEARRSRRAVTLPSHSTRKLQTRSQTWLESREY
                ************************************************************

                ─prM────────►◄─SignalSequence──────────────────►◄─Envelope(E)
Natal           TKHLIRVENWIFRNPGFALAAAAIAWLLGSSTSQKVIYLVMILLIAPAYSIRCIGVSNRD
Salvador        TKHLIRVENWIFRNPGFALAAAAIAWLLGSSTSQKVIYLVMILLIAPAYSIRCIGVSNRD
KU365777        TKHLIRVENWIFRNPGFALAAAAIAWLLGSSTSQKVIYLVMILLIAPAYSIRCIGVSNRD
KU365778        TKHLIRVENWIFRNPGFALAAAAIAWLLGSSTSQKVIYLVMILLIAPAYSIRCIGVSNRD
KU365779        TKHLIRVENWIFRNPGFALAAAAIAWLLGSSTSQKVIYLVMILLIAPAYSIRCIGVSNRD
KU365780        TKHLIRVENWIFRNPGFALAAAAIAWLLGSSTSQKVIYLVMILLIAPAYSIRCIGVSNRD
Sao             TKHLIRVENWIFRNPGFALAAAAIAWLLGSSTSQKVIYLVMILLIAPAYSIRCIGVSNRD
                ************************************************************
```

*FIG.4B*

```
                                                                    (E)
Natal       FVEGMSGGTWVDVVLEHGGCVTVMAQDKPTVDIELVTTTVSNMAEVRSYCYEASISDMAS
Salvador    FVEGMSGGTWVDVVLEHGGCVTVMAQDKPTVDIELVTTTVSNMAEVRSYCYEASISDMAS
KU365777    FVEGMSGGTWVDVVLEHGGCVTVMAQDKPTVDIELVTTTVSNMAEVRSYCYEASISDMAS
KU365778    FVEGMSGGTWVDVVLEHGGCVTVMAQDKPTVDIELVTTTVSNMAEVRSYCYEASISDMAS
KU365779    FVEGMSGGTWVDVVLEHGGCVTVMAQDKPTVDIELVTTTVSNMAEVRSYCYEASISDMAS
KU365780    FVEGMSGGTWVDVVLEHGGCVTVMAQDKPTVDIELVTTTVSNMAEVRSYCYEASISDMAS
Sao         FVEGMSGGTWVDIVLEHGGCVTVMAQDKPTVDIELVTTTVSNMAEVRSYCYEASISDMAS
            ************:***********************************************

                                                                    (E)
Natal       DSRCPTQGEAYLDKQSDTQYVCKRTLVDRGWGNGCGLFGKGSLVTCAKFACSKKMTGKSI
Salvador    DSRCPTQGEAYLDKQSDTQYVCKRTLVDRGWGNGCGLFGKGSLVTCAKFACSKKMTGKSI
KU365777    DSRCPTQGEAYLDKQSDTQYVCKRTLVDRGWGNGCGLFGKGSLVTCAKFACSKKMTGKSI
KU365778    DSRCPTQGEAYLDKQSDTQYVCKRTLVDRGWGNGCGLFGKGSLVTCAKFACSKKMTGKSI
KU365779    DSRCPTQGEAYLDKQSDTQYVCKRTLVDRGWGNGCGLFGKGSLVTCAKFACSKKMTGKSI
KU365780    DSRCPTQGEAYLDKQSDTQYVCKRTLVDRGWGNGCGLFGKGSLVTCAKFACSKKMTGKSI
Sao         DSRCPTQGEAYLDKQSDTQYVCKRTLVDRGWGNGCGLFGKGSLVTCAKFACSKKMTGKSI
            ************************************************************

                                                                    (E)
Natal       QPENLEYRIMLSVHGSQHSGMIVNDTGHETDENRAKVEITPNSPRAEATLGGFGSLGLDC
Salvador    QPENLEYRIMLSVHGSQHSGMIVNDTGHETDENRAKVEITPNSPRAEATLGGFGSLGLDC
KU365777    QPENLEYRIMLSVHGSQHSGMIVNDTGHETDENRAKVEITPNSPRAEATLGGFGSLGLDC
KU365778    QPENLEYRIMLSVHGSQHSGMIVNDTGHETDENRAKVEITPNSPRAEATLGGFGSLGLDC
KU365779    QPENLEYRIMLSVHGSQHSGMIVNDTGHETDENRAKVEITPNSPRAEATLGGFGSLGLDC
KU365780    QPENLEYRIMLSVHGSQHSGMIVNDTGHETDENRAKVEITPNSPRAEATLGGFGSLGLDC
Sao         QPENLEYRIMLSVHGSQHSGMIVNDTGHETDENRAKVEITPNSPRAEATLGGFGSLGLDC
            ************************************************************

                                                                    (E)
Natal       EPRTGLDFSDLYYLTMNNKHWLVHKEWFHDIPLPWHAGADTGTPHWNNKEALVEFKDAHA
Salvador    EPRTGLDFSDLYYLTMNNKHWLVHKEWFHDIPLPWHAGADTGTPHWNNKEALVEFKDAHA
KU365777    EPRTGLDFSDLYYLTMNNKHWLVHKEWFHDIPLPWHAGADTGTPHWNNKEALVEFKDAHA
KU365778    EPRTGLDFSDLYYLTMNNKHWLVHKEWFHDIPLPWHAGADTGTPHWNNKEALVEFKDAHA
KU365779    EPRTGLDFSDLYYLTMNNKHWLVHKEWFHDIPLPWHAGADTGTPHWNNKEALVEFKDAHA
KU365780    EPRTGLDFSDLYYLTMNNKHWLVHKEWFHDIPLPWHAGADTGTPHWNNKEALVEFKDAHA
Sao         EPRTGLDFSDLYYLTMNNKHWLVHKEWFHDIPLPWHAGADTGTPHWNNKEALVEFKDAHA
            ************************************************************

                                                                    (E)
Natal       KRQTVVVLGSQEGAVHTALAGALEAEMDGAKGRLSSGHLKCRLKMDKLRLKGVSYSLCTA
Salvador    KRQTVVVLGSQEGAVHTALAGALEAEMDGAKGRLSSGHLKCRLKMDKLRLKGVSYSLCTA
KU365777    KRQTVVVLGSQEGAVHTALAGALEAEMDGAKGRLSSGHLKCRLKMDKLRLKGVSYSLCTA
KU365778    KRQTVVVLGSQEGAVHTALAGALEAEMDGAKGRLSSGHLKCRLKMDKLRLKGVSYSLCTA
KU365779    KRQTVVVLGSQEGAVHTALAGALEAEMDGAKGRLSSGHLKCRLKMDKLRLKGVSYSLCTA
KU365780    KRQTVVVLGSQEGAVHTALAGALEAEMDGAKGRLSSGHLKCRLKMDKLRLKGVSYSLCTA
Sao         KRQTVVVLGSQEGAVHTALAGALEAEMDGAKGRLSSGHLKCRLKMDKLRLKGVSYSLCTA
            ************************************************************
```

FIG.4C

```
                ---------------------------------------------------(E)----------
Natal           AFTFTKIPAETLHGTVTVEVQYAGTDGPCKVPAQMAVDMQTLTPVGRLITANPVITESTE
Salvador        AFTFTKIPAETLHGTVTVEVQYAGTDGPCKVPAQMAVDMQTLTPVGRLITANPVITESTE
KU365777        AFTFTKIPAETLHGTVTVEVQYAGTDGPCKVPAQMAVDMQTLTPVGRLITANPVITESTE
KU365778        AFTFTKIPAETLHGTVTVEVQYAGTDGPCKVPAQMAVDMQTLTPVGRLITANPVITESTE
KU365779        AFTFTKIPAETLHGTVTVEVQYAGTDGPCKVPAQMAVDMQTLTPVGRLITANPVITESTE
KU365780        AFTFTKIPAETLHGTVTVEVQYAGTDGPCKVPAQMAVDMQTLTPVGRLITANPVITESTE
Sao             AFTFTKIPAETLHGTVTVEVQYAGTDGPCKVPAQMAVDMQTLTPVGRLITANPVITESTE
                ************************************************************

                ---------------------------------------------------(E)----------
Natal           NSKMMLELDPPFGDSYIVIGVGEKKITHHWHRSGSTIGKAFEATVRGAKRMAVLGDTAWD
Salvador        NSKMMLELDPPFGDSYIVIGVGEKKITHHWHRSGSTIGKAFEATVRGAKRMAVLGDTAWD
KU365777        NSKMMLELDPPFGDSYIVIGVGEKKITHHWHRSGSTIGKAFEATVRGAKRMAVLGDTAWD
KU365778        NSKMMLELDPPFGDSYIVIGVGEKKITHHWHRSGSTIGKAFEATVRGAKRMAVLGDTAWD
KU365779        NSKMMLELDPPFGDSYIVIGVGEKKITHHWHRSGSTIGKAFEATVRGAKRMAVLGDTAWD
KU365780        NSKMMLELDPPFGDSYIVIGVGEKKITHHWHRSGSTIGKAFEATVRGAKRMAVLGDTAWD
Sao             NSKMMLELDPPFGDSYIVIGVGEKKITHHWHRSGSTIGKAFEATVRGAKRMAVLGDTAWD
                ************************************************************

                ---------------------------------------------------(E)----------
Natal           FGSVGGALNSLGKGIHQIFGAAFKSLFGGMSWFSQILIGTLLMWLGLNTKNGSISLMCLA
Salvador        FGSVGGALNSLGKGIHQIFGAAFKSLFGGMSWFSQILIGTLLMWLGLNTKNGSISLMCLA
KU365777        FGSVGGALNSLGKGIHQIFGAAFKSLFGGMSWFSQILIGTLLMWLGLNTKNGSISLMCLA
KU365778        FGSVGGALNSLGKGIHQIFGAAFKSLFGGMSWFSQILIGTLLMWLGLNTKNGSISLMCLA
KU365779        FGSVGGALNSLGKGIHQIFGAAFKSLFGGMSWFSQILIGTLLMWLGLNTKNGSISLMCLA
KU365780        FGSVGGALNSLGKGIHQIFGAAFKSLFGGMSWFSQILIGTLLMWLGLNTKNGSISLMCLA
Sao             FGSVGGALNSLGKGIHQIFGAAFKSLFGGMSWFSQILIGTLLMWLGLNTKNGSISLMCLA
                ************************************************************

                ---(E)-------
Natal           LGGVLIFLSTAVSAD
Salvador        LGGVLIFLSTAVSAD
KU365777        LGGVLIFLSTAVSAD
KU365778        LGGVLIFLSTAVSAD
KU365779        LGGVLIFLSTAVSAD
KU365780        LGGVLIFLSTAVSAD
Sao             LGGVLIFLSTAVSAD
                ***************
```

ZIKA VIRAL ANTIGEN CONSTRUCTS

STATEMENT OF U.S. GOVERNMENT INTEREST

This invention was created in the performance of a Cooperative Research and Development Agreement with the National Institutes of Health, an Agency of the Department of Health and Human Services. The Government of the United States has certain rights in this invention.

FIELD OF THE INVENTION

This invention is in the field of treating and preventing viral infections. In particular, the present invention relates to nucleic acid-based vaccine constructs encoding Zika viral antigens and the use of Zika viral antigens for treating and preventing Zika infections.

BACKGROUND TO THE INVENTION

Zika virus was first identified in Uganda in 1947 in rhesus monkeys through a monitoring network of sylvatic yellow fever. It was subsequently identified in humans in 1952 in Uganda and the United Republic of Tanzania. Outbreaks of Zika virus disease have been recorded in Africa, the Americas, Asia and the Pacific. Zika virus belongs to the genus *Flavivirus*. Its reservoir is unknown.

Zika virus is a plus-strand RNA virus belonging to the family Flaviviridae. Zika virus disease is caused by a virus transmitted primarily by *Aedes* mosquitoes. People with Zika virus disease can have symptoms that can include mild fever, skin rash, conjunctivitis, muscle and joint pain, malaise or headache. These symptoms normally last for 2-7 days.

The Zika virus is known to circulate in Africa, the Americas, Asia and the Pacific. Transmitted by *Aedes* mosquitos, the virus has been known to cause either asymptomatic infection (in the majority of people infected) or a self-limiting illness with descending rash, conjunctivitis and low grade fever. However, during the ongoing Zika virus outbreak in the Americas an alarming increase in the number of babies born with microcephaly, as well as an increase in the incidence of Guillain-Barré syndrome has been reported. In addition to microcephaly, other fetal malformations and neurological disorders have been described.

Dowd et al. (Science, Vol. 354 Issue 6309, pp. 237-40 (2016) recently reported that DNA vaccines expressing the premembrane and envelope proteins of Zika virus were immunogenic in mice and nonhuman primates when administered by electroporation or needle-free injection; and that protection against viremia after Zika virus challenge correlated with serum neutralizing activity.

Chahal et al. (Scientific Reports, 7:252, pp. 1-9 (2017)) describe an alphavirus RNA vector encoding Zika virus structural antigens. When formulated with a modified dendrimer nanomaterial and administered to mice intramuscularly, the vaccine was found to be immunogenic.

Richner et al. (Cell, 168, pp. 1-12, (2017) describe a modified mRNA vaccine encoding wild-type or mutant Zika structural proteins. When encapsulated in lipid nanoparticles and administered intramuscularly to mice, the mRNA vaccine elicited high neutralizing antibody titers and protection from viral challenge.

Given the concerning disease burden and the potential for rapid dissemination, there is an urgent need for the development of components for use in a Zika virus immunogenic or vaccine composition.

SUMMARY OF THE INVENTION

The present inventors provide constructs useful as components of immunogenic compositions for the induction of an immune response in a subject against Zika viral infection, methods for their use in treatment, and processes for their manufacture.

In some embodiments, a nucleic acid-based vaccine construct encoding a polypeptide comprising a full-length Zika virus pre-M-E antigen (prME), or an immunogenic fragment thereof is provided.

In some embodiments, a vector comprising the construct as described is provided.

In some embodiments, a self-replicating RNA molecule (also referred to herein as a self-amplifying mRNA, or SAM molecule) comprising the construct as described is provided.

In some embodiments, a composition comprising an immunologically effective amount of one or more of the constructs, vectors, or self-replicating RNA molecules as described above is provided.

In some embodiments, a composition as described above is provided wherein the composition comprises an RNA-based vaccine.

In some embodiments, a composition as described above is provided wherein the composition comprises one or more constructs, vectors, or self-replicating RNA molecules as described above complexed with a particle of a cationic oil-in-water emulsion.

In some embodiments, a composition as described above for use in inducing an immune response against a Zika virus infection in a subject in need thereof is provided.

In some embodiments, a method is provided for inducing an immune response against a Zika virus infection in a subject in need thereof, which comprises administering to said subject an immunologically effective amount of a composition comprising one or more of the constructs, vectors, or self-replicating RNA molecules as described above.

In some embodiments, a method as described above is provided wherein the composition comprises one or more constructs, vectors, or self-replicating RNA molecules as described above complexed with a particle of a cationic oil-in-water emulsion.

In some embodiments, a process is provided for producing an RNA-based vaccine comprising a step of transcribing a vector or DNA molecule encoding a self-replicating RNA molecule described above to produce an RNA comprising a coding region for the antigen.

In some embodiments, a method of preparing a composition as described above is provided wherein the method comprises 1) preparing a cationic oil-in-water emulsion; 2) preparing one or more constructs, vectors, or self-replicating RNA molecules as described above; and 3) adding the one or more constructs, vectors, or self-replicating RNA molecules to the cationic oil-in-water emulsion so that the construct, vector, or self-replicating RNA molecule complexes with the emulsion.

In some embodiments, a composition produced by the process described above is provided.

In some embodiments, a use of the construct, vector, self-replicating RNA molecule, or composition described above for inducing an immune response against a Zika virus infection in a subject is provided.

In some embodiments, a use of the construct, vector, self-replicating RNA molecule, or composition described above in the manufacture of a medicament that induces an immune response against a Zika virus infection in a subject is provided.

In some embodiments, a construct, vector, self-replicating RNA molecule, or composition described above for use in therapy is provided.

In some embodiments, a construct, vector, self-replicating RNA molecule, or composition described above for use in a method of inducing an immune response to a Zika virus infection in a subject is provided.

DESCRIPTION OF DRAWINGS/FIGURES

FIG. 1: The organization of the *Flavivirus* genome, showing the polyprotein that is cleaved into structural and non-structural proteins by a combination of viral and cellular proteases.

Figure 2:
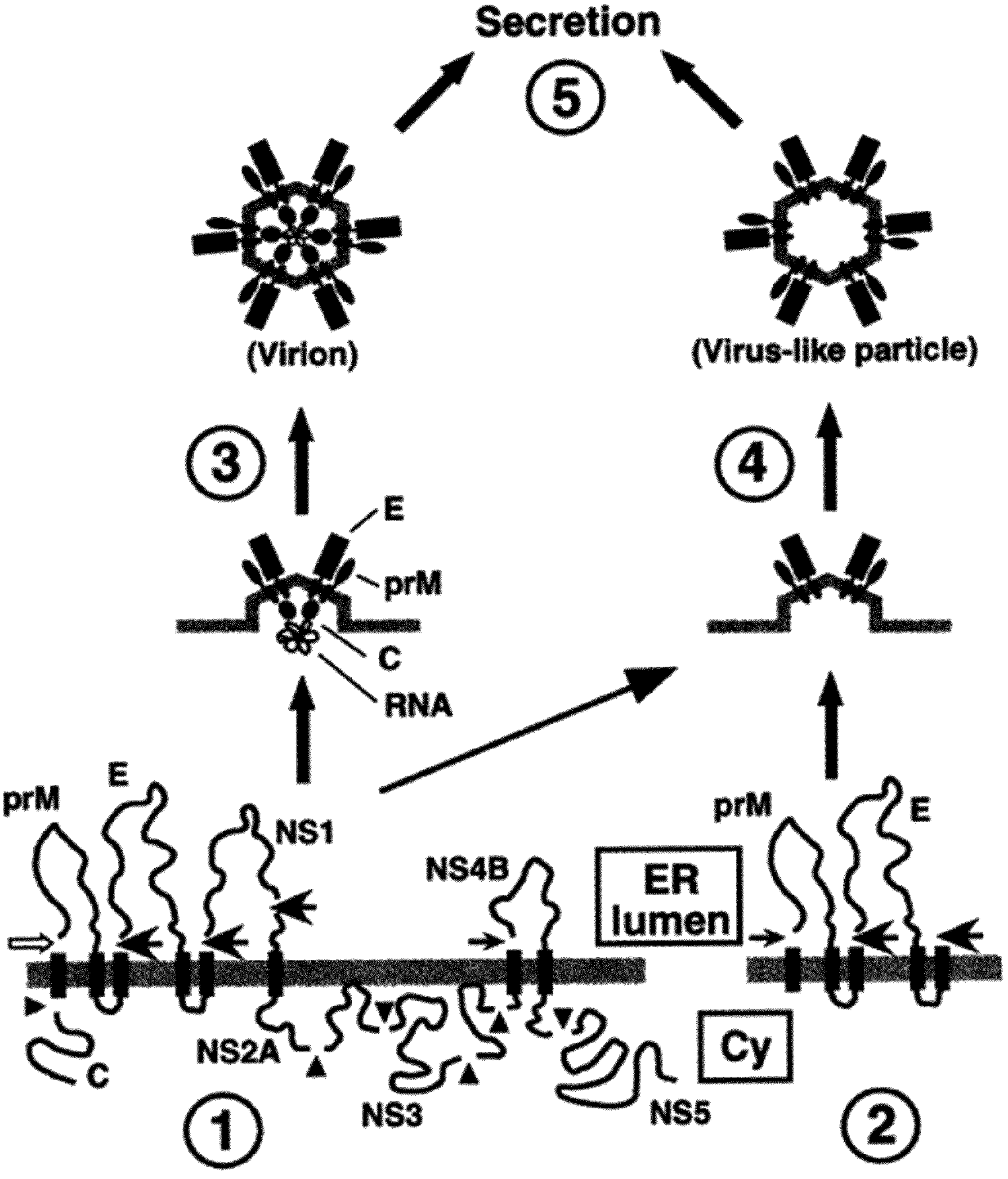

FIG. 2: Formation of *Flavivirus* virions and subviral particles. (1) In natural infections, *Flavivirus* proteins are produced by the processing of a polyprotein translated from the viral genomic RNA and inserted co-translationally into the endoplasmic reticulum (ER) membrane. Horizontal arrows indicate polyprotein cleavages by signal peptidase and arrow heads indicate cleavage by the viral NS2B-3 protease. The open arrow indicates a signalase cleavage which is inefficient unless cytoplasmic capsid (C) cleavage has occurred. (2) The minimal requirement for production of subviral particles is the precursor membrane (prM) and envelope (E) proteins. (3) *Flavivirus* particles are formed by budding on the ER membrane driven by the prM and E proteins independent of the C protein or preformed nucleocapsids. Virus infection results predominantly in the formation of virions. (4) Nucleocapsid-free virus-like particles are efficiently produced by recombinant expression of the prM and E proteins and are a by-product of *Flavivirus* infection. (5) Virions and virus-like particles follow the exocytic pathway for secretion from infected/transfected cells. ‘Cy’ denotes the cytoplasmic side of the ER membrane.

FIG. 3A-D: CLUSTAL O(1.2.1) multiple sequence alignment of CprME proteins of Zika virus strains: Uganda (SEQ ID NO:10); Micronesia (SEQ ID NO:11); Natal (SEQ ID NO:2); Salvador (SEQ ID NO:8); Genbank Accession No. KU365777 (SEQ ID NO:13); Genbank Accession No. KU365778 (SEQ ID NO:14); Genbank Accession No. KU365779 (SEQ ID NO:15); Genbank Accession No. KU365780 (SEQ ID NO:16); French Polynesia (“French”) (SEQ ID NO:12); and Sao Paolo (“Sao”) (SEQ ID NO:9). An “*” (asterisk) indicates positions which have a single, fully conserved residue. A “:” (colon) indicates conservation between groups of strongly similar properties. A “.” (period) indicates conservation between groups of weakly similar properties. The above SEQ ID NOS include the entire sequences shown in FIG. 3A-D for each strain except that SEQ ID NO: 2 does not include the capsid (C) portion of the Natal strain. However, the entire corresponding sequence for the Natal strain is shown in FIG. 3A-3D.

TABLE 1

Zika virus strains, year, and Genbank reference

| STRAIN | YEAR | GENBANK NUMBER |
|---|---|---|
| Uganda | | NC_012532 |
| Micronesia | 2007 | EU545988.1 |
| Natal (Brazil) | 2016 | KU527068 |
| Salvador (Brazil) | 2016 | KU707826.1 |
| Sao Paulo (Brazil) | 2016 | KU321639 |
| French Polynesia | 2013 | KJ776791 |

FIG. 4A-C: CLUSTAL O(1.2.1) multiple sequence alignment of CprME proteins from Brazilian strains of Zika virus: Natal (SEQ ID NO:2); Salvador (SEQ ID NO:8); Genbank Accession No. KU365777 (SEQ ID NO:13); Genbank Accession No. KU365778 (SEQ ID NO:14); Genbank Accession No. KU365779 (SEQ ID NO:15); Genbank Accession No. KU365780 (SEQ ID NO:16); and Sao Paolo (“Sao”) (SEQ ID NO:9). See Table 1 for Zika virus strains, year, and Genbank reference.

Figure 5:
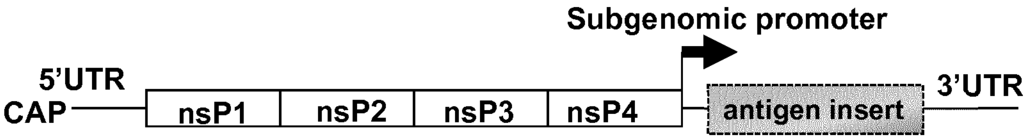

FIG. 5: A SAM-Zika construct. The self-amplifying mRNA (SAM) background consists of VEE TC-83 replicon encoding the viral nonstructural proteins 1-4 (nsP1-4), followed by the subgenomic promoter, and an insert encoding a Zika antigen. The empty vector is shown in SEQ ID NO:17; the insert starts immediately after nucleotide 7561.

Figure 6:
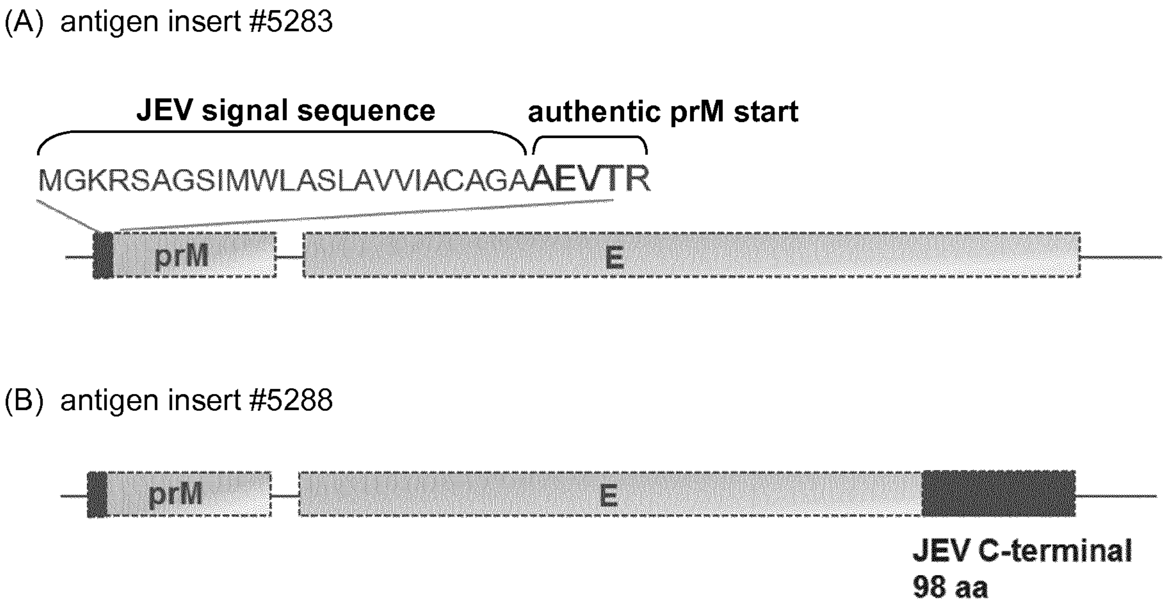

FIG. 6: Design of antigen inserts for Zika-SAM constructs.

Antigen insert #5283, shown in (A), comprises a Japanese Encephalitis Virus (JEV) signal sequence followed by Zika prME, including the wild type prM start sequence (“AEVTR”). The full length amino acid sequence of antigen insert #5283 is shown in SEQ ID NO:19, including the JEV signal sequence (SEQ ID NO:5), followed by the Zika pr region (SEQ ID NO:20), M protein (SEQ ID NO:21) and E protein (SEQ ID NO:22). The DNA and RNA sequences encoding the antigen insert shown in (A) are presented in SEQ ID NOs:18 and 39, respectively.

Antigen insert #5288, shown in (B), is identical to the insert of (A), except that the last 98 amino acids of the Zika E protein are replaced with the last 98 amino acids from the C-terminus of the JEV E protein (Genbank Accession No. AFV52311.1; SEQ ID NO:7). Chang et al. (2003) Virol. 306:170-180. The full length amino acid sequence of antigen insert #5288 is shown in SEQ ID NO:24, including the JEV signal sequence (SEQ ID NO:5), followed by the Zika pr region and M protein (SEQ ID NOS:25 and 26, respectively), and a hybrid Zika-JEV E protein (SEQ ID NO:27). The DNA and RNA sequences encoding the antigen insert shown in (B) are presented in SEQ ID NOs:23 and 40, respectively.

Figure 7:
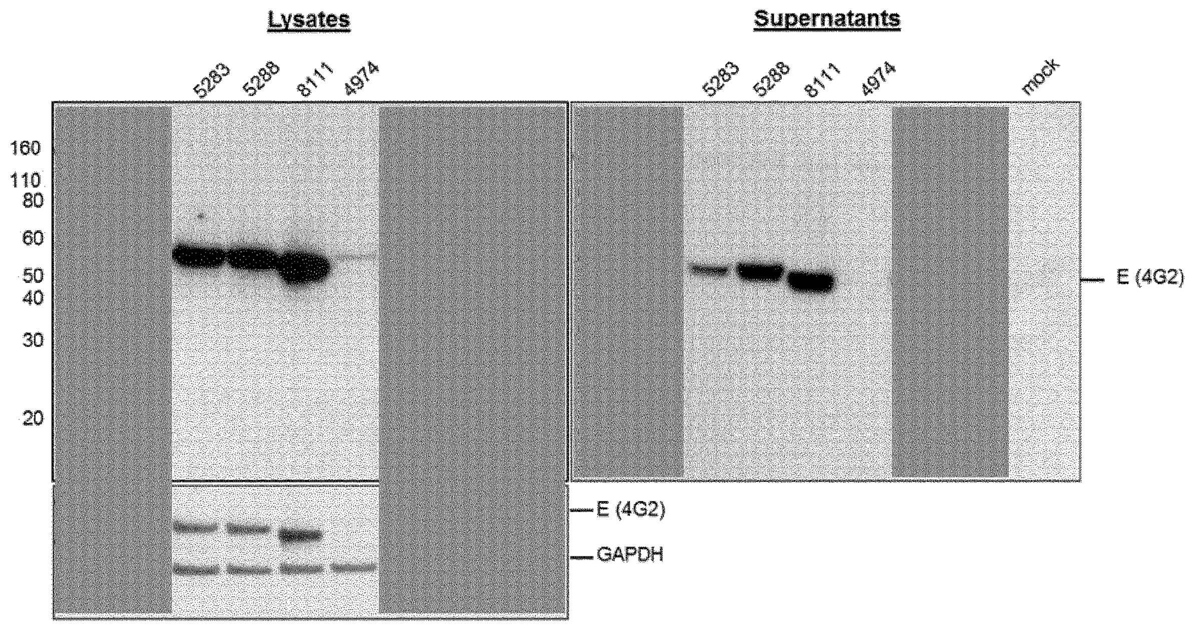

FIG. 7: Analysis of expression and secretion of E protein from Zika-SAM constructs.

Expression and secretion of E protein was detected by immunoblot in cell lysates for self-amplifying mRNA (SAM) constructs encoding antigen inserts #5283 (JEV signal+Zika prME) and #5288 (JEV signal+hybrid Zika-JEV prME). Expression and secretion of E protein was also detected for a positive control antigen construct (#8111) but not for a negative control construct (#4974) or mock transfection (“Mock”). See Example 5.

Figure 8:
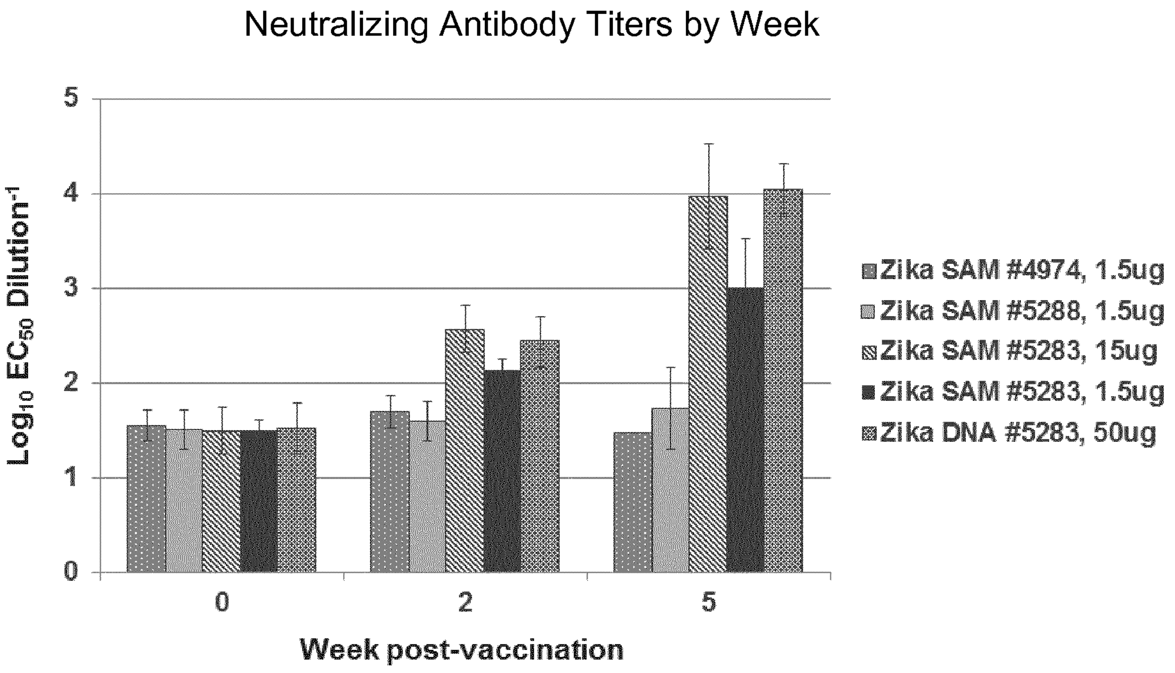

FIG. 8: Neutralizing Antibody Responses in Mice. Mice were found to have significant neutralizing Zika antibodies two weeks after a single vaccination with Zika-SAM construct #5283 (JEV signal+Zika prME), or with positive control Zika DNA construct #5283, as measured by reporter virus particle (RVP) neutralization assay. Neutralizing antibody titers were further increased two weeks after a second vaccination with the same Zika-SAM construct, or the positive control. Neutralizing Zika antibodies were below the limit of quantification before vaccination (Day 0), and after vaccination with negative control construct (#4974, 1.5 μg dose) or with #5288 (JEV signal+hybrid Zika-JEV prME, 1.5 μg dose). A dose-response effect was observed for SAM construct #5283, with 15 ug of RNA eliciting more neutralizing antibodies than 1.5 ug RNA.

Figure 9:
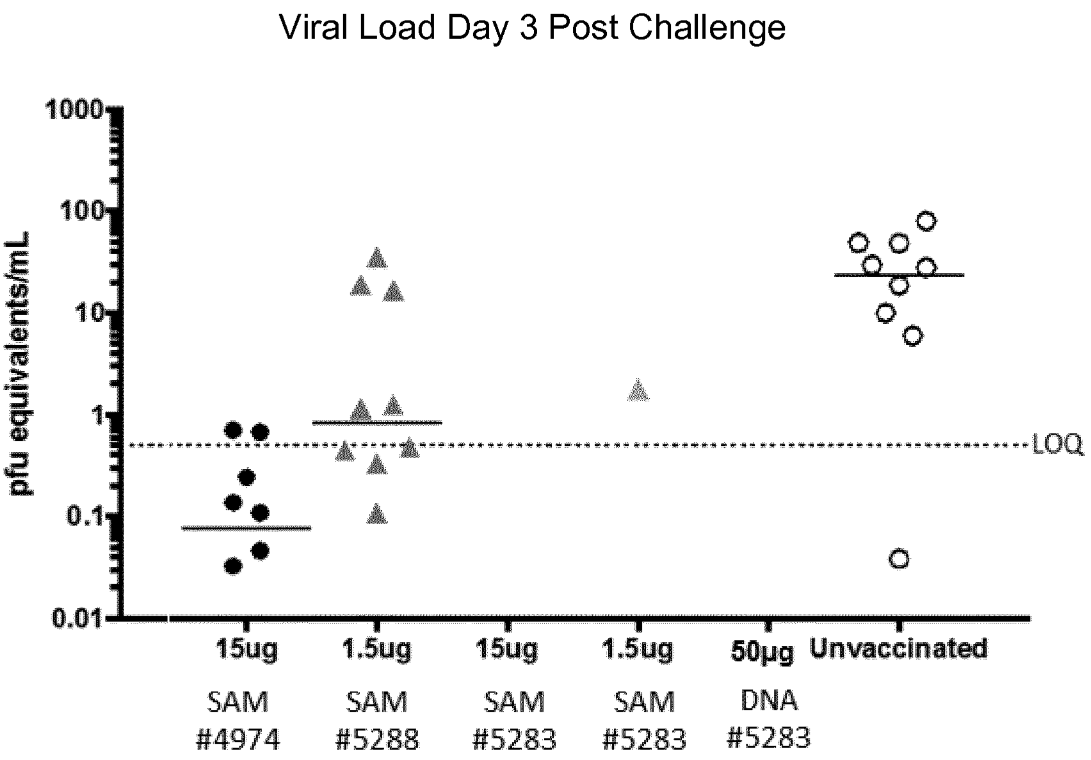

FIG. 9: Protection of Mice from Zika Challenge: Mice vaccinated on days 0 and 21 were challenged with live Zika virus on day 49. Viral load was measured 3 days post-challenge. Vaccination with SAM construct #5283 (at 1.5 μg and 15 μg doses), as well as the positive control (DNA #5283) were protective against Zika viremi. Unvaccinated mice and mice vaccinated with SAM construct #5288 (1.5 μg dose) or negative control construct #4974 were not protected in the Zika challenge. Dotted line indicates the limit of quantification (LOQ) of the assay.

Figure 10:
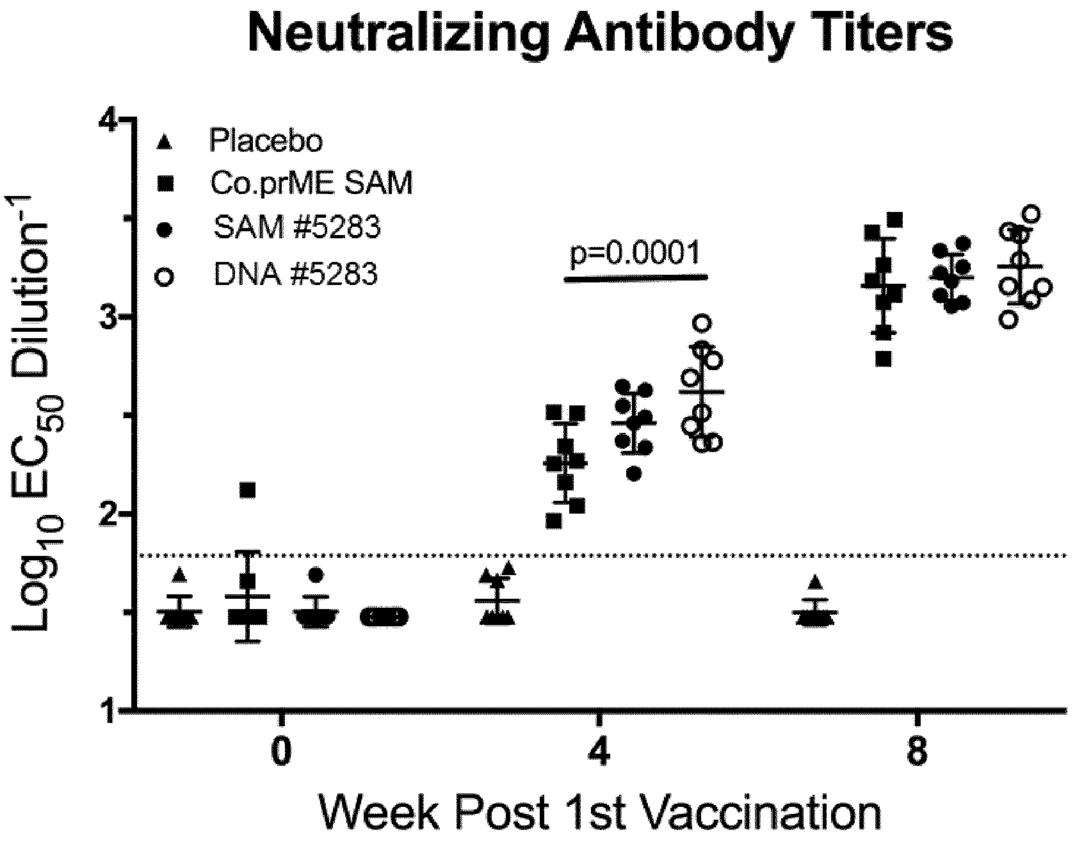

FIG. 10: Neutralizing Antibody Responses in Non-Human Primates (NHPs). Rhesus Macaques were immunized at weeks 0 and 4 with the Zika-SAM construct #5283 (75 μg/dose) or a codon-optimized SAM construct encoding the native Zika prME antigen (Co.prME SAM; 75 μg/dose). Control NHPs were administered placebo or immunized with Zika DNA construct #5283 (4 mg/dose). Zika neutralizing antibodies were significantly elevated four weeks after the first immunization of Zika SAM construct #5283 or Zika DNA #5283 as compared to placebo, with titers being further increased 4 weeks after the second immunization. Zika-SAM construct Co.prME SAM produced significantly less neutralizing antibodies compared to #5283 DNA after a single dose, but similar titers after two injections. Dotted line indicates the limit of quantification (LOQ) of the assay.

Figure 11:
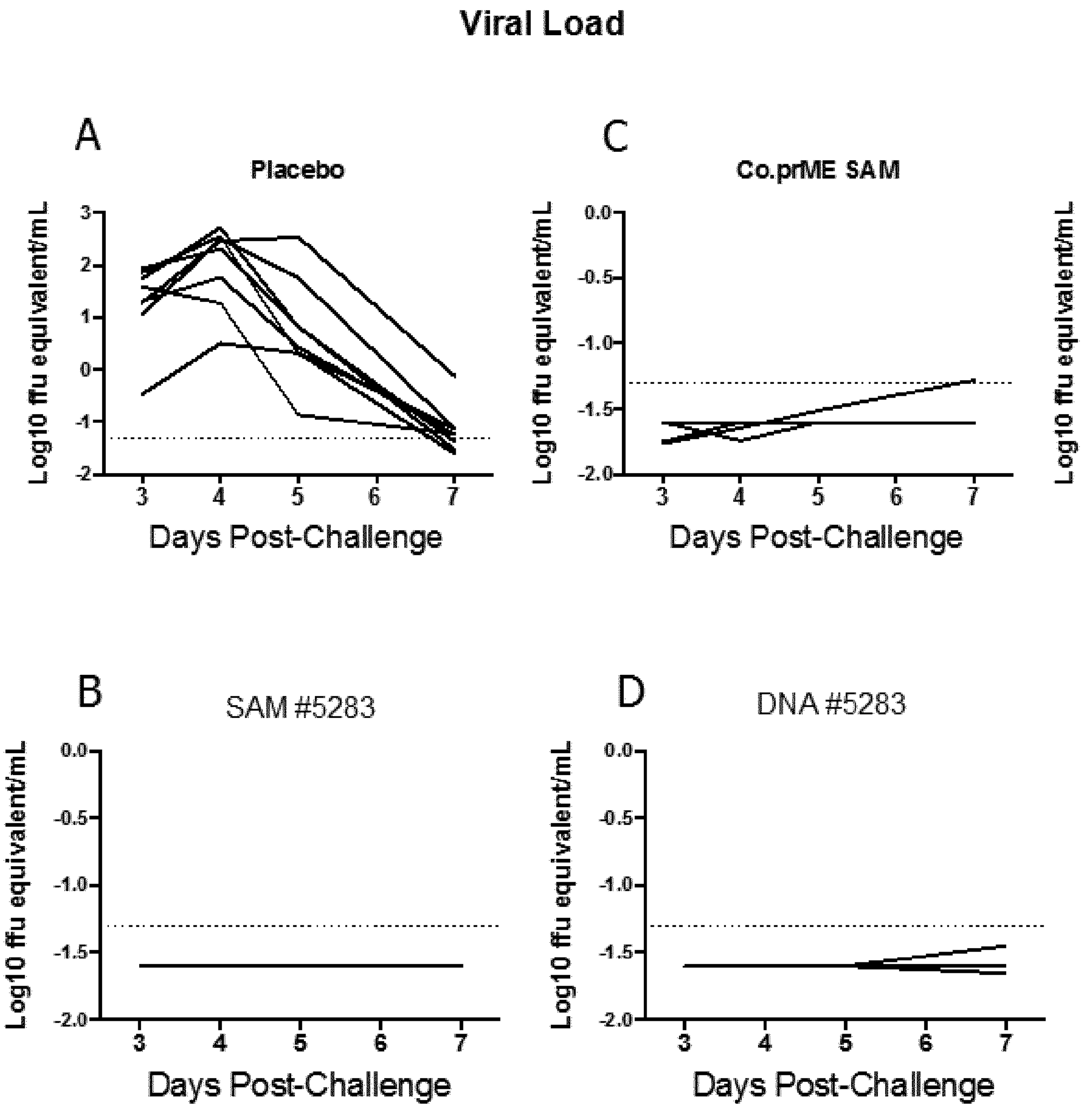

FIG. 11: Protection of NHPs from Zika Challenge: Rhesus Macaques vaccinated as described in FIG. 10 were then challenged with live Zika virus at week 8. Viral load was measured daily from days 3-7 post-challenge. Placebo animals exhibited elevated viremia as early as 3 days post-challenge (A). Vaccination with Zika-SAM construct #5283 (B), Zika-SAM Co.prME (C), and DNA #5283 (D) were protective against Zika viremia, with Zika-SAM construct #5283 exhibiting a complete protection against Zika viremia. Dotted line indicates the limit of quantification (LOQ) of the assay.

Figure 12:
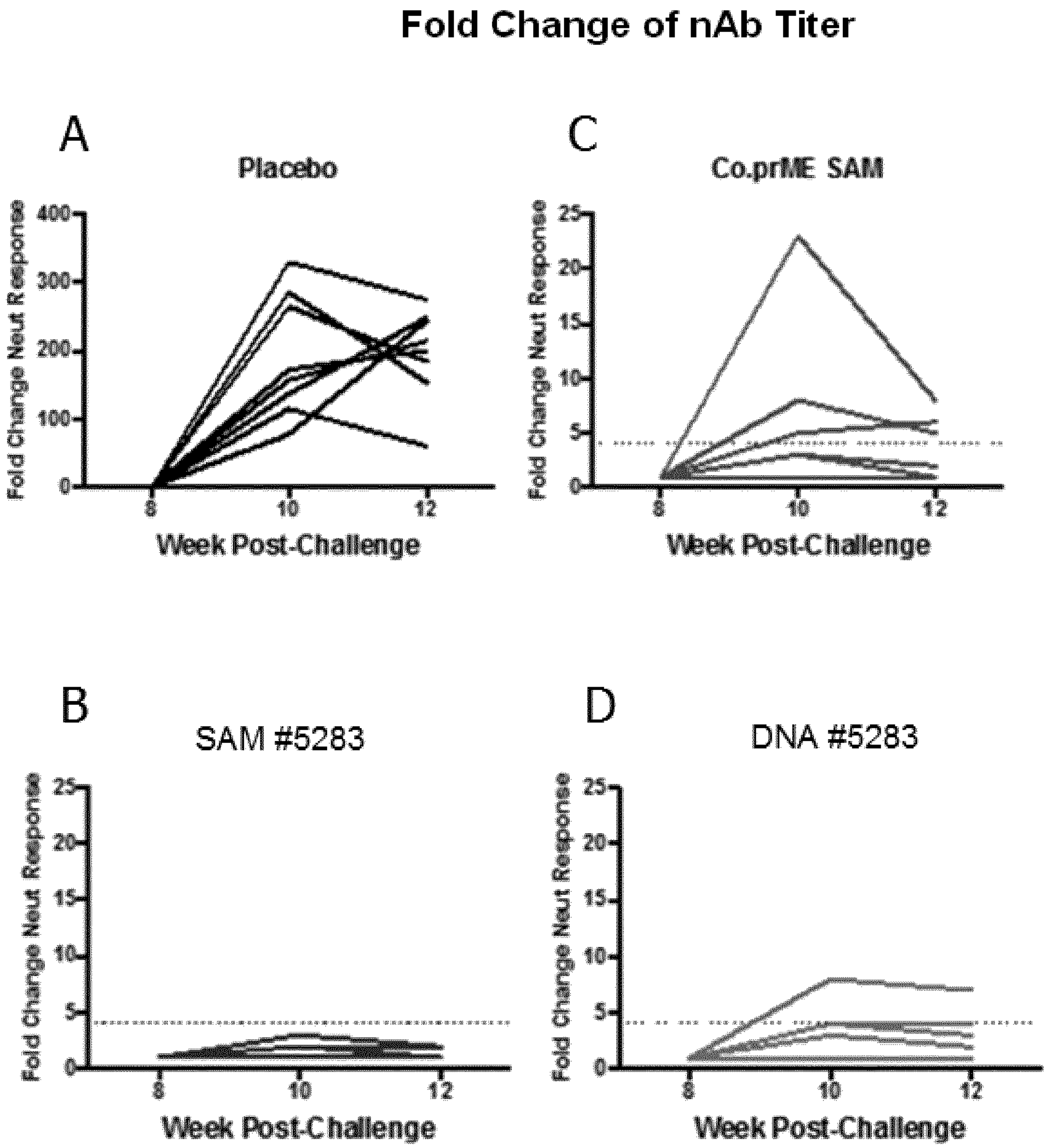

FIG. 12: Post-Challenge Serology in NHPs. Neutralizing antibody titers were determined 8, 10 and 12 weeks after Zika virus challenge, and are expressed as fold-change from pre-challenge levels. Placebo animals showed a sharp rise in neutralizing antibodies after Zika challenge, suggesting Zika infection in these animals. Two animals in the SAM Co.prME group, and one animal in the DNA #5283 group, showed elevated neutralizing antibody titers post-challenge, indicating that protection was not sterilizing in these animals. In contrast, animals in the Zika SAM #5283 group did not exhibit elevated neutralizing antibodies after Zika challenge, indicating that sterilizing protection was achieved in all subjects. Dotted line in (B), (C) and (D) indicates a 4-fold change in neutralizing titers, which is considered non-sterilizing in the *Flavivirus* field.

DETAILED DESCRIPTION OF THE INVENTION

Antigens; Variants; Fragments; and Constructs

The present inventors provide constructs useful as components of immunogenic compositions for the induction of an immune response in a subject against Zika viral infection constructs useful for the expression of antigens, methods for their use in treatment, and processes for their manufacture. By construct is intended a nucleic acid that encodes polypeptide sequences described herein, and may comprise DNA, RNA, or non-naturally occurring nucleic acid monomers. The nucleic acid components of constructs are described more fully in the Nucleic Acids section herein.

In some embodiments, the constructs disclosed herein encode wild-type polypeptide sequences of a Zika virus, or a variant, or a fragment thereof. The constructs may further encode a polypeptide sequence heterologous to the polypeptide sequences of a Zika virus. In some embodiments, the constructs encode wild-type polypeptide sequences of a Brazilian strain Zika virus, or a variant, or a fragment thereof. By "Brazilian strain Zika virus" is intended any strain of Zika virus denoted as "Brazilian" in Table 1. Unless indicated otherwise, descriptions of the wild-type prME antigen are made by reference to the Natal strain (Brazil), GenBank number KU527068.1, as depicted in the SEQ ID NO:1 (nucleic acid) and SEQ ID NO:2 (polypeptide), and as depicted in FIG. 3A-D, and FIG. 4A-C.

A "variant" of a polypeptide sequence includes amino acid sequences having one or more amino acid substitutions, insertions and/or deletions when compared to the reference sequence. The variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:2. Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 19, or more amino acids which is identical to a contiguous amino acid sequence of the full-length polypeptide.

A fragment of a polypeptide may comprise N- and/or C-terminal deletions when compared to a full-length polypeptide, for example SEQ ID NO:2, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids.

As used herein, the term "antigen" refers to a molecule containing one or more epitopes (e.g., linear, conformational or both) that will stimulate a host's immune system to make a humoral and/or cellular antigen-specific immunological response (i.e. an immune response which specifically recognizes an antigen polypeptide). An "epitope" is that portion of an antigen that determines its immunological specificity.

T- and B-cell epitopes can be identified empirically (e.g. using PEPSCAN™ or similar methods). See the following references: Geysen et al. (1984) PNAS USA 81:3998-4002; Carter (1994)*Methods Mol Biol* 36:207-23. They can be predicted (e.g. using the Jameson-Wolf antigenic index (see Jameson et al. (1988) *CABIOS* 4(1): 181-186), matrix-based approaches (see Raddrizzani & Hammer (2000) *Brief Bioinform* 1(2): 179-89), TEPITOPE™ (see De Lalla et al. (1999) *J. Immunol.* 163: 1725-29), neural networks (see Brusic et al. (1998) *Bioinformatics* 14(2): 121-30), OptiMer & EpiMer (see Meister et al. (1995) *Vaccine* 13(6):581-91; see Roberts et al. (1996)*AIDS Res Hum Retroviruses* 12(7): 593-610), ADEPT™ (see Maksyutov & Zagrebelnaya (1993) *Comput Appl Biosci* 9(3):291-7), Tsites (see Feller & de la Cruz (1991) *Nature* 349(6311): 720-1), hydrophilicity (see Hopp (1993) *Peptide Research* 6: 183-190), antigenic index (see Welling et al. (1985)*FEBS Lett.* 188:215-218) or the methods disclosed in reference Davenport et al. (1995) *Immunogenetics* 42:392-297, etc.).

In some embodiments, the constructs herein encode a Zika virus prME antigen. By "Zika virus prME antigen" is intended the amino acid sequence, or a nucleotide sequence encoding the amino acid sequence, of a wild-type Zika virus structural protein prME, a variant, or a fragment thereof. FIG. 3 and FIG. 4 identify the amino acid sequence of several full-length wild-type Zika virus prME structural protein variants. The sequence identifier numbers for each are set forth in the Sequence Listing herein. See SEQ ID NOS:2 and 8-16.

Thus, where a Zika virus prME antigen is a variant of a wild-type prME polypeptide, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NOS:2 and 8-16. Alternatively, or in addition, a fragment of a polypeptide may comprise an immunogenic fragment (i.e. an epitope-containing fragment) of the full-length polypeptide which may comprise a contiguous amino acid sequence of at least 8, at least 9, at least 10, at least 11, at least 12, at least 13, at least 14, at least 15, at least 16, at least 17, at least 18, at least 19, or more amino acids which is identical to a contiguous amino acid sequence of the full-length polypeptide.

A fragment of a Zika virus prME polypeptide may comprise N- and/or C-terminal deletions when compared to a full-length polypeptide, for example SEQ ID NOS:2 and 8-16, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids. In some embodiments, the Zika virus prME polypeptide comprises a fragment selected from the group consisting of amino acids 1 to 692 of SEQ ID NO:2 and amino acids 21 to 692 of SEQ ID NO:2.

In some embodiments, an immunogenic fragment of a prME antigen comprises the full-length of the Zika virus M antigen. By "Zika virus M antigen" is intended the amino acid sequence, or a nucleotide sequence encoding the amino acid sequence, of SEQ ID NO:21. Where a Zika virus M antigen is a variant of a wild-type M polypeptide, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:21.

A fragment of a Zika virus M antigen may comprise N- and/or C-terminal deletions when compared to a full-length polypeptide, for example SEQ ID NO:21, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids.

In some embodiments, an immunogenic fragment of a prME antigen comprises the full-length of the Zika virus E antigen. By "Zika virus E antigen" is intended the amino acid sequence, or a nucleotide sequence encoding the amino acid sequence, of SEQ ID NO:22. Where a Zika virus E antigen is a variant of a wild-type E polypeptide, the variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:22. In some embodiments, a variant Zika virus E antigen may be a hybrid E antigen comprising an N-terminal fragment of a Zika E protein fused to a C-terminal fragment of a heterologous viral E protein. In some embodiments, the heterologous viral E protein is derived from a heterologous *Flavivirus*, such as Japanese Encephalitis Virus (JEV).

A fragment of a Zika virus E antigen may comprise N- and/or C-terminal deletions when compared to a full-length polypeptide, for example SEQ ID NO:22, wherein the fragment comprises a deletion of up to 1, 2, 3, 4, 5, 6, 7, 8, 9, 10, 15 or 20 amino acids from the N-terminus, the C-terminus, or both the N-terminus and C-terminus of the full-length sequence. It may be specified that the deletions are of consecutive amino acids.

In some embodiments, a variant Zika virus prME antigen comprises a hybrid Zika-JEV E protein. A hybrid Zika-JEV E antigen may comprise an N-terminal fragment of a Zika E protein comprising at least amino acids (1+x) to (422±y) of SEQ ID NO:22, where x is a whole number selected from 0, 1, 2, 3, 4, 5, 6, 7, 8, 9, 10, 11, 12, 13, 14, 15, 16, 17, 18, 19 or 20; and y is a whole number selected from 0, 1, 2, 3, 4, 5, 6, 7, 8, 9, 10, 11, 12, 13, 14, 15, 16, 17, 18, 19 or 20. In one embodiment, the N terminal fragment of a Zika E protein comprises amino acids 1 to 422 of SEQ ID NO:22.

A hybrid E antigen may comprise a C-terminal fragment of a JEV E protein comprising at least amino acids (205±x) to (302±y) of SEQ ID NO:7, where x is a whole number selected from 0, 1, 2, 3, 4, 5, 6, 7, 8, 9, 10, 11, 12, 13, 14, 15, 16, 17, 18, 19 or 20; and y is a whole number selected from 0, 1, 2, 3, 4, 5, 6, 7, 8, 9, 10, 11, 12, 13, 14, 15, 16, 17, 18, 19 or 20. In one embodiment, the C-terminal fragment of a JEV E protein comprises amino acids 205 to 302 of SEQ ID NO:7.

In one embodiment, a hybrid E antigen comprises the amino acid sequence of SEQ ID NO:27, or a fragment or variant thereof. A variant may comprise an amino acid sequence which is at least 70%, at least 75%, at least 80%, at least 85%, at least 90%, at least 95%, at least 96%, at least 97%, at least 98%, or at least 99% identical to the polypeptide according to SEQ ID NO:27. Alternatively, or in addition, a fragment of a polypeptide may comprise an immunogenic fragment (i.e. an epitope-containing fragment) of the full-length polypeptide, such as a contiguous amino acid sequence of at least 50, at least 100, at least 150, at least 200, at least 250, at least 300, at least 350, at least 400, at least 450, at least 500 or more amino acids which is identical to a contiguous amino acid sequence of SEQ ID NO:27.

As noted elsewhere herein, the Zika virus RNA is translated as a polyprotein comprising a prM signal sequence. The prM signal sequence is located N-terminal to the prM antigen sequence. Cleavage occurs in the ER lumen by a cellular signal peptidase and generates the N terminus of prM. Where the polyprotein comprises a wild-type amino acid sequence, the polyprotein comprises a native prM signal sequence, SEQ ID NO:3. By "native prM signal sequence" is intended the amino acid sequence, or a nucleotide sequence encoding the amino acid sequence, of a signal sequence of a wild-type viral prME, SEQ ID NO:3. FIG. 3A-B and FIG. 4A identify the amino acid sequence of several full-length native prM signal sequence variants from various Zika virus strains.

In some embodiments, the constructs encode a native prM signal sequence. Where the prM signal sequence is a variant of a native prM signal sequence, the variant may comprise an amino acid sequence which is at least 70%, at least 75%, at least 80%, at least 85%, at least 90%, at least 95%, at least 96%, at least 97%, at least 98%, or at least 99% identical to the full-length polypeptide according to SEQ ID NO:3. Alternatively, or in addition, a fragment of a polypeptide may comprise a functional fragment (i.e., containing the sequence recognized and cleaved by the protease) of the full-length polypeptide which may comprise a contiguous amino acid sequence of at least 9, at least 10, at least 11, at least 12, at least 13, at least 14, at least 15, at least 16, at least 17 amino acids of SEQ ID NO:3 which is identical to a contiguous amino acid sequence of full-length polypeptide.

In some embodiments, the construct encodes a heterologous, non-Zika signal sequence. In some embodiments, the construct encodes a Japanese Encephalitis Virus (JEV) signal sequence, a variant, or a fragment thereof, in place of the Zika prM signal sequence. By "JEV signal sequence" is intended the amino acid sequence as set forth in FIG. 6: MGKRSAGSIMWLASLAVVIACAGA (SEQ ID NO:5). A variant may comprise an amino acid sequence which is at least 70%, at least 75%, at least 80%, at least 85%, at least 90%, at least 95%, at least 96%, at least 97%, at least 98%, or at least 99% identical to a full-length wild-type polypeptide, for example, to a polypeptide according to SEQ ID NO:5. Alternatively, or in addition, a fragment of a polypeptide may comprise a functional fragment (i.e., containing the sequence recognized and cleaved by the protease) of the full-length polypeptide which may comprise a contiguous amino acid sequence of at least 15, at least 16, at least 17, at least 18, at least 19, at least 20, at least 21, at least 22 at least 23 amino acids, which is identical to a contiguous amino acid sequence of the full-length polypeptide.

In some embodiments, the construct encodes a polypeptide comprising from the N-terminal portion to the C-terminal portion: a JEV signal sequence and a Zika prME antigen, variant, or immunogenic fragment thereof. In some embodiments, the construct encodes a polypeptide comprising from the N-terminal portion to the C-terminal portion: a JEV signal sequence, a Zika prM antigen, and a hybrid E antigen comprising an N-terminal fragment of a Zika E protein fused to a C-terminal fragment of a JEV E protein.

In some embodiments, a construct encodes each component of the polypeptide, if present, juxtaposed immediately next to the adjacent component, i.e., without any intervening amino acids. In some embodiments, a linker group of 1, 2, 3, 4, or 5 amino acids is present between one or more of the components.

In some embodiments, the construct encodes a polypeptide having a sequence selected from the group consisting of SEQ ID NO:19 and SEQ ID NO:24. In some embodiments, the construct encodes a polypeptide which is at least 70%, at least 75%, at least 80%, at least 85%, at least 90%, at least 95%, at least 96%, at least 97%, at least 98%, or at least 99% identical to a sequence selected from the group consisting of SEQ ID NO:19 and SEQ ID NO:24. In some embodiments, the construct encodes a polypeptide which comprises a fragment of a full-length sequence selected from the group consisting of SEQ ID NO:19 and SEQ ID NO:24, wherein the fragment comprises a contiguous stretch of the amino acid sequence of the full-length sequence up to 1, 2, 3, 4, 5, 6, 7, 8, 9, or 10 amino acids shorter than the full-length sequence.

In some embodiments, the construct comprises a DNA sequence selected from the group consisting of SEQ ID NO:18 and SEQ ID NO:23. In some embodiments, the construct comprises a DNA sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:18 and SEQ ID NO:23. In some embodiments, the construct comprises a DNA sequence which comprises a fragment of a full-length sequence selected from the group consisting of SEQ ID NO:18 and SEQ ID NO:23 wherein the fragment comprises a contiguous stretch of the DNA sequence of the full-length sequence up to 1, 2, 3, 4, 5, 6, 7, 8, 9, 10, 15, 20, 25, or 30 nucleic acids shorter than the full-length sequence.

In some embodiments, the construct comprises an RNA sequence selected from the group consisting of SEQ ID NO:39 and SEQ ID NO:40. In some embodiments, the construct comprises an RNA sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:39 and SEQ ID NO:40. In some embodiments, the construct comprises an RNA sequence which comprises a fragment of a full-length sequence selected from the group consisting of SEQ ID NO:39 and SEQ ID NO:40 wherein the fragment comprises a contiguous stretch of the RNA sequence of the full-length sequence up to 1, 2, 3, 4, 5, 6, 7, 8, 9, 10, 15, 20, 25, or 30 nucleic acids shorter than the full-length sequence.

In some embodiments, the construct comprises a fragment of a full-length RNA sequence selected from the group consisting of SEQ ID NO:39 and SEQ ID NO:40, wherein the fragment comprises a deletion of up to 1, 2, 3, 4, 5, 6, 7, 8, 9, 10, 15, 20, 25, or 30 nucleic acids from the 5' end, the 3' end, or both the 5' and 3' ends of the full-length sequence.

Polypeptides

In some embodiments, a polypeptide herein is in a non-naturally occurring form (e.g. a recombinant or modified form).

For example, polypeptides (e.g. antigens) disclosed herein can be prepared by chemical synthesis (in whole or in part), by digesting longer polypeptides using proteases, by translation from RNA, by purification from cell culture (e.g. from recombinant expression), from the organism itself, etc. An exemplary method for production of peptides <40 amino acids long involves in vitro chemical synthesis, see the following references: Bodanszky (1993) Principles of Peptide Synthesis (ISBN: 0387564314); and Fields et al. (1997) Meth Enzymol 289: Solid-Phase Peptide Synthesis. ISBN: 0121821900. Solid-phase peptide synthesis techniques, such as methods based on tBoc or Fmoc chemistry, are known in the art, see the following reference: Chan & White (2000) Fmoc Solid Phase Peptide Synthesis. ISBN: 0199637245. Enzymatic synthesis may also be used in part or in full, see the following reference: Kullmann (1987) Enzymatic Peptide Synthesis. ISBN: 0849368413. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non-natural amino acids, such as iodotyrosine or methylphenylalanine, azidohomoalanine, etc.), see the following reference: Kullmann (1987) Enzymatic Peptide Synthesis. ISBN: 0849368413. Where D-amino acids are included, however, it is preferred to use chemical synthesis. Polypeptides of the disclosure may have covalent modifications at the C-terminus and/or N-terminus. They can also take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.). The polypeptides can be naturally or non-naturally glycosylated (i.e. the polypeptide may have a glycosylation pattern that differs from the glycosylation pattern found in the corresponding naturally occurring polypeptide).

Non-naturally occurring forms of polypeptides herein may comprise one or more heterologous amino acid sequences (e.g. another antigen sequence, another signal sequence, a detectable tag, or the like) in addition to a Zika virus prME antigen sequence or a chimeric Zika virus prME sequence. For example, a polypeptide herein may be a fusion protein. Alternatively, or in addition, the amino acid sequence or chemical structure of the polypeptide may be modified (e.g. with one or more non-natural amino acids, by covalent modification, and/or or by having a different glycosylation pattern, for example, by the removal or addition of one or more glycosyl groups) compared to a naturally-occurring polypeptide sequence.

Polypeptides (e.g. antigens) disclosed herein are preferably provided in purified or substantially purified form i.e. substantially free from other polypeptides (e.g. free from naturally-occurring polypeptides), particularly from other Zika virus or host cell polypeptides; for example, at least about 50% pure (by weight), at least about 60% pure (by weight), at least about 70% pure (by weight), at least about 80% pure (by weight), or at least about 90% pure, etc. Alternatively, less than about 50%, less than about 40%, less than about 30%, less than about 20%, less than about 10%, or less than about 5% of a composition is made up of other expressed polypeptides.

Nucleic Acids

The present inventors disclose herein nucleic acid molecules comprising a sequence which encodes a Zika virus prME antigen. Nucleic acids as disclosed herein can take various forms (e.g. single-stranded, double-stranded, vectors etc.). Nucleic acids may be circular or branched, but will generally be linear.

The nucleic acids used herein are preferably provided in purified or substantially purified form i.e. substantially free from other nucleic acids (e.g. free from naturally-occurring nucleic acids), particularly from other Zika virus or host cell nucleic acids, generally being at least about 50% pure (by weight), at least about 60% pure (by weight), at least about 70% pure (by weight), at least about 80% pure (by weight), and usually at least about 90% pure (by weight).

Nucleic acids may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

The term "nucleic acid" in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the nucleic acid of the disclosure includes mRNA, DNA, cDNA, recombinant nucleic acids, branched nucleic acids, plasmids, vectors, etc. Where the nucleic acid takes the form of RNA, it may or may not have a 5' cap.

The nucleic acids herein comprise a sequence which encodes at least one Zika virus prME antigen. Typically, the nucleic acids of the invention will be in recombinant form, i.e. a form which does not occur in nature. For example, the nucleic acid may comprise one or more heterologous nucleic acid sequences (e.g. a sequence encoding another antigen and/or a control sequence such as a promoter or an internal ribosome entry site) in addition to the sequence encoding at least one Zika virus prME antigen. The nucleic acid may be part of a vector i.e. part of a nucleic acid construct designed for transduction/transfection of one or more cell types. Vectors may be, for example, "expression vectors" which are designed for expression of a nucleotide sequence in a host cell, or "viral vectors" which are designed to result in the production of a recombinant virus or virus-like particle.

Alternatively, or in addition, the sequence or chemical structure of the nucleic acid may be modified compared to a naturally-occurring sequence which encodes a Zika virus prME antigen. The sequence of the nucleic acid molecule may be modified, e.g. to increase the efficacy of expression or replication of the nucleic acid, or to provide additional stability or resistance to degradation.

The nucleic acid encoding the polypeptides described above may be codon optimized. By "codon optimized" is intended modification with respect to codon usage that may increase translation efficacy and/or half-life of the nucleic acid. A poly A tail (e.g., of about 30 adenosine residues or more) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methytransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O] N), which may further increase translation efficacy.

The nucleic acids may comprise one or more nucleotide analogs or modified nucleotides. As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate. The preparation of nucleotides and modified nucleotides and nucleosides are well-known in the art, see the following references: U.S. Pat. Nos. 4,373,071, 4,458,066, 4,500,707, 4,668,777, 4,973,679, 5,047,524, 5,132,418, 5,153,319, 5,262,530, 5,700,642. Many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-0-methyluridine), mIA (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6- isopentenyladenosine); io6A (N6-(cis-hydroxyisopentenyl) adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A(N6-hydroxynorvalylcarbamoyl adenosine); ms2hn6A (2-methylthio-N6-hydroxynorvalyl carbamoyladenosine); Ar(p) (2'-0-ribosyladenosine (phosphate)); I (inosine); mil (1-methylinosine); m'lm (l,2'-O-dimethylinosine); m3C (3-methylcytidine); Cm (2T-0-methylcytidine); s2C (2-thiocytidine); ac4C (N4-acetylcytidine); 5FC (5-fonnylcytidine); m5Cm (5,2-O-dimethylcytidine); ac4Cm (N4acetyl2TOmethylcytidine); k2C (lysidine); mlG (1-methylguanosine); m2G (N2-methylguanosine); m7G (7-methylguanosine); Gm (2'-0-methylguanosine); m22G (N2,N2-dimethylguanosine); m2Gm (N2,2'-0-dimethylguanosine); m22Gm (N2,N2,2'-0-trimethylguanosine); Gr(p) (2'-0-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine); m5Um (5,2'-0-dimethyluridine); s4U (4-thiouridine); m5s2U (5-methyl-2-thiouridine); s2Um (2-thio-2'-0-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-0-methyluridine); cmnm5U (5-carboxymethylaminomethyluridine); cnmm5Um (5-carboxymethy 1 aminomethyl-2-L-Omethyl uridine); cmnm5s2U (5-carboxymethylaminomethyl-2-thiouridine); m62A (N6,N6-dimethyladenosine); Tm (2'-0-methylinosine); m4C (N4-methylcytidine); m4Cm (N4,2-0-dimethylcytidine); hm5C (5-hydroxymethylcytidine); m3U (3-methyluridine); cm5U (5-carboxymethyluridine); m6Am (N6,T-0-dimethyladenosine); rn62Am (N6,N6,0-2-trimethyladenosine); m2'7G (N2,7-dimethylguanosine); m2'2'7G (N2,N2,7-trimethylguanosine); m3Um (3,2T-0-dimethyluridine); m5D (5-methyldihydrouridine); £5Cm (5-formyl-2'-0-methylcytidine); mlGm (l,2'-0-dimethylguanosine); m'Am (1,2-O-dimethyl adenosine) irinomethyluridine); tm5s2U (S-taurinomethyl-2-thiouridine)); iniG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-(Ci-Ce)-alkyluracil, 5-methyluracil, 5-(C2-C6)-alkenyluracil, 5-(C2-Ce)-alkynyluracil, 5-(hydroxymethyl)uracil, 5-chlorouracil, 5-fluorouracil, 5-bromouracil, 5-hydroxycytosine, 5-(Ci-C6)-alkylcytosine, 5-methylcytosine, 5-(C2-C6)-alkenylcytosine, 5-(C2-C6)-alkynylcytosine, 5-chlorocytosine, 5-fluorocytosine, 5-bromocytosine, N2-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-0-methyl-U. Many of these modified nucleobases and their corresponding ribonucleosides are available from commercial suppliers.

Nucleic Acid-Based Vaccines

The present inventors disclose compositions comprising a nucleic acid sequence which encodes a polypeptide comprising a Zika virus antigen, variant or fragment thereof. Such compositions may be a nucleic acid-based vaccine. A further composition comprising a nucleic acid sequence which encodes one or more additional (e.g., a second, third, fourth, fifth or sixth) Zika virus antigens may also be provided as a nucleic acid-based vaccine. In some embodiments, a composition comprises a nucleic acid sequence encoding a Zika virus prME antigen from a first Zika virus strain and an additional nucleic acid sequence encoding an additional Zika virus prME antigen from one or more other strains of Zika virus. In some embodiments, a composition comprises a nucleic acid sequence encoding a Zika virus prME antigen and one or more additional (e.g., a second, third, fourth, fifth or sixth) Zika virus antigen. Alternatively, one or more additional non-Zika virus antigens may be encoded.

The nucleic acid may, for example, be RNA (i.e. an RNA-based vaccine) or DNA (i.e. a DNA-based vaccine, such as a plasmid DNA vaccine). In certain embodiments, the nucleic acid-based vaccine is an RNA-based vaccine. In certain embodiments, the RNA-based vaccine comprises a self-replicating RNA molecule, also referred to herein as a self-amplifying mRNA (SAM) molecule. The self-replicating RNA molecule may be an alphavirus-derived RNA replicon.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a +-strand molecule which can be directly translated after delivery to a cell, and this translation provides a RNA-dependent RNA polymerase which then produces both antisense and sense transcripts from the delivered RNA. Thus, the delivered RNA leads to the production of multiple daughter RNAs. These daughter RNAs, as well as collinear subgenomic transcripts, may be translated themselves to provide in situ expression of an encoded antigen (i.e. a Zika virus prM-F antigen), or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells.

One suitable system for achieving self-replication in this manner is to use an alphavirus-based replicon. These replicons are +-stranded (positive sense-stranded) RNAs which lead to translation of a replicase (or replicase-transcriptase) after delivery to a cell. The replicase is translated as a polyprotein which auto-cleaves to provide a replication complex which creates genomic-strand copies of the +-strand delivered RNA. These negative (−)-stranded transcripts can themselves be transcribed to give further copies of the +-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc. Mutant or wild-type virus sequences can be used e.g. the attenuated TC83 mutant of VEEV has been used in replicons, see the following reference: WO2005/113782, the context of which is incorporated by reference.

In certain embodiments, the self-replicating RNA molecule described herein encodes (i) a RNA-dependent RNA polymerase which can transcribe RNA from the self-replicating RNA molecule and (ii) a Zika virus prME antigen. The polymerase can be an alphavirus replicase e.g. comprising one or more of alphavirus proteins nsPl, nsP2, nsP3 and nsP4.

Whereas natural alphavirus genomes encode structural virion proteins in addition to the non-structural replicase polyprotein, in certain embodiments, the self-replicating RNA molecules do not encode alphavirus structural proteins. Thus, the self-replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self-replicating RNAs of the present disclosure and their place is taken by gene(s) encoding the immunogen of interest, such that the subgenomic transcript encodes the immunogen rather than the structural alphavirus virion proteins.

Thus, a self-replicating RNA molecule useful with the invention may have two open reading frames. The first (5') open reading frame encodes a replicase; the second (3') open reading frame encodes an antigen. In some embodiments, the RNA may have additional (e.g. downstream) open reading frames e.g. to encode further antigens or to encode accessory polypeptides.

In certain embodiments, the self-replicating RNA molecule disclosed herein has a 5' cap (e.g. a 7-methylguanosine). This cap can enhance in vivo translation of the RNA. In some embodiments, the 5' sequence of the self-replicating RNA molecule must be selected to ensure compatibility with the encoded replicase.

A self-replicating RNA molecule may have a 3' poly-A tail. It may also include a poly-A polymerase recognition sequence (e.g. AAUAAA) near its 3' end.

Self-replicating RNA molecules can have various lengths but they are typically 5000-25000 nucleotides long. Self-replicating RNA molecules will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

The self-replicating RNA can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the self-replicating RNA from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase.

A self-replicating RNA can include (in addition to any 5' cap structure) one or more nucleotides having a modified nucleobase. A RNA used with the invention ideally includes only phosphodiester linkages between nucleosides, but in some embodiments, it can contain phosphoramidate, phosphorothioate, and/or methylphosphonate linkages.

The self-replicating RNA molecule may encode a single heterologous polypeptide antigen (i.e. a Zika virus prME antigen) or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences.

The self-replicating RNA molecules described herein may be engineered to express multiple nucleotide sequences, from two or more open reading frames, thereby allowing co-expression of proteins, such as one, two or more Zika virus antigens (e.g. one, two or more Zika virus prME antigens) together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self-replicating RNA molecule that encodes a Zika virus prME antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a Zika virus prME antigen can also be tested for ability to induce humoral immune responses, as evidenced, for example, by induction of B cell production of antibodies specific for a Zika virus prME antigen of interest. These assays can be conducted using, for example, peripheral B lymphocytes from immunized individuals. Such assay methods are known to those of skill in the art. Other assays that can be used to characterize the self-replicating RNA molecules can involve detecting expression of the encoded Zika virus prME antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

In some embodiments, the self-replicating RNA molecules comprise a sequence selected from the group consisting of SEQ ID NO:36 and SEQ ID NO:37. In some embodiments, the self-replicating RNA molecules comprise a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:36 and SEQ ID NO:37. In some embodiments, the self-replicating RNA molecule comprises a fragment of a full-length sequence selected from the group consisting of SEQ ID NO:36 and SEQ ID NO:37 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence.

In some embodiments, a DNA sequence encoding a self-replicating RNA molecule is provided, said DNA sequence selected from the group consisting of SEQ ID NO:33 and SEQ ID NO:34. In some embodiments, DNA sequence encoding a self-replicating RNA molecule comprises a sequence which is at least 70%, at least 75%, at least 80%, at least 85%, at least 90%, at least 95%, at least 96%, at least 97%, at least 98%, or at least 99% identical to a sequence selected from the group consisting of SEQ ID NO:33 and SEQ ID NO:34. In some embodiments, the DNA sequence encoding a self-replicating RNA molecule comprises a fragment of a full-length sequence selected from the group consisting of SEQ ID NO:33 and SEQ ID NO:34 wherein the fragment comprises a contiguous stretch of the nucleic acid sequence of the full-length sequence up to 1, 2, 3, 4, 5, 6, 7, 8, 9, 10, 15, 20, 25, or 30 nucleic acids shorter than full-length sequence.

The nucleic acid-based vaccine may comprise a viral or a non-viral delivery system. The delivery system (also referred to herein as a delivery vehicle) may have adjuvant effects which enhance the immunogenicity of the encoded Zika virus prME antigen. For example, the nucleic acid molecule may be encapsulated in liposomes, non-toxic biodegradable polymeric microparticles or viral replicon particles (VRPs), or complexed with particles of a cationic oil-in-water emulsion. In some embodiments, the nucleic acid-based vaccine comprises a cationic nano-emulsion (CNE) delivery system or a lipid nanoparticle (LNP) delivery system. In some embodiments, the nucleic acid-based vaccine comprises a non-viral delivery system, i.e., the nucleic acid-based vaccine is substantially free of viral capsid. Alternatively, the nucleic acid-based vaccine may comprise viral replicon particles. In other embodiments, the nucleic acid-based vaccine may comprise a naked nucleic acid, such as naked RNA (e.g. mRNA), but delivery via CNEs or LNPs is preferred.

In certain embodiments, the nucleic acid-based vaccine comprises a cationic nano-emulsion (CNE) delivery system. CNE delivery systems and methods for their preparation are described in the following reference: WO2012/006380. In a CNE delivery system, the nucleic acid molecule (e.g. RNA) which encodes the antigen is complexed with a particle of a cationic oil-in-water emulsion. Cationic oil-in-water emulsions can be used to deliver negatively charged molecules, such as an RNA molecule to cells. The emulsion particles comprise an oil core and a cationic lipid. The cationic lipid can interact with the negatively charged molecule thereby anchoring the molecule to the emulsion particles. Further details of useful CNEs can be found in the following references: WO2012/006380; WO2013/006834; and WO2013/006837 (the contents of each of which are incorporated herein in their entirety).

Thus, in a nucleic acid-based vaccine of the invention, an RNA molecule encoding a Zika virus prME antigen may be complexed with a particle of a cationic oil-in-water emulsion. The particles typically comprise an oil core (e.g. a plant oil or squalene) that is in liquid phase at 25° C., a cationic lipid (e.g. phospholipid) and, optionally, a surfactant (e.g. sorbitan trioleate, polysorbate 80); polyethylene glycol can also be included. In some embodiments, the CNE comprises squalene and a cationic lipid, such as 1,2-dioleoyloxy-3-(trimethylammonio)propane (DOTAP). In some preferred embodiments, the delivery system is a non-viral delivery system, such as CNE, and the nucleic acid-based vaccine comprises a self-replicating RNA (mRNA). This may be particularly effective in eliciting humoral and cellular immune responses. Advantages also include the absence of a limiting anti-vector immune response and a lack of risk of genomic integration.

In some embodiments, an RNA molecule encoding a Zika virus prME antigen may be complexed with a submicron cationic oil-in-water emulsion. In some embodiments, the cationic oil-in-water emulsion is characterized by an average particle size of from about 80 nm to 180 nm in diameter (or alternatively from about 80 to about 150 nm; from about 80 to 130 nm; or from about 100 nm). In some embodiments, the concentration of DOTAP in said emulsion, before RNA complexation, is at least about 2.5 mM, or from about 2.5 mM to about 8 mM. In a particular embodiment, the concentration of DOTAP in said emulsion is about 4 mg/ml (5.73 mM). The oil can be squalene or squalane.

In some embodiments, an RNA molecule encoding a Zika virus prME antigen is complexed to a cationic oil-in-water emulsion comprising DOTAP, squalene, sorbitan trioleate and polysorbate 80 in citrate buffer. Cationic oil-in-water emulsions suitable for delivery of an RNA molecule encoding a Zika virus prME antigen may contain about 2 mg/ml to 7 mg/ml DOTAP; about 3 mg/ml to 6 mg/ml Span 85; about 3 mg/ml to 6 mg/ml TWEEN™ 80; and about 30 mg/ml to 50 mg/ml squalene. In certain embodiments, the cationic oil-in-water emulsion, before complexing with RNA, contains about 4.3% w/v squalene, 0.5% TWEEN™ 80, 0.5% SPAN85, and 4 mg/mL DOTAP.

Also provided is a method of preparing a composition comprising an RNA molecule encoding a Zika virus prME antigen complexed to a cationic oil-in-water emulsion, the method comprising: (i) providing an oil-in-water emulsion as described herein; (ii) providing an aqueous solution comprising the RNA molecule; and (iii) combining the aqueous solution of (ii) and the oil-in-water emulsion of (i), thereby preparing the composition. If desired, the aqueous solution comprising the RNA molecule may be a buffer. The buffer may comprise one or more salt, buffer, saccharide, or polymer. In a preferred embodiment, the buffer comprises 560 mM sucrose, 20 mM NaCl, and 10 mM citrate, which can be mixed with a cationic oil in water emulsion described herein to produce a final aqueous phase that comprises 280 mM sucrose, 10 mM NaCl and 10 mM citrate.

LNP delivery systems and non-toxic biodegradable polymeric microparticles, and methods for their preparation are described in the following references: WO2012/006376 (LNP and microparticle delivery systems); Geall et al. (2012) PNAS USA. September 4; 109(36): 14604-9 (LNP delivery system); and WO2012/006359 (microparticle delivery systems). LNPs are non-virion liposome particles in which a nucleic acid molecule (e.g. RNA) can be encapsulated. The particles can include some external RNA (e.g. on the surface of the particles), but at least half of the RNA (and ideally all of it) is encapsulated. Liposomal particles can, for example, be formed of a mixture of zwitterionic, cationic and anionic lipids which can be saturated or unsaturated, for example; DSPC (zwitterionic, saturated), DlinDMA (cationic, unsaturated), and/or DMG (anionic, saturated). Preferred LNPs for use with the invention include an amphiphilic lipid which can form liposomes, optionally in combination with at least one cationic lipid (such as DOTAP, DSDMA, DODMA, DLinDMA, DLenDMA, etc.). A mixture of DSPC, DlinDMA, PEG-DMG and cholesterol is particularly effective. Other useful LNPs are described in the following references: WO2012/006376; WO2012/030901; WO2012/031046; WO2012/031043; WO2012/006378; WO2011/076807; WO2013/033563; WO2013/006825; WO2014/136086; WO2015/095340; WO2015/095346; WO2016/037053. In some embodiments, the LNPs are RVO1 liposomes, see the following references: WO2012/006376 and Geall et al. (2012) PNAS USA. September 4; 109(36): 14604-9.

Pharmaceutical Compositions; Immunogenic Compositions

The disclosure provides compositions comprising a nucleic acid comprising a sequence which encodes a Zika virus polypeptide, for example a Zika virus prME antigen. The composition may be a pharmaceutical composition, e.g., an immunogenic composition or a vaccine composition. Accordingly, the composition may also comprise a pharmaceutically acceptable carrier. In some embodiments, the Zika virus is a Brazilian strain Zika virus.

A "pharmaceutically acceptable carrier" includes any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

Pharmaceutical compositions may include the constructs, nucleic acid sequences, and/or polypeptide sequences described elsewhere herein in plain water (e.g. "w.f.i.") or in a buffer e.g. a phosphate buffer, a Tris buffer, a borate buffer, a succinate buffer, a histidine buffer, or a citrate buffer. Buffer salts will typically be included in the 5-20 mM range. Pharmaceutical compositions may have a pH between 5.0 and 9.5 e.g. between 6.0 and 8.0. Compositions may include sodium salts (e.g. sodium chloride) to give tonicity. A concentration of 10±2 mg/mL NaCl is typical, e.g. about 9 mg/mL. Compositions may include metal ion chelators. These can prolong RNA stability by removing ions which can accelerate phosphodiester hydrolysis. Thus a composition may include one or more of EDTA, EGTA, BAPTA, pentetic acid, etc. Such chelators are typically present at between 10-500 μM e.g. 0.1 mM. A citrate salt, such as sodium citrate, can also act as a chelator, while advantageously also providing buffering activity. Pharmaceutical compositions may have an osmolality of between 200 mOsm/kg and 400 mOsm/kg, e.g. between 240-360 mOsm/kg, or between 290-310 mOsm/kg. Pharmaceutical compositions may include one or more preservatives, such as thiomersal or 2-phenoxyethanol. Mercury-free compositions are preferred, and preservative-free vaccines can be prepared. Pharmaceutical compositions may be aseptic or sterile. Pharmaceutical compositions may be non-pyrogenic e.g. containing <1 EU (endotoxin unit, a standard measure) per dose, and preferably <0.1 EU per dose. Pharmaceutical compositions may be gluten free. Pharmaceutical compositions may be prepared in unit dose form. In some embodiments, a unit dose may have a volume of between 0.1-1.0 mL e.g. about 0.5 mL.

In some embodiments, the compositions disclosed herein are immunogenic composition that, when administered to a subject, induce a humoral and/or cellular antigen-specific immune response (i.e. an immune response which specifically recognizes a naturally occurring Zika virus polypeptide). For example, an immunogenic composition may induce a memory T and/or B cell population relative to an untreated subject following Zika virus infection, particularly in those embodiments where the composition comprises a nucleic acid comprising a sequence which encodes a Zika virus prME antigen or comprises a Zika virus antigen. In some embodiments, the subject is a vertebrate, such as a mammal e.g. a human or a veterinary mammal.

The compositions of the invention can be formulated as vaccine compositions. The vaccine will comprise an immunologically effective amount of antigen. By "an immunologically effective amount" is intended that the administration of that amount to a subject, either in a single dose or as part of a series, is effective for inducing a measurable immune response against Zika virus in the subject. This amount varies depending upon the health and physical condition of the individual to be treated, age, the taxonomic group of individual to be treated (e.g. human, non-human primate, etc.), the capacity of the individual's immune system to synthesize antibodies, the degree of protection desired, the formulation of the composition or vaccine, the treating doctor's assessment of the medical situation, the severity of the disease, the potency of the compound administered, the mode of administration, and other relevant factors. It is expected that the amount will fall in a relatively broad range that can be determined through routine trials. Vaccines as disclosed herein may either be prophylactic (i.e. to prevent infection) or therapeutic (i.e. to treat infection), but will typically be prophylactic. In some embodiments, the vaccine compositions disclosed herein may induce an effective immune response against a Zika virus infection, i.e., a response sufficient for treatment or prevention of a Zika virus infection.

In some embodiments, the composition further comprises an additional antigen. In some embodiments, the composition is administered to a subject in combination with a further composition which comprises an additional antigen.

A composition of the present disclosure may also comprise, or be administered in conjunction with, one or more adjuvants (e.g. vaccine adjuvants), in particular where the composition comprises an immunologically effective amount of a nucleic acid encoding a Zika virus prME antigen or a Zika virus prME antigen. By adjuvant is intended that is capable of increasing an immune response against an antigen compared to administration of said antigen alone. In some aspects, adjuvant compositions as disclosed herein further comprise one or more immunostimulants, for example, a saponin such as QS21.

Adjuvants which may be used in compositions of the invention include, but are not limited to: (A) Mineral-containing compositions, for example aluminum and calcium salts, such as aluminum phosphates. (B) Oil emulsions, for example squalene-in-water emulsions, such as MF59 or AS03. Complete Freund's adjuvant (CFA) and incomplete Freund's adjuvant (IF A) may also be used. (C) Saponin formulations. (D) Virosomes and virus-like particles (VLPs). (E) Bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. (F) Human immunomodulators, for example cytokines, such as interleukins, interferons, macrophage colony stimulating factor, and tumor necrosis factor. (G) Bioadhesives and mucoadhesives, such as esterified hyaluronic acid microspheres, cross-linked derivatives of poly(acrylic acid), polyvinyl alcohol, polyvinyl pyrollidone, polysaccharides and carboxymethylcellulose. (H) Microparticles, for example particles of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(a-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB). (I) Liposomes. (J) Polyoxyethylene ether and polyoxyethylene ester formulations. (K) Polyphosphazene (PCPP). (L) Muramyl peptides. (M) Imidazoquinolone compounds, for example Imiquamod and its homologues.

Combinations of one or more of the adjuvants identified above may also be used with the invention.

Methods of Use/Uses

In some embodiments are provided methods for inducing an immune response against a Zika virus infection in a subject in need thereof comprising a step of administering an immunologically effective amount of a construct or composition as disclosed herein. In some embodiments are provided the use of the constructs or compositions disclosed herein for inducing an immune response to a Zika virus prME antigen in a subject in need thereof. In some embodiments are provided the use of the constructs or compositions disclosed herein for inducing an immune response against a Zika virus infection in a subject. In some embodiments are provided use of the construct or composition as disclosed herein in the manufacture of a medicament that induces an immune response to a Zika virus infection in a subject. By "subject" is intended a vertebrate, such as a mammal e.g. a human or a veterinary mammal. In some embodiments, the subject is human. By "immune response" is intended a humoral and/or cellular antigen-specific immunological response (i.e. an immune response which specifically recognizes an antigen polypeptide) that can be demonstrated to neutralize Zika virus in vitro or control/reduce/eliminate Zika virus infection in vivo.

In some embodiments, the immune response is characterized by immunological memory against the Zika virus and/or an effective Zika virus-responsive memory T cell population.

In some embodiments the composition comprises an RNA molecule encoding a polypeptide selected from the group consisting of SEQ ID NO:19 and SEQ ID NO:24.

In some embodiments, the composition comprises an RNA molecule encoding a polypeptide which is at least 70%, at least 75%, at least 80%, at least 85%, at least 90%, at least 95%, at least 96%, at least 97%, at least 98%, or at least 99% identical to a sequence selected from the group consisting of SEQ ID NO:19 and SEQ ID NO:24. In some embodiments, the composition comprises an RNA molecule encoding a polypeptide which comprises a fragment of a full-length sequence selected from the group consisting of SEQ ID NO:19 and SEQ ID NO:24, wherein the fragment comprises a contiguous stretch of the amino acid sequence of the full-length sequence up to 1, 2, 3, 4, 5, 6, 7, 8, 9, or 10 amino acids shorter than full-length sequence.

In some embodiments is provided a construct, a vector, a self-replicating RNA and/or molecule as described herein for use in therapy or medicine. In some embodiments, the compositions disclosed herein are for use in therapy or medicine. In preferred embodiment, the therapy is a vaccine therapy. Preferably the therapy is vaccine to prevent Zika virus infection.

In some embodiments is provided a construct, a vector, a self-replicating RNA and/or molecule as described herein for use in preventing or treating Zika virus infection in a subject in need thereof.

In some embodiments, the compositions disclosed herein are for use in preventing or treating Zika virus infection in a subject in need thereof.

In some embodiments, the compositions disclosed herein are for use in inducing an immune response against a Zika virus infection in a subject in need thereof.

In some embodiments is provided a construct, a vector, a self-replicating RNA molecule, and/or a composition as described herein for use in a method of inducing an immune response to a Zika virus infection in a subject in need thereof.

In some embodiments, methods are provided for preventing or shortening Zika virus infection and/or reducing or preventing the clinical symptoms upon Zika virus infection in a subject in need thereof, which comprises administering to said subject an immunologically effective amount of an immunogenic composition as provided herein.

In some embodiments is provided use of a construct or composition disclosed herein in the manufacture of an immunogenic composition for preventing or shortening Zika virus infection in a subject and/or reducing or prevent the clinical symptoms upon Zika virus infection in a subject.

In some embodiments, methods are provided for preventing or reducing transmission of a Zika virus infection from one subject to another. In specific embodiments, methods are provided for preventing or reducing transmission of a Zika virus infection to a fetus across the placental barrier. In some embodiments, a composition as described herein is administered to a woman in an amount effective to prevent transmission of a Zika virus infection across the placental barrier.

In some embodiments is provided use of a construct or composition disclosed herein in the manufacture of an immunogenic composition for preventing or reducing transmission of a Zika virus infection to a fetus across the placental barrier.

In some embodiments is provided a construct, a vector, a self-replicating RNA molecule, and/or a composition as described herein for use in a method of preventing or reducing transmission of a Zika virus infection to a fetus across the placental barrier.

In some embodiments, the subject is a human subject. In specific embodiments, the human subject has been exposed, or is at risk of being exposed, to a Zika virus infection.

Routes of Administration/Dosages

Compositions disclosed herein will generally be administered directly to a subject. Direct delivery may be accomplished by parenteral injection {e.g. subcutaneously, intraperitoneally, intravenously, intramuscularly, intradermally, or to the interstitial space of a tissue). Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical human intramuscular dose volume is 0.5 ml.

A dose of a nucleic acid (e.g. a nucleic acid-based vaccine, such as a Zika SAM vaccine) may have about 50 μg to about 100 μg nucleic acid. In one embodiment, a Zika SAM vaccine dose contains 50, 55, 60, 65, 70, 75, 80, 85, 90, 95 or 100 μg RNA. In other embodiments, a dose of a Zika SAM vaccine may have <10 μg nucleic acid; e.g. from 1-10 μg, such as about 1 μg, 2.5 μg, 5 μg, 7.5 μg or 10 μg, but expression can be seen at much lower levels; e.g. using <1 μg/dose, <100 ng/dose, <10 ng/dose, <1 ng/dose, etc. Similarly, a dose of a protein antigen may have <10 μg protein; e.g. from 1-10 μg, such as about 1 μg, 2.5 μg, 5 μg, 7.5 μg or 10 μg.

In preferred embodiments, a Zika SAM vaccine or vaccine composition is administered to a subject at an effective dose, meaning a dose sufficient to achieve a desired immune response, such as induction of neutralizing antibodies to Zika virus and/or protection against Zika virus infection.

In some embodiments, a Zika SAM vaccine described herein has an effective dose that is less than or equal to 50%, 40%, 30%, 20% or 10% of the effective dose of a DNA vaccine or vaccine composition encoding the same antigen. In some embodiments, a Zika SAM vaccine described herein has an effective dose that is one third or less of the effective dose of a DNA vaccine or vaccine composition encoding the same antigen.

Processes of Manufacture/Formulation

Processes for the manufacture of self-replicating RNA are provided herein. In some embodiments, the process of manufacturing a self-replicating RNA comprises a step of in vitro transcription (IVT) as described elsewhere herein. In some embodiments, the process of manufacturing a self-replicating RNA comprises a step of IVT to produce a RNA, and further comprises a step of combining the RNA with a non-viral delivery system as described elsewhere herein. In some embodiments, the process of manufacturing a self-replicating RNA comprises a step of IVT to produce a RNA, and further comprises a step of combining the RNA with a CNE delivery system as described elsewhere herein.

Sequence Identity

Identity or homology with respect to an amino acid sequence is defined herein as the percentage of amino acid residues in the candidate sequence that are identical with the reference amino acid sequence after aligning the sequences and introducing gaps, if necessary, to achieve the maximum percent sequence identity, and not considering any conservative substitutions as part of the sequence identity. Identity or homology with respect to a nucleic acid sequence is defined herein as the percentage of nucleotides in the candidate sequence that are identical with the reference nucleic acid sequence after aligning the sequences and introducing gaps, if necessary, to achieve the maximum percent sequence identity.

Sequence identity can be determined by standard methods that are commonly used to compare the similarity in position of the amino acids of two polypeptides. Using a computer program such as BLAST, two polypeptides are aligned for optimal matching of their respective amino acids (either along the full length of one or both sequences or along a pre-determined portion of one or both sequences). The programs provide a default opening penalty and a default gap penalty, and a scoring matrix such as PAM 250 [a standard scoring matrix; see Dayhoff et al., in Atlas of Protein Sequence and Structure, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the shorter sequences in order to align the two sequences. The same methods used to compare polypeptides can also be used to calculate the percent identity of two polynucleotide sequences.

Where the present disclosure refers to a sequence by reference to a UniProt or Genbank accession code, the sequence referred to is the current version at the filing date of the present application.

General

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "plurality" refers to two or more. Additionally, numerical limitations given with respect to concentrations or levels of a substance, such as solution component concentrations or ratios thereof, and reaction conditions such as temperatures, pressures and cycle times are intended to be approximate. The term "about" used herein is intended to mean the amount ±10%.

The term "comprises" means "includes." Thus, unless the context requires otherwise, the word "comprises," and variations such as "comprise" and "comprising" will be understood to imply the inclusion of a stated compound or composition (e.g., nucleic acid, polypeptide, antigen) or step, or group of compounds or steps, but not to the exclusion of any other compounds, composition, steps, or groups thereof. Embodiments described as comprising certain components are intended to include embodiments consisting of the indicated components.

The abbreviation, "e.g." is derived from the Latin exempli gratia, and is used herein to indicate a non-limiting example. Thus, the abbreviation "e.g." is synonymous with the term "for example."

The invention will be further described by reference to the following, non-limiting, figures and examples.

EXAMPLES

Example 1. Project Summary

The present inventors initiated work on a Zika vaccine using the SAM platform—synthetic, self-amplifying mRNA (SAM) derived from the alphavirus genome, expressing antigens of interest. The SAM constructs are evaluated for robust antigen production and antigenicity and further tested for their immunogenicity and efficacy using in vivo models.

Methods

The SAM vector VEE TC-83 was used as the background construct for cloning in the Examples. See SEQ ID NO:17.

Example 2. Selection of Antigen

The *Flavivirus* genome consists of capped single-stranded RNA of positive polarity of approximately 11.3 kb in length (FIG. 1). The 5' proximal quarter of the genome encodes the structural proteins capsid (C), pre-membrane (prM), and envelope (E). The nonstructural proteins NS1, NS2A, NS2B, NS3, NS4A, NS4B, and NS5 are involved in viral RNA replication. The coding region is flanked by 5' and 3' untranslated regions (5' and 3' UTRs) of approximately 100 and 600 nucleotides in length, respectively. Translation of the viral genome yields a single polypeptide that is processed into the individual proteins by a combination of cellular proteases and a viral protease consisting of a catalytic subunit, NS3, and its cofactor, NS2B.

The structural proteins prM and E are cotranslationally inserted into the endoplasmic reticulum (ER) membrane and processed by signal peptidases, producing proteins that encapsidate C together with the viral RNA, by budding into the ER lumen (FIG. 2). At a later step in viral maturation, prM on these particles is cleaved into mature M protein by a cellular furin protease prior to release from the cell. This prM cleavage is required for infectivity of the released virions. In addition to infectious virions, *Flavivirus*-infected cells release sub-viral particles (SVPs) (FIG. 2). These particles are smaller than virions, but contain the antigenically important E protein and the prM/M protein, which is essential for correct folding and incorporation of the E protein into SVPs and viral particles. However, unlike virions, SVPs do not contain either the C protein or the viral genome, and are thus non-infectious. SVPs can be produced in a variety of systems by co-expression of the prM and E proteins, and SVPs share properties with wild-type viruses, such as fusogenic activity and induction of a neutralizing immune response and have repeatedly been shown to stimulate protective immune responses against a number of *Flavivirus* diseases. The present inventors selected structural proteins of Zika virus, namely-prM and E, for further experimentation.

Example 3. Strain Selection

The amino acid sequences of the C-prME proteins from Zika virus strains (available from NCBI/Genbank) from Zika outbreaks around the world from 2007 onwards were aligned to look for similarities and differences (FIG. 3). These included the original African lineage strain from Uganda, Micronesia (2007), French Polynesia (2013), and the Brazilian strains from 2016 (FIG. 3). In addition, seven strains of Zika virus from various regions in Brazil, were also compared for amino acid differences in the C-prME region (FIG. 4). A high conservation was observed across the strains from different outbreaks, with the Brazilian strains almost identical in the CprME region. The Natal, Bahia strain (KU527068) was chosen as the representative strain. KU527068 was one of the first strains to be isolated from the brain of a fetus showing microcephaly.

Example 4. Design of Constructs

The design of Zika-SAM constructs of FIG. 6 includes cloning the sequence encoding the Zika virus (Natal, Brazil strain) structural pre-membrane (prM) and envelope (E) proteins under the subgenomic promoter in a SAM vector. A series of modifications to the SAM-prME constructs were made (Table 1, FIG. 6). These include:

i. Substitution of the native prM signal peptide with the JEV signal peptide (FIG. 6A-B, antigen inserts #5283 and #5288).

ii. Substitution of the native C-terminus of Zika E protein with the C-terminus of JEV E protein (FIG. 6B, antigen insert #5288).

iii. Truncation of the wild-type Zika prM start sequence to impair expression and secretion of the prME antigen (antigen insert #4974). Antigen insert #4974 was used as a negative control. The amino acid sequence of antigen insert #4974 is shown in SEQ ID NO:29, including the JEV signal sequence (SEQ ID NO:5), followed by a truncated Zika pr region (SEQ ID NO:30), Zika M protein (SEQ ID NO:31) and Zika E protein (SEQ ID NO:32). The DNA and RNA sequences encoding antigen insert #4974 are presented in SEQ ID NOs:28 and 41, respectively.

iv. A non-Zika antigen construct, #8111, was designed and used as a positive control.

Evaluation/Study Design

The constructs are evaluated in mammalian cells following electroporation of Zika-SAM RNA into BHK cells using the following methods:

a. SAM RNA replication-potency of the SAM-Zika constructs is tested by using antibodies against dsRNA and FACS.

b. Antigen expression is determined by immunoblots and immunofluorescence assays, to investigate cleaved prM and E protein in cell lysates and cell supernatant.

c. The production of SVPs is tested in mammalian cells by using established procedures for SVP isolation from cell supernatant.

Following identification of the most efficient candidate constructs formulation into LNP/CNE based-delivery systems is carried out and testing for antigenicity and immunogenicity is carried out in vivo.

Example 5. Expression and Secretion of Zika-SAM Constructs

The ability of cells to express and secrete Zika E protein and hybrid Zika-JEV E protein from the Zika-SAM constructs described above was evaluated according to the following methods.

On Day 0, BHK cells were plated at $8\times10^6$ in T225 flasks in Growth Media. For trypsinization, media was removed and cells were washed with 5 mls of PBS. The PBS wash was removed, and 5 mls of pre-warmed trypsin was added and spread thoroughly across the plate. Trypsin was removed and plates were kept at 37 deg C. for 1-2 mins. Cells were then resuspended in 10 mls of growth media (5% FBS). Cells were counted and plated at required concentration into a new flask. The cells were then incubated at 37 deg C., 5% $CO_2$ for about 20 hours.

On Day 1, plates were prepared by adding 2 ml DMEM+1% FBS+P/S (outgrowth media) to each well of a 6-well plate (one well per electroporation). Plates were kept warm in a 37 deg C. incubator. The electroporator was prepared to deliver 120V, 25 ms pulse, 0.0 pulse interval, 1 pulse for a 2 mm cuvette. Cuvettes were labeled and kept on ice. Cells in growth phase were harvested as normal into BHK media (growth) and counted using a hemocytometer. Cells were trypsinized following the same trypsinization protocol as above. Standards and negative control electroporations were also prepared.

Cells were centrifuged at 1500 rpm (462×g) for 5 mins. Media was aspirated, and cells were washed once with 20 ml cold Opti-MEM media. Cells were again centrifuged at 1500 rpm (462× g) for 5 mins. Media was aspirated, and the cells were resuspended in Opti-MEM media to 0.25 ml per electroporation.

For each sample, 4000 ng of RNA was mixed with 250 ul cells, and the mixture was pipetted gently 4-5 times. The cells and RNA mixture were transferred to 2 mm cuvettes and subjected to one pulse of electroporation using the parameters described above. Cells were allowed to rest at room temperature for 10 mins. Cells from one cuvette were added to one well of a pre-warmed 6-well plate, and the plate was tipped front and back and then side to side at a 45° angle to distribute cells evenly.

On Day 2 (30 h post-electroporation), the supernatant was collected. An aliquot of 75 ul was removed for Western blot, 25 ul 4× NuPAGE buffer was added to the aliquot (no reducing agent), and the aliquot was stored at −20 deg C. The rest of the supernatant was stored at −80 deg C.

Cells were washed once with ice cold PBS, and then scraped into 200 ul of RIPA buffer containing protease inhibitor cocktail (1 tablet in 10 ml) while keeping the plate on ice. The buffer containing cells was collected in microcentrifuge tubes, and subjected to two rounds of freeze thawing on dry ice. Samples were vortexed briefly, and pelleted at 8000 rpm for 5 min. Pellets were discarded and the supernatants were retained. 25 ul 4× NuPAGE buffer was added to a 75 ul aliquot of the lysates for Western blotting. Aliquots were stored at −20 deg C. The rest of the lysates were stored at −80 deg C.

Immunoblotting 15 ul of the cell culture supernatants and 15 ul of the cell lysates were run on a 4-12% SDS PAGE gel (Bis-Tris) in 1×MOPS running buffer. The separated samples were transferred onto nitrocellulose membranes. Membranes were blocked for 2-3 hours in PBS-Tween 20 ±5% milk. The *Flavivirus* 4G2 primary antibody was added at 1:120 dilution in PBS-T-Milk and membranes were incubated overnight at 4 deg C. Membranes were then washed 3 times for 10 minutes each in PBS-T. Anti-mouse secondary (Odyssey® anti-Mouse 800CW-green (LI-COR, Inc., Lincoln, Nebr.) at 1:5000) in LI-COR blocking buffer was then added, and the membranes were incubated for 1 hour. Membranes were washed three times for 2 minutes each, and then scanned on LI-COR Odyssey® imager (LI-COR, Inc., Lincoln, Nebr.) at 800 channel, medium intensity.

Results

Zika E protein expression and secretion was detectable by immunoblot in lysates from cells electroporated with Zika-SAM constructs #5283 (JEV signal+wild type Zika prME), #5288 (JEV signal+hybrid Zika-JEV prME) and #8111 (positive control antigen). (FIG. 7). Expression and secretion of Zika E protein were not detected in the N-terminally truncated construct (#4974) or Mock controls.

Example 6: Cationic Oil-in-Water Emulsions

Cationic nanoemulsions (CNEs) were prepared essentially according to the methods described in Brito et al., Molecular Therapy, Vol. 22, No. 12, pp. 2118-29 (2014) and International Patent Publication WO2013006834.

Briefly, squalene (Sigma, St. Louis, Mo.) was heated to 37° C., and DOTAP (Lipoid, Ludwigshafen Germany) was dissolved directly in squalene in the presence of sorbitan trioleate (SPAN 85; Sigma, St. Louis, Mo.). The resulting oil phase was then combined with the aqueous phase (TWEEN™; Sigma, St. Louis, Mo., in citrate buffer) and immediately homogenized for 2 min using an T25 homogenizer (IKA, Wilmington, N.C.) at 24K RPM to produce a primary emulsion. The primary emulsions were passed three to five times through a M-110S Microfluidizer or a M-110P Microfluidizer (Microfluidics, Newton, Mass.) with an ice bath cooling coil at a homogenization pressure of approximately 15K-20K PSI. The batch samples were removed from the unit and stored at 4° C. The CNE formulation used in the present examples contains 4 mg/ml DOTAP; 4.7 mg/ml Span 85; 4.7 mg/ml TWEEN™; and 39 mg/ml squalene.

Example 7. Preparation of RNA-CNE Complexes

1. RNA Synthesis

Zika SAM constructs contain a bacteriophage T7 promoter located upstream of the alphavirus cDNA to facilitate the synthesis of the replicon RNA in vitro. SAM-Zika RNA for constructs #5283 (encoding JEV signal+Zika prME) and #5288 (encoding JEV signal+hybrid Zika-JEV prME), as well as negative control construct #4974, were synthesized using standard molecular biology techniques. Briefly, plasmid DNA encoding Zika-SAM constructs were linearized by endonuclease digestion a unique site located at the 3' end of the replicon sequence. The linearized DNA was then transcribed into RNA by in vitro synthesis using a T7 RNA polymerase in the presence of the template DNA and nucleoside triphosphates (ATP, CTP, GTP and UTP). Following transcription, DNA template was digested with DNase, and the RNA transcripts were purified by LiCl precipitation and reconstituted in nuclease-free water. RNA was then capped using the Vaccinia Capping System (New England BioLabs, Ipswich, Mass.) and purified by LiCl precipitation. RNA concentration in each reaction was determined by spectrophotometry. Prior to RNA complexation, RNA was diluted to a concentration of 300 μg/ml in citrate buffer (10 mM citrate pH 6.2, 20 mM NaCl, 560 mM sucrose).

2. RNA Complexation

Zika SAM RNA was complexed with cationic nanoemulsion (CNE) particles essentially as described in Brito et al., Molecular Therapy, Vol. 22, No. 12, pp. 2118-29 (2014). Briefly, Zika SAM RNA (300 μg/ml in citrate buffer) was added to an equal volume of the CNE produced in Example 6, mixed, and allowed to complex on ice for 30 minutes to 2 hours. The final concentration of CNE-complexed RNA was 150 μg/ml.

The ratio of RNA to cationic lipid can be expressed as an N/P ratio, defined as the amount (moles) of protonatable nitrogen (N) atoms in the cationic lipid divided by the amount (moles) of phosphates (P) on the RNA. DOTAP for example has one nitrogen that can be protonated per molecule. The RNA concentration was used to calculate the amount of phosphate in solution using an estimate of 3 nmols of phosphate per microgram of RNA. The CNE formulations described above have an N/P ratio of 6.3:1.

Example 8. In Vivo Immunogenicity and Protection of Zika SAM CNE Formulations Immunogenicity and protection of Zika SAM CNE formulations were examined in mice and non-human primates (NHP).

I. Mouse Study

Female BALB/c mice (6-12 weeks old; The Jackson Laboratory), were housed and bred in the animal facility of the Vaccine Research Center, NIAID, NIH, Bethesda, Md. All animal experiments were reviewed and approved by the Animal Care and Use Committee of the VRC, NIAID, NIH. All animals were housed and cared for in accordance with local, state, federal, and institutional policies in an American Association for Accreditation of Laboratory Animal Care-accredited facility at the NIH.

Mice were immunized twice according to the study design shown in Table 2. Briefly, groups of 10 mice each were administered CNE formulations containing the Zika SAM RNA constructs #5288 or #5283, or the negative control RNA construct #4974. Another group of mice received 50 μg of a DNA vaccine encoding construct #5283 by intramuscular electroporation, as a positive control. See Dowd et al., Science, Vol. 354 Issue 6309, pp. 237-40 (2016). All mice were challenged by intraperitoneal (i.p.) injection of live Zika virus on day 49.

TABLE 2

Mouse study design

| Group | n | Delivery | Construct | Immunization Day 0 | Immunization Day 21 | Challenge Day 49 |
|---|---|---|---|---|---|---|
| 1 | 10 | CNE56/RNA | 4974 | 1.5 μg | 1.5 μg | 100 PFU, IP |
| 2 | 10 | CNE56/RNA | 5288 | 1.5 μg | 1.5 μg | 100 PFU, IP |
| 3 | 10 | CNE56/RNA | 5283 | 15 μg | 15 μg | 100 PFU, IP |
| 4 | 10 | CNE56/RNA | 5283 | 1.5 μg | 1.5 μg | 100 PFU, IP |
| 5 | 10 | Electroporation/ DNA | 5283 | 50 μg | 50 μg | 100 PFU, IP |

Blood sera were collected on day 0, as well as 2 weeks after the first immunization, 2 weeks after the second immunization, and three days after the Zika virus challenge.

Zika neutralizing antibody titers were measured by reporter virus particle (RVP) neutralization assay according to methods described in Dowd, K A et al. Cell Rep. 16(6):1485-9 (2016). Results are shown in FIG. 8. Two weeks after the first immunization with Zika SAM construct #5283, or the positive control DNA construct, there were significant levels of Zika neutralizing antibodies detected in the sera of immunized mice. Zika neutralizing antibody levels were even higher two weeks after the second immunization with the SAM construct #5283 or the positive control DNA construct.

A dose-dependent effect was observed, with the 15 μg dose of Zika SAM construct #5283 producing higher levels of neutralizing antibodies than the 1.5 μg dose. Notably, the 15 μg dose of Zika SAM construct #5283 produced a neutralizing antibody response that was comparable to the 50 μg dose of the DNA format of the same vaccine construct (DNA #5283). These results indicate that Zika SAM construct #5283 is capable of inducing a significant neutralizing antibody response to Zika virus.

On day 49 of the study, mice were challenged with intraperitoneal injections of live Zika virus (strain PRV-ABC57) at a dose of 100 plaque forming units (PFU). Serum samples were taken three days after challenge, and viral loads were determined by real time quantitative PCR (qPCR) of the Zika virus capsid gene.

As shown in FIG. 9, mice vaccinated with Zika SAM construct #5283 (1.5 or 15 μg doses) or the positive control construct (DNA #5283) showed little or no detectable Zika virus in the serum. In contrast, significant Zika viral load was detected in unvaccinated animals, as well as in animals vaccinated with Zika SAM construct 5288 or negative control construct #4974. These results indicate that Zika SAM construct #5283 is capable of generating a protective immune response against Zika virus infection.

II. Non-Human Primate (NHP) Study

Immunogenicity of Zika SAM constructs was evaluated in non-human primates (NHPs). Rhesus macaques were immunized twice according to the study design shown in Table 3. Briefly, SAM-Zika RNA-CNE formulations were prepared as described in Example 7. Groups of 8 NHPs each were administered either placebo (phosphate buffered saline) or a CNE formulation containing a codon-optimized SAM construct, Co.prME, encoding the native Zika prME antigen (Group 2, 75 ug×2; as described in PCT/162017/053242, filed Jun. 1, 2017); or Zika SAM construct #5283 (Group 3; 75 ug×2). Another group of NHPs (Group 4; n=8) received two immunizations (4 mg each) of a DNA vaccine encoding construct #5283 intramuscularly by a needle-free injection device (PharmaJet), as a positive control. See Dowd et al., Science, Vol. 354 Issue 6309, pp. 237-40 (2016). All animals were challenged by intraperitoneal (i.p.) injection of live Zika virus (1000 PFU) 8 weeks after the first immunization.

TABLE 3

| Group | Vaccine | Group size | Week 0 Vaccination | Week 4 Boost | Week 8 Challenge |
|---|---|---|---|---|---|
| 1 | Placebo | 8 | PBS | PBS | 1000 PFU ZIKV |
| 2 | Co.prME SAM | 8 | 75 μg | 75 μg | 1000 PFU ZIKV |
| 3 | SAM #5283 | 8 | 75 μg | 75 μg | 1000 PFU ZIKV |
| 4 | DNA #5283 | 8 | 4 mg | 4 mg | 1000 PFU ZIKV |

Blood sera were collected on day 0, as well as 4 and 8 weeks after the first immunization; at each of days 3-7 after the Zika virus challenge; and at weeks 8, 10 and 12 after Zika virus challenge. Zika neutralizing antibody titers were measured by reporter virus particle (RVP) neutralization assay according to methods described in Dowd, K A et al. Cell Rep. 16(6):1485-9 (2016).

The immunogenicity results shown in FIG. 10 demonstrate that Zika neutralizing antibodies were significantly elevated four weeks after the first immunization of Zika SAM construct #5283 as compared to placebo, with titers being further increased 4 weeks after the second immunization. Zika DNA #5283 elicited similar neutralizing antibody titers at 4 and 8 weeks. Zika-SAM construct Co.prME SAM produced significantly less neutralizing antibodies compared to DNA #5283 after a single dose, but similar titers after two injections.

In week 8 of the study, NHPs were challenged with intraperitoneal injections of live Zika virus (strain PRV-ABC57) at a dose of 1000 plaque forming units (PFU). Viral loads after challenge were determined by real time quantitative PCR (qPCR) of the Zika virus capsid gene.

As shown in FIG. 11, placebo animals exhibited elevated viremia as early as 3 days post-challenge (A). Vaccination with Zika-SAM construct #5283 (B), as well as positive controls Zika-SAM Co.prME (C) and DNA #5283 (D), were protective against Zika viremia, with Zika-SAM construct #5283 exhibiting a complete protection against Zika viremia.

Consistent with the viremia results, placebo animals showed a sharp rise in neutralizing antibodies after Zika challenge, further confirming Zika infection in these animals (FIG. 12). Two animals in the SAM Co.prME group, and one animal in the DNA #5283 group, also showed elevated neutralizing antibody titers post-challenge, indicating that protection was not sterilizing in these animals. In contrast, animals in the Zika SAM #5283 group did not exhibit elevated neutralizing antibodies after Zika challenge, indicating that sterilizing protection was achieved in all subjects.

We claim:

1. A self-replicating RNA molecule encoding (i) a polypeptide comprising a Zika virus prME antigen which comprises amino acids 21 through 692 of SEQ ID NO: 2 or a polypeptide which comprises a region that is at least 90% identical to the amino sequence of SEQ ID NO:2 or an immunogenic fragment thereof comprising a contiguous amino acid sequence of at least 8 amino acids which is identical to a contiguous amino acids sequence of the full-length Zika virus prME antigen and (ii) a Japanese Encephalitis Virus (JEV) signal sequence comprising SEQ ID NO:5 or a sequence with at least 90% sequence identity to SEQ ID NO:5.

2. The self-replicating RNA molecule of claim 1 which comprises a nucleic acid sequence selected from the group consisting of:

a. a nucleic acid sequence encoding a polypeptide comprising the amino acid sequence of SEQ ID NO:19 or SEQ ID NO:24;
b. a nucleic acid sequence comprising the RNA sequence of SEQ ID NO:39 or SEQ ID NO:40; and
c. a nucleic acid sequence comprising the RNA sequence of SEQ ID NO:36 or SEQ ID NO:37.

3. A DNA molecule encoding the self-replicating RNA molecule of claim 1.

4. A composition comprising an immunologically effective amount of the self-replicating RNA molecule of claim 1.

5. The composition of claim 4, wherein the composition comprises a non-viral delivery material, selected from a submicron cationic oil-in-water emulsion; a liposome; or a biodegradable polymeric microparticle delivery system.

6. The composition of claim 5, wherein the submicron cationic oil-in-water emulsion comprises an oil core, a cationic lipid, and a surfactant.

7. The composition of claim 4 wherein the composition further comprises one or more nucleic acid sequences which encode one or more additional antigens and/or the composition further comprises one or more additional antigens.

8. The composition of claim 4 wherein the composition comprises one or more adjuvants.

9. A method of inducing an immune response against a Zika virus infection in a subject in need thereof, which comprises administering to said subject an immunologically effective amount of a self-replicating RNA molecule of claim 1.

10. A method of inducing an immune response against a Zika virus infection in a subject in need thereof, which comprises administering to said subject an immunologically effective amount of the composition of claim 5.

11. The method of claim 10 wherein the subject is human.

12. A process for producing an RNA-based vaccine comprising a step of transcribing a DNA that encodes the self-replicating RNA molecule of claim 1 to produce said self-replicating RNA molecule.

13. The process of claim 12, wherein said transcription is in vitro.

14. The process of claim 12, further comprising a step of formulating the self-replicating RNA with a non-viral delivery system.

15. The process of claim 14, wherein the delivery system is selected from the group consisting of: a submicron cationic oil-in-water emulsion; a liposome; and a biodegradable polymeric microparticle delivery system.

16. The process of claim 12, further comprising a step of combining the self-replicating RNA with an additional composition comprising an adjuvant.

17. The process of claim 16, wherein said adjuvant comprises an immunostimulant.

18. The composition of claim 4, which induces sterilizing immunity in Rhesus macaques.

19. The composition of claim 4, which produces a 4-fold change in neutralizing titers when inoculated into Rhesus macaques.

* * * * *

SEQUENCE LISTING

<160> NUMBER OF SEQ ID NOS: 41

<210> SEQ ID NO 1
<211> LENGTH: 2079
<212> TYPE: DNA
<213> ORGANISM: Zika virus

<400> SEQUENCE: 1
atgcgaggcg cagatactag tgtcggaatt gttggcctcc tgctgaccac agctatggca 60
gcggaggtca ctagacgtgg gagtgcatac tatatgtact tggacagaaa cgatgctggg 120
gaggccatat cttttccaac cacattgggg atgaataagt gttatataca gatcatggat 180
cttggacaca tgtgtgatgc caccatgagc tatgaatgcc ctatgctgga tgagggggtg 240
gaaccagatg acgtcgattg ttggtgcaac acgacgtcaa cttgggttgt gtacggaacc 300
tgccatcaca aaaaaggtga agcacggaga tctaggagag ctgtgacgct cccctcccat 360
tccactagga agctgcaaac gcggtcgcaa acctggttgg aatcaagaga atacacaaag 420
cacttgatta gagtcgaaaa ttggatattc aggaaccctg gcttcgcgtt agcagcagct 480
gccatcgctt ggcttttggg aagctcaacg agccaaaaag tcatatactt ggtcatgata 540
ctgctgattg ccccggcata cagcatcagg tgcataggag tcagcaatag ggactttgtg 600
gaaggtatgt caggtgggac ttgggttgat gttgtcttgg aacatggagg ttgtgtcacc 660
gtaatggcac aggacaaacc gactgtcgac atagagctgg ttacaacaac agtcagcaac 720
atggcggagg taagatccta ctgctatgag gcatcaatat cagacatggc ttcggacagc 780
cgctgcccaa cacaaggtga agcctacctt gacaagcaat cagacactca atatgtctgc 840
aaaagaacgt tagtggacag aggctgggga aatggatgtg gactttttgg caaagggagc 900
ctggtgacat gcgctaagtt tgcatgctcc aagaaaatga ccgggaaaag catccagcca 960
gagaatctgg agtaccggat aatgctgtca gttcatggct cccagcacag tgggatgatc 1020
gttaatgaca caggacatga aactgatgag aatagagcga aggttgagat aacgcccaat 1080
tcaccaagag ccgaagccac cctggggggt tttggaagcc taggacttga ttgtgaaccg 1140
aggacaggcc ttgacttttc agatttgtat tacttgacta tgaataacaa gcactggttg 1200
gtccacaagg agtggttcca cgacattcca ttaccttggc acgctggggc agacaccgga 1260
actccacact ggaacaacaa agaagcactg gtagagttca aggacgcaca tgccaaaagg 1320
caaactgtcg tggttctagg gagtcaagaa ggagcagttc acacggccct tgctggagct 1380
ctggaggctg agatggatgg tgcaaaggga aggctgtcct ctggccactt gaaatgtcgc 1440
ctgaaaatgg ataaacttag attgaagggc gtgtcatact ccttgtgtac cgcagcgttc 1500
acattcacca agatcccggc tgaaacactg cacgggacag tcacagtgga ggtacagtac 1560
gcagggacag atggaccttg caaggttcca gctcagatgg cggtggacat gcaaactctg 1620
accccagttg ggaggttgat aaccgctaac cccgtaatca ctgaaagcac tgagaactct 1680
aagatgatgc tggaacttga tccaccattt ggggactctt acattgtcat aggagtcggg 1740
gagaagaaga tcacccacca ctggcacagg agtggcagca ccattggaaa agcatttgaa 1800
gccactgtga gaggtgccaa gagaatggca gtcttgggag acacagcctg ggactttgga 1860
tcagttggag gcgctctcaa ctcattgggc aagggcatcc atcaaatttt tggagcagct 1920
ttcaaatcat tgtttggagg aatgtcctgg ttctcacaaa tcctcattgg aacgttgctg 1980
atgtggttgg gtctgaacac aaagaatgga tctatttccc ttatgtgctt ggccttaggg 2040
ggagtgttga tcttcttatc cacagccgtc tctgctgat 2079

<210> SEQ ID NO 2
<211> LENGTH: 693
<212> TYPE: PRT
<213> ORGANISM: Zika virus

<400> SEQUENCE: 2

Met Arg Gly Ala Asp Thr Ser Val Gly Ile Val Gly Leu Leu Leu Thr
1 5 10 15

Thr Ala Met Ala Ala Glu Val Thr Arg Arg Gly Ser Ala Tyr Tyr Met
20 25 30

Tyr Leu Asp Arg Asn Asp Ala Gly Glu Ala Ile Ser Phe Pro Thr Thr
35 40 45

Leu Gly Met Asn Lys Cys Tyr Ile Gln Ile Met Asp Leu Gly His Met
50 55 60

Cys Asp Ala Thr Met Ser Tyr Glu Cys Pro Met Leu Asp Glu Gly Val
65 70 75 80

Glu Pro Asp Asp Val Asp Cys Trp Cys Asn Thr Thr Ser Thr Trp Val
85 90 95

Val Tyr Gly Thr Cys His His Lys Lys Gly Glu Ala Arg Arg Ser Arg
100 105 110

Arg Ala Val Thr Leu Pro Ser His Ser Thr Arg Lys Leu Gln Thr Arg
115 120 125

Ser Gln Thr Trp Leu Glu Ser Arg Glu Tyr Thr Lys His Leu Ile Arg
130 135 140

Val Glu Asn Trp Ile Phe Arg Asn Pro Gly Phe Ala Leu Ala Ala Ala
145 150 155 160

Ala Ile Ala Trp Leu Leu Gly Ser Ser Thr Ser Gln Lys Val Ile Tyr
165 170 175

Leu Val Met Ile Leu Leu Ile Ala Pro Ala Tyr Ser Ile Arg Cys Ile
180 185 190

Gly Val Ser Asn Arg Asp Phe Val Glu Gly Met Ser Gly Gly Thr Trp
195 200 205

Val Asp Val Val Leu Glu His Gly Gly Cys Val Thr Val Met Ala Gln
210 215 220

Asp Lys Pro Thr Val Asp Ile Glu Leu Val Thr Thr Thr Val Ser Asn
225 230 235 240

Met Ala Glu Val Arg Ser Tyr Cys Tyr Glu Ala Ser Ile Ser Asp Met
245 250 255

Ala Ser Asp Ser Arg Cys Pro Thr Gln Gly Glu Ala Tyr Leu Asp Lys
260 265 270

Gln Ser Asp Thr Gln Tyr Val Cys Lys Arg Thr Leu Val Asp Arg Gly
275 280 285

Trp Gly Asn Gly Cys Gly Leu Phe Gly Lys Gly Ser Leu Val Thr Cys
290 295 300

Ala Lys Phe Ala Cys Ser Lys Lys Met Thr Gly Lys Ser Ile Gln Pro

```
305                 310                 315                 320

Glu Asn Leu Glu Tyr Arg Ile Met Leu Ser Val His Gly Ser Gln His
                325                 330                 335

Ser Gly Met Ile Val Asn Asp Thr Gly His Glu Thr Asp Glu Asn Arg
            340                 345                 350

Ala Lys Val Glu Ile Thr Pro Asn Ser Pro Arg Ala Glu Ala Thr Leu
        355                 360                 365

Gly Gly Phe Gly Ser Leu Gly Leu Asp Cys Glu Pro Arg Thr Gly Leu
    370                 375                 380

Asp Phe Ser Asp Leu Tyr Tyr Leu Thr Met Asn Asn Lys His Trp Leu
385                 390                 395                 400

Val His Lys Glu Trp Phe His Asp Ile Pro Leu Pro Trp His Ala Gly
                405                 410                 415

Ala Asp Thr Gly Thr Pro His Trp Asn Asn Lys Glu Ala Leu Val Glu
            420                 425                 430

Phe Lys Asp Ala His Ala Lys Arg Gln Thr Val Val Val Leu Gly Ser
        435                 440                 445

Gln Glu Gly Ala Val His Thr Ala Leu Ala Gly Ala Leu Glu Ala Glu
    450                 455                 460

Met Asp Gly Ala Lys Gly Arg Leu Ser Ser Gly His Leu Lys Cys Arg
465                 470                 475                 480

Leu Lys Met Asp Lys Leu Arg Leu Lys Gly Val Ser Tyr Ser Leu Cys
                485                 490                 495

Thr Ala Ala Phe Thr Phe Thr Lys Ile Pro Ala Glu Thr Leu His Gly
            500                 505                 510

Thr Val Thr Val Glu Val Gln Tyr Ala Gly Thr Asp Gly Pro Cys Lys
        515                 520                 525

Val Pro Ala Gln Met Ala Val Asp Met Gln Thr Leu Thr Pro Val Gly
    530                 535                 540

Arg Leu Ile Thr Ala Asn Pro Val Ile Thr Glu Ser Thr Glu Asn Ser
545                 550                 555                 560

Lys Met Met Leu Glu Leu Asp Pro Pro Phe Gly Asp Ser Tyr Ile Val
                565                 570                 575

Ile Gly Val Gly Glu Lys Lys Ile Thr His His Trp His Arg Ser Gly
            580                 585                 590

Ser Thr Ile Gly Lys Ala Phe Glu Ala Thr Val Arg Gly Ala Lys Arg
        595                 600                 605

Met Ala Val Leu Gly Asp Thr Ala Trp Asp Phe Gly Ser Val Gly Gly
    610                 615                 620

Ala Leu Asn Ser Leu Gly Lys Gly Ile His Gln Ile Phe Gly Ala Ala
625                 630                 635                 640

Phe Lys Ser Leu Phe Gly Gly Met Ser Trp Phe Ser Gln Ile Leu Ile
                645                 650                 655

Gly Thr Leu Leu Met Trp Leu Gly Leu Asn Thr Lys Asn Gly Ser Ile
            660                 665                 670

Ser Leu Met Cys Leu Ala Leu Gly Gly Val Leu Ile Phe Leu Ser Thr
        675                 680                 685

Ala Val Ser Ala Asp
    690
```

<210> SEQ ID NO 3
<211> LENGTH: 18
<212> TYPE: PRT
<213> ORGANISM: Zika virus

<400> SEQUENCE: 3

Gly Ala Asp Thr Ser Val Gly Ile Val Gly Leu Leu Leu Thr Thr Ala
1 5 10 15

Met Ala

<210> SEQ ID NO 4
<211> LENGTH: 72
<212> TYPE: DNA
<213> ORGANISM: Japanese encephalitis virus

<400> SEQUENCE: 4
atgggcaagc ggtccgccgg ctctatcatg tggctggcct ctctggccgt ggtcatcgca 60
tgcgcaggag ca 72

<210> SEQ ID NO 5
<211> LENGTH: 24
<212> TYPE: PRT
<213> ORGANISM: Japanese encephalitis virus

<400> SEQUENCE: 5

Met Gly Lys Arg Ser Ala Gly Ser Ile Met Trp Leu Ala Ser Leu Ala
1 5 10 15

Val Val Ile Ala Cys Ala Gly Ala
20

<210> SEQ ID NO 6
<211> LENGTH: 1008
<212> TYPE: DNA
<213> ORGANISM: Japanese encephalitis virus

<400> SEQUENCE: 6
gaagcgttct atgtcatgac cgtgggttcg aagtcattct tagtccatag ggaatggttc 60
catgaccttt cccttccctg gacgtccccc tcaagcacgg catggagaaa cagagaactc 120
ctcatggaat ttgaagaggc acatgccaca aaacaatctg ttgtagctct tgggtcacag 180
gagggaggcc tccatcaagc gttggcagga gccatcgtgg tggagtactc gagctcagtg 240
aagttgacat caggtcacct gaaatgcagg ctaaaaatgg acaaactggc tctgaagggc 300
acgacttatg gcatgtgtac agagaaattc tcgttcgcga aaaatccagc ggacacaggc 360
catggaacag ttgtcattga gctcacatac tctggaagtg atggtccctg taaaattccg 420
attgtctcag tcgcgagctt aaacgacatg acccctgtgg ggaggctggt aacagtaaac 480
cccttcgtcg cgacatctag ctccaactca aaggtgctgg ttgagatgga acctcccttc 540
ggagactctt atatcgtggt tggaagaggg gacaagcaga ttaaccatca ctggcacaaa 600
gctggaagca cgctgggtaa agccttctca acaactttga aaggggctca gagactagca 660
gcgctaggcg acacagcctg ggatttcggc tccattggag ggtattcaa ctccataggg 720 aaagctgttc accaagtatt tggcggtgca ttcagaacgc tctttggggg aatgtcttgg 780
atcacacaag gactaatggg ggccttactt ctttggatgg gtgtcaacgc acgagaccgg 840
tcaatcgccc tggcttttct ggccacggga ggtgtgctcg tgtttttagc gaccaatgtg 900
catgctgaca ctggctgtgc cattgacatc acaagaaaag agatgaggtg tggaagtggc 960
atcttcgtgc ataacgacgt agaggcttgg gtagataggt acaaatat 1008

<210> SEQ ID NO 7
<211> LENGTH: 336

-continued

<212> TYPE: PRT
<213> ORGANISM: Japanese encephalitis virus

<400> SEQUENCE: 7

```
Glu Ala Phe Tyr Val Met Thr Val Gly Ser Lys Ser Phe Leu Val His
1               5                   10                  15

Arg Glu Trp Phe His Asp Leu Ser Leu Pro Trp Thr Ser Pro Ser Ser
            20                  25                  30

Thr Ala Trp Arg Asn Arg Glu Leu Leu Met Glu Phe Glu Glu Ala His
        35                  40                  45

Ala Thr Lys Gln Ser Val Val Ala Leu Gly Ser Gln Glu Gly Gly Leu
    50                  55                  60

His Gln Ala Leu Ala Gly Ala Ile Val Val Glu Tyr Ser Ser Ser Val
65                  70                  75                  80

Lys Leu Thr Ser Gly His Leu Lys Cys Arg Leu Lys Met Asp Lys Leu
                85                  90                  95

Ala Leu Lys Gly Thr Thr Tyr Gly Met Cys Thr Glu Lys Phe Ser Phe
            100                 105                 110

Ala Lys Asn Pro Ala Asp Thr Gly His Gly Thr Val Val Ile Glu Leu
        115                 120                 125

Thr Tyr Ser Gly Ser Asp Gly Pro Cys Lys Ile Pro Ile Val Ser Val
    130                 135                 140

Ala Ser Leu Asn Asp Met Thr Pro Val Gly Arg Leu Val Thr Val Asn
145                 150                 155                 160

Pro Phe Val Ala Thr Ser Ser Ser Asn Ser Lys Val Leu Val Glu Met
                165                 170                 175

Glu Pro Pro Phe Gly Asp Ser Tyr Ile Val Val Gly Arg Gly Asp Lys
            180                 185                 190

Gln Ile Asn His His Trp His Lys Ala Gly Ser Thr Leu Gly Lys Ala
        195                 200                 205

Phe Ser Thr Thr Leu Lys Gly Ala Gln Arg Leu Ala Ala Leu Gly Asp
    210                 215                 220

Thr Ala Trp Asp Phe Gly Ser Ile Gly Gly Val Phe Asn Ser Ile Gly
225                 230                 235                 240

Lys Ala Val His Gln Val Phe Gly Gly Ala Phe Arg Thr Leu Phe Gly
                245                 250                 255

Gly Met Ser Trp Ile Thr Gln Gly Leu Met Gly Ala Leu Leu Leu Trp
            260                 265                 270

Met Gly Val Asn Ala Arg Asp Arg Ser Ile Ala Leu Ala Phe Leu Ala
        275                 280                 285

Thr Gly Gly Val Leu Val Phe Leu Ala Thr Asn Val His Ala Asp Thr
    290                 295                 300

Gly Cys Ala Ile Asp Ile Thr Arg Lys Glu Met Arg Cys Gly Ser Gly
305                 310                 315                 320

Ile Phe Val His Asn Asp Val Glu Ala Trp Val Asp Arg Tyr Lys Tyr
                325                 330                 335
```

<210> SEQ ID NO 8
<211> LENGTH: 795
<212> TYPE: PRT
<213> ORGANISM: Zika virus

<400> SEQUENCE: 8

```
Met Lys Asn Pro Lys Lys Lys Ser Gly Gly Phe Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 9
<211> LENGTH: 795
<212> TYPE: PRT
<213> ORGANISM: Zika virus

<400> SEQUENCE: 9

Met Lys Asn Pro Lys Lys Lys Ser Gly Gly Phe Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Ile Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

-continued

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 10
<211> LENGTH: 791
<212> TYPE: PRT
<213> ORGANISM: Zika virus

<400> SEQUENCE: 10

Met Lys Asn Pro Lys Glu Glu Ile Arg Arg Ile Arg Ile Val Asn Met
1               5                   10                  15
```

-continued

```
Leu Lys Arg Gly Val Ala Arg Val Asn Pro Leu Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Arg Lys Arg Arg Gly Ala Asp Thr Ser Ile Gly Ile
            100                 105                 110

Ile Gly Leu Leu Leu Thr Thr Ala Met Ala Ala Glu Ile Thr Arg Arg
        115                 120                 125

Gly Ser Ala Tyr Tyr Met Tyr Leu Asp Arg Ser Asp Ala Gly Lys Ala
    130                 135                 140

Ile Ser Phe Ala Thr Thr Leu Gly Val Asn Lys Cys His Val Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Lys Val Glu Asn Trp Ile Phe Arg Asn Pro Gly
                245                 250                 255

Phe Ala Leu Val Ala Val Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Thr Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Gly Tyr Glu Thr Asp Glu
```

-continued

```
        435                 440                 445

Asp Arg Ala Lys Val Glu Val Thr Pro Asn Ser Pro Arg Ala Glu Ala
    450                 455                 460

Thr Leu Gly Gly Phe Gly Ser Leu Gly Leu Asp Cys Glu Pro Arg Thr
465                 470                 475                 480

Gly Leu Asp Phe Ser Asp Leu Tyr Tyr Leu Thr Met Asn Asn Lys His
                485                 490                 495

Trp Leu Val His Lys Glu Trp Phe His Asp Ile Pro Leu Pro Trp His
            500                 505                 510

Ala Gly Ala Asp Thr Gly Thr Pro His Trp Asn Asn Lys Glu Ala Leu
        515                 520                 525

Val Glu Phe Lys Asp Ala His Ala Lys Arg Gln Thr Val Val Val Leu
    530                 535                 540

Gly Ser Gln Glu Gly Ala Val His Thr Ala Leu Ala Gly Ala Leu Glu
545                 550                 555                 560

Ala Glu Met Asp Gly Ala Lys Gly Arg Leu Phe Ser Gly His Leu Lys
                565                 570                 575

Cys Arg Leu Lys Met Asp Lys Leu Arg Leu Lys Gly Val Ser Tyr Ser
            580                 585                 590

Leu Cys Thr Ala Ala Phe Thr Phe Thr Lys Val Pro Ala Glu Thr Leu
        595                 600                 605

His Gly Thr Val Thr Val Glu Val Gln Tyr Ala Gly Thr Asp Gly Pro
    610                 615                 620

Cys Lys Ile Pro Val Gln Met Ala Val Asp Met Gln Thr Leu Thr Pro
625                 630                 635                 640

Val Gly Arg Leu Ile Thr Ala Asn Pro Val Ile Thr Glu Ser Thr Glu
                645                 650                 655

Asn Ser Lys Met Met Leu Glu Leu Asp Pro Pro Phe Gly Asp Ser Tyr
            660                 665                 670

Ile Val Ile Gly Val Gly Asp Lys Lys Ile Thr His His Trp His Arg
        675                 680                 685

Ser Gly Ser Thr Ile Gly Lys Ala Phe Glu Ala Thr Val Arg Gly Ala
    690                 695                 700

Lys Arg Met Ala Val Leu Gly Asp Thr Ala Trp Asp Phe Gly Ser Val
705                 710                 715                 720

Gly Gly Val Phe Asn Ser Leu Gly Lys Gly Ile His Gln Ile Phe Gly
                725                 730                 735

Ala Ala Phe Lys Ser Leu Phe Gly Gly Met Ser Trp Phe Ser Gln Ile
            740                 745                 750

Leu Ile Gly Thr Leu Leu Val Trp Leu Gly Leu Asn Thr Lys Asn Gly
        755                 760                 765

Ser Ile Ser Leu Thr Cys Leu Ala Leu Gly Gly Val Met Ile Phe Leu
    770                 775                 780

Ser Thr Ala Val Ser Ala Asp
785                 790
```

<210> SEQ ID NO 11
<211> LENGTH: 795
<212> TYPE: PRT
<213> ORGANISM: Zika virus

<400> SEQUENCE: 11

```
Met Lys Asn Pro Lys Glu Glu Ile Arg Arg Ile Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Thr Asp Thr Ser Val Gly Ile
            100                 105                 110

Val Gly Leu Leu Leu Thr Thr Ala Met Ala Val Glu Val Thr Arg Arg
        115                 120                 125

Gly Ser Ala Tyr Tyr Met Tyr Leu Asp Arg Ser Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Ala Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Val Trp Leu Gly Leu Asn
        755                 760                 765

Thr Lys Asn Gly Ser Ile Ser Leu Thr Cys Leu Ala Leu Gly Gly Val
    770                 775                 780

Leu Ile Phe Leu Ser Thr Ala Val Ser Ala Asp
785                 790                 795


<210> SEQ ID NO 12
<211> LENGTH: 795
<212> TYPE: PRT
<213> ORGANISM: Zika virus

<400> SEQUENCE: 12

Met Lys Asn Pro Lys Lys Lys Ser Gly Gly Phe Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 13
<211> LENGTH: 795
<212> TYPE: PRT
<213> ORGANISM: Zika virus

<400> SEQUENCE: 13

Met Lys Asn Pro Lys Lys Lys Ser Gly Gly Phe Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 14
<211> LENGTH: 795
<212> TYPE: PRT
<213> ORGANISM: Zika virus

<400> SEQUENCE: 14

Met Lys Asn Pro Lys Lys Lys Ser Gly Gly Phe Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

-continued

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 15
<211> LENGTH: 795
<212> TYPE: PRT
<213> ORGANISM: Zika virus

<400> SEQUENCE: 15

Met Lys Asn Pro Lys Lys Lys Ser Gly Gly Phe Arg Ile Val Asn Met
1               5                   10                  15
```

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

-continued

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795


<210> SEQ ID NO 16
<211> LENGTH: 795
<212> TYPE: PRT
<213> ORGANISM: Zika virus

<400> SEQUENCE: 16

Met Lys Asn Pro Lys Lys Lys Ser Gly Gly Phe Arg Ile Val Asn Met
1               5                   10                  15
```

-continued

```
Leu Lys Arg Gly Val Ala Arg Val Ser Pro Phe Gly Gly Leu Lys Arg
            20                  25                  30

Leu Pro Ala Gly Leu Leu Leu Gly His Gly Pro Ile Arg Met Val Leu
        35                  40                  45

Ala Ile Leu Ala Phe Leu Arg Phe Thr Ala Ile Lys Pro Ser Leu Gly
    50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ala Ile Ala Trp Leu Leu Gly Ser Ser Thr
            260                 265                 270

Ser Gln Lys Val Ile Tyr Leu Val Met Ile Leu Leu Ile Ala Pro Ala
        275                 280                 285

Tyr Ser Ile Arg Cys Ile Gly Val Ser Asn Arg Asp Phe Val Glu Gly
    290                 295                 300

Met Ser Gly Gly Thr Trp Val Asp Val Val Leu Glu His Gly Gly Cys
305                 310                 315                 320

Val Thr Val Met Ala Gln Asp Lys Pro Thr Val Asp Ile Glu Leu Val
                325                 330                 335

Thr Thr Thr Val Ser Asn Met Ala Glu Val Arg Ser Tyr Cys Tyr Glu
            340                 345                 350

Ala Ser Ile Ser Asp Met Ala Ser Asp Ser Arg Cys Pro Thr Gln Gly
        355                 360                 365

Glu Ala Tyr Leu Asp Lys Gln Ser Asp Thr Gln Tyr Val Cys Lys Arg
    370                 375                 380

Thr Leu Val Asp Arg Gly Trp Gly Asn Gly Cys Gly Leu Phe Gly Lys
385                 390                 395                 400

Gly Ser Leu Val Thr Cys Ala Lys Phe Ala Cys Ser Lys Lys Met Thr
                405                 410                 415

Gly Lys Ser Ile Gln Pro Glu Asn Leu Glu Tyr Arg Ile Met Leu Ser
            420                 425                 430

Val His Gly Ser Gln His Ser Gly Met Ile Val Asn Asp Thr Gly His
```

```
        435                 440                 445

Glu Thr Asp Glu Asn Arg Ala Lys Val Glu Ile Thr Pro Asn Ser Pro
    450                 455                 460

Arg Ala Glu Ala Thr Leu Gly Gly Phe Gly Ser Leu Gly Leu Asp Cys
465                 470                 475                 480

Glu Pro Arg Thr Gly Leu Asp Phe Ser Asp Leu Tyr Tyr Leu Thr Met
                485                 490                 495

Asn Asn Lys His Trp Leu Val His Lys Glu Trp Phe His Asp Ile Pro
            500                 505                 510

Leu Pro Trp His Ala Gly Ala Asp Thr Gly Thr Pro His Trp Asn Asn
        515                 520                 525

Lys Glu Ala Leu Val Glu Phe Lys Asp Ala His Ala Lys Arg Gln Thr
    530                 535                 540

Val Val Val Leu Gly Ser Gln Glu Gly Ala Val His Thr Ala Leu Ala
545                 550                 555                 560

Gly Ala Leu Glu Ala Glu Met Asp Gly Ala Lys Gly Arg Leu Ser Ser
                565                 570                 575

Gly His Leu Lys Cys Arg Leu Lys Met Asp Lys Leu Arg Leu Lys Gly
            580                 585                 590

Val Ser Tyr Ser Leu Cys Thr Ala Ala Phe Thr Phe Thr Lys Ile Pro
        595                 600                 605

Ala Glu Thr Leu His Gly Thr Val Thr Val Glu Val Gln Tyr Ala Gly
    610                 615                 620

Thr Asp Gly Pro Cys Lys Val Pro Ala Gln Met Ala Val Asp Met Gln
625                 630                 635                 640

Thr Leu Thr Pro Val Gly Arg Leu Ile Thr Ala Asn Pro Val Ile Thr
                645                 650                 655

Glu Ser Thr Glu Asn Ser Lys Met Met Leu Glu Leu Asp Pro Pro Phe
            660                 665                 670

Gly Asp Ser Tyr Ile Val Ile Gly Val Gly Glu Lys Lys Ile Thr His
        675                 680                 685

His Trp His Arg Ser Gly Ser Thr Ile Gly Lys Ala Phe Glu Ala Thr
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala Asp
785                 790                 795
```

<210> SEQ ID NO 17
<211> LENGTH: 9999
<212> TYPE: DNA
<213> ORGANISM: Artificial
<220> FEATURE:
<223> OTHER INFORMATION: SAM Vector
<220> FEATURE:
<221> NAME/KEY: misc_feature
<222> LOCATION: (7562)..(7563)
<220> FEATURE:

<221> NAME/KEY: misc_feature
<222> LOCATION: (7562)..(7563)
<223> OTHER INFORMATION: Insert starts after nucleotide 7562

<400> SEQUENCE: 17

```
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
```

```
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttaac atgatgtgcc    2520
tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
cgacgaatcc gaaagagact aagattgtga ttgacactac cggcagtacc aaacctaagc   2700
aggacgatct cattctcact tgtttcagag ggtgggtgaa gcagttgcaa atagattaca   2760
aaggcaacga aataatgacg gcagctgcct ctcaagggct gacccgtaaa ggtgtgtatg   2820
ccgttcggta caaggtgaat gaaaatcctc tgtacgcacc cacctcagaa catgtgaacg   2880
tcctactgac ccgcacggag gaccgcatcg tgtggaaaac actagccggc gacccatgga   2940
taaaaacact gactgccaag taccctggga atttcactgc cacgatagag gagtggcaag   3000
cagagcatga tgccatcatg aggcacatct tggagagacc ggaccctacc gacgtcttcc   3060
agaataaggc aaacgtgtgt tgggccaagg ctttagtgcc ggtgctgaag accgctggca   3120
tagacatgac cactgaacaa tggaacactg tggattattt tgaaacggac aaagctcact   3180
cagcagagat agtattgaac caactatgcg tgaggttctt tggactcgat ctggactccg   3240
gtctattttc tgcacccact gttccgttat ccattaggaa taatcactgg gataactccc   3300
cgtcgcctaa catgtacggg ctgaataaag aagtggtccg tcagctctct cgcaggtacc   3360
cacaactgcc tcgggcagtt gccactggaa gagtctatga catgaacact ggtacactgc   3420
gcaattatga tccgcgcata aacctagtac ctgtaaacag aagactgcct catgctttag   3480
tcctccacca taatgaacac ccacagagtg acttttcttc attcgtcagc aaattgaagg   3540
gcagaactgt cctggtggtc ggggaaaagt tgtccgtccc aggcaaaatg gttgactggt   3600
tgtcagaccg gcctgaggct accttcagag ctcggctgga tttaggcatc ccaggtgatg   3660
tgcccaaata tgacataata tttgttaatg tgaggacccc atataaatac catcactatc   3720
agcagtgtga agaccatgcc attaagctta gcatgttgac caagaaagct tgtctgcatc   3780
tgaatcccgg cggaacctgt gtcagcatag gttatggtta cgctgacagg gccagcgaaa   3840
gcatcattgg tgctatagcg cggcagttca agttttcccg ggtatgcaaa ccgaaatcct   3900
cacttgaaga gacggaagtt ctgtttgtat tcattgggta cgatcgcaag gcccgtacgc   3960
acaatcctta caagctttca tcaaccttga ccaacattta tacaggttcc agactccacg   4020
aagccggatg tgcaccctca tatcatgtgg tgcgagggga tattgccacg gccaccgaag   4080
gagtgattat aaatgctgct aacagcaaag gacaacctgg cggagggggtg tgcggagcgc  4140
tgtataagaa attcccggaa agcttcgatt tacagccgat cgaagtagga aaagcgcgac   4200
tggtcaaagg tgcagctaaa catatcattc atgccgtagg accaaacttc aacaaagttt   4260
cggaggttga aggtgacaaa cagttggcag aggcttatga gtccatcgct aagattgtca   4320
acgataacaa ttacaagtca gtagcgattc cactgttgtc caccggcatc ttttccggga   4380
acaaagatcg actaacccaa tcattgaacc atttgctgac agctttagac accactgatg   4440
cagatgtagc catatactgc agggacaaga aatgggaaat gactctcaag gaagcagtgg   4500
ctaggagaga agcagtggag gagatatgca tatccgacga ctcttcagtg acagaacctg   4560
```

-continued atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga ccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gtgataaggc gcgcccaccc agcggccgca tacagcagca attggcaagc tgcttacata 7620
gaactcgcgg cgattggcat gccgccttaa aatttttatt ttattttttct tttcttttcc 7680
gaatcggatt ttgtttttaa tatttcaaaa aaaaaaaaaa aaaaaaaaaa aaaaaaaaaa 7740
aaaaaagaag agcgtttaaa cacgtgatat ctggcctcat gggccttcct ttcactgccc 7800
gctttccagt cgggaaacct gtcgtgccag ctgcattaac atggtcatag ctgtttcctt 7860
gcgtattggg cgctctccgc ttcctcgctc actgactcgc tgcgctcggt cgttcgggta 7920
aagcctgggg tgcctaatga gcaaaaggcc agcaaaaggc caggaaccgt aaaaaggccg 7980
cgttgctggc gtttttccat aggctccgcc cccctgacga gcatcacaaa aatcgacgct 8040
caagtcagag gtggcgaaac ccgacaggac tataaagata ccaggcgttt ccccctggaa 8100
gctccctcgt gcgctctcct gttccgaccc tgccgcttac cggatacctg tccgcctttc 8160
tcccttcggg aagcgtggcg ctttctcata gctcacgctg taggtatctc agttcggtgt 8220
aggtcgttcg ctccaagctg ggctgtgtgc acgaaccccc cgttcagccc gaccgctgcg 8280
ccttatccgg taactatcgt cttgagtcca acccggtaag acacgactta tcgccactgg 8340
cagcagccac tggtaacagg attagcagag cgaggtatgt aggcggtgct acagagttct 8400
tgaagtggtg gcctaactac ggctacacta gaagaacagt atttggtatc tgcgctctgc 8460
tgaagccagt taccttcgga aaaagagttg gtagctcttg atccggcaaa caaaccaccg 8520
ctggtagcgg tggttttttt gtttgcaagc agcagattac gcgcagaaaa aaaggatctc 8580
aagaagatcc tttgatcttt tctacggggt ctgacgctca gtggaacgaa aactcacgtt 8640
aagggatttt ggtcatgaat acacggtgcc tgactgcgtt agcaatttaa ctgtgataaa 8700
ctaccgcatt aaagcttatc gatgataagc tgtcaaacat gagaattctt agaaaaactc 8760
atcgagcatc aaatgaaact gcaatttatt catatcagga ttatcaatac catatttttg 8820
aaaaagccgt ttctgtaatg aaggagaaaa ctcaccgagg cagttccata ggatggcaag 8880
atcctggtat cggtctgcga ttccgactcg tccaacatca atacaaccta ttaatttccc 8940
ctcgtcaaaa ataaggttat caagtgagaa atcaccatga gtgacgactg aatccggtga 9000
gaatggcaaa agcttatgca tttctttcca gacttgttca acaggccagc cattacgctc 9060
gtcatcaaaa tcactcgcat caaccaaacc gttattcatt cgtgattgcg cctgagcgag 9120
acgaaatacg cgatcgctgt taaaaggaca attacaaaca ggaatcgaat gcaaccggcg 9180
caggaacact gccagcgcat caacaatatt ttcacctgaa tcaggatatt cttctaatac 9240
ctggaatgct gttttcccgg ggatcgcagt ggtgagtaac catgcatcat caggagtacg 9300

-continued

```
gataaaatgc ttgatggtcg gaagaggcat aaattccgtc agccagttta gtctgaccat   9360

ctcatctgta acatcattgg caacgctacc tttgccatgt ttcagaaaca actctggcgc   9420

atcgggcttc ccatacaatc gatagattgt cgcacctgat tgcccgacat tatcgcgagc   9480

ccatttatac ccatataaat cagcatccat gttggaattt aatcgcggcc tcgagcaaga   9540

cgtttcccgt tgaatatggc tcataacacc ccttgtatta ctgtttatgt aagcagacag   9600

ttttattgtt catgagcgga tacatatttg aatgtattta gaaaaataaa caaatagggg   9660

ttccgcgcac atttccccga aaagtgccac ctaaattgta agcgttaata ttttgttaaa   9720

attcgcgtta aatttttgtt aaatcagctc attttttaac caataggccg aaatcggcaa   9780

aatcccttat aaatcaaaag aatagaccga gatagggttg agtggccgct acagggcgct   9840

cccattcgcc attcaggctg cgcaactgtt gggaagggcg tttcggtgcg ggcctcttcg   9900

ctattacgcc agctggcgaa agggggatgt gctgcaaggc gattaagttg ggtaacgcca   9960

gggttttccc agtcacacgc gtaatacgac tcactatag                          9999
```

<210> SEQ ID NO 18
<211> LENGTH: 2091
<212> TYPE: DNA
<213> ORGANISM: Artificial Sequence
<220> FEATURE:
<223> OTHER INFORMATION: recombinant Zika virus antigen construct

<400> SEQUENCE: 18

```
atgggcaagc ggtccgccgg ctctatcatg tggctggcct ctctggccgt ggtcatcgca     60

tgcgcaggag cagcggaggt caccaggaga ggcagcgcct actatatgta cctggacaga    120

aatgatgccg gcgaggccat cagctttccc accacactgg gcatgaacaa gtgttacatc    180

cagatcatgg acctgggcca catgtgcgat gccaccatgt cctatgagtg tccaatgctg    240

gacgagggcg tggagcccga cgatgtggat tgctggtgta ataccacatc cacatgggtg    300

gtgtacggca cctgccacca caagaaggga gaggcaaggc gctctcggag agcagtgaca    360

ctgccttccc actctacccg gaagctgcag acaagatctc agacctggct ggagagccgg    420

gagtatacaa agcacctgat ccgggtggag aactggatct ttagaaatcc aggattcgca    480

ctggcagcag cagcaatcgc atggctgctg ggcagctcca cctcccagaa agtgatctac    540

ctggtcatga tcctgctgat cgcccctgcc tattccatca ggtgcatcgg cgtgtctaat    600

cgcgacttcg tggagggcat gtctggcggc acctgggtgg atgtggtgct ggagcacggc    660

ggctgcgtga cagtgatggc ccaggacaag ccaaccgtgg acatcgagct ggtgaccaca    720

accgtgagca acatggccga ggtgcggtcc tactgctatg aggccagcat ctccgacatg    780

gcctctgata gcagatgtcc cacccagggc gaggcctacc tggacaagca gtctgataca    840

cagtacgtgt gcaagaggac cctggtggac aggggatggg gaaatggatg tggcctgttt    900

ggcaagggca gcctggtgac atgcgccaag ttcgcctgtt ctaagaagat gaccggcaag    960

agcatccagc cagagaacct ggagtaccgg atcatgctga gcgtgcacgg cagccagcac   1020

tccggcatga tcgtgaacga cacaggccac gagacagatg agaatagggc caaggtggag   1080

atcacaccta acagcccacg cgccgaggcc accctgggag gatttggctc cctgggcctg   1140

gactgcgagc ctagaacagg cctggacttc tccgatctgt actatctgac catgaacaat   1200

aagcactggc tggtgcacaa ggagtggttt cacgacatcc cactgccatg gcacgcagga   1260

gcagatacag gaaccccaca ctggaacaat aaggaggccc tggtggagtt caaggatgcc   1320

cacgccaaga ggcagacagt ggtggtgctg ggcagccagg agggagcagt gcacaccgcc   1380
```

```
ctggcaggcg ccctggaggc cgagatggac ggagcaaagg gccgcctgtc tagcggccac   1440

ctgaagtgcc ggctgaagat ggataagctg agactgaagg gcgtgtccta ctctctgtgc   1500

acagccgcct tcaccttcac caagatccct gccgagacac tgcacggcac agtgaccgtg   1560

gaggtgcagt atgccggcac agacggcccc tgtaaggtgc ctgcccagat ggccgtggat   1620

atgcagacac tgacccctgt gggcaggctg atcaccgcca atccagtgat cacagagtcc   1680

accgagaact ctaagatgat gctggagctg gacccccctt ttggcgatag ctatatcgtg   1740

atcggcgtgg gcgagaagaa gatcacacac cactggcacc gcagcggctc cacaatcggc   1800

aaggcctttg aggccaccgt gaggggagca aagaggatgg ccgtgctggg cgacaccgca   1860

tgggatttcg gctccgtggg aggcgccctg aactctctgg gcaagggcat ccaccagatc   1920

ttcggcgccg cctttaagtc cctgttcggc ggcatgtctt ggtttagcca gatcctgatc   1980

ggcacactgc tgatgtggct gggcctgaac accaagaatg gctctatcag cctgatgtgc   2040

ctggccctgg gaggcgtgct gatcttcctg agcaccgccg tgtccgcctg a            2091
```

```
<210> SEQ ID NO 19
<211> LENGTH: 696
<212> TYPE: PRT
<213> ORGANISM: Artificial Sequence
<220> FEATURE:
<223> OTHER INFORMATION: recombinant Zika virus antigen construct

<400> SEQUENCE: 19

Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240
```

-continued

Thr Val Ser Asn Met Ala Glu Val Arg Ser Tyr Cys Tyr Glu Ala Ser
245 250 255

Ile Ser Asp Met Ala Ser Asp Ser Arg Cys Pro Thr Gln Gly Glu Ala
260 265 270

Tyr Leu Asp Lys Gln Ser Asp Thr Gln Tyr Val Cys Lys Arg Thr Leu
275 280 285

Val Asp Arg Gly Trp Gly Asn Gly Cys Gly Leu Phe Gly Lys Gly Ser
290 295 300

Leu Val Thr Cys Ala Lys Phe Ala Cys Ser Lys Lys Met Thr Gly Lys
305 310 315 320

Ser Ile Gln Pro Glu Asn Leu Glu Tyr Arg Ile Met Leu Ser Val His
325 330 335

Gly Ser Gln His Ser Gly Met Ile Val Asn Asp Thr Gly His Glu Thr
340 345 350

Asp Glu Asn Arg Ala Lys Val Glu Ile Thr Pro Asn Ser Pro Arg Ala
355 360 365

Glu Ala Thr Leu Gly Gly Phe Gly Ser Leu Gly Leu Asp Cys Glu Pro
370 375 380

Arg Thr Gly Leu Asp Phe Ser Asp Leu Tyr Tyr Leu Thr Met Asn Asn
385 390 395 400

Lys His Trp Leu Val His Lys Glu Trp Phe His Asp Ile Pro Leu Pro
405 410 415

Trp His Ala Gly Ala Asp Thr Gly Thr Pro His Trp Asn Asn Lys Glu
420 425 430

Ala Leu Val Glu Phe Lys Asp Ala His Ala Lys Arg Gln Thr Val Val
435 440 445

Val Leu Gly Ser Gln Glu Gly Ala Val His Thr Ala Leu Ala Gly Ala
450 455 460

Leu Glu Ala Glu Met Asp Gly Ala Lys Gly Arg Leu Ser Ser Gly His
465 470 475 480

Leu Lys Cys Arg Leu Lys Met Asp Lys Leu Arg Leu Lys Gly Val Ser
485 490 495

Tyr Ser Leu Cys Thr Ala Ala Phe Thr Phe Thr Lys Ile Pro Ala Glu
500 505 510

Thr Leu His Gly Thr Val Thr Val Glu Val Gln Tyr Ala Gly Thr Asp
515 520 525

Gly Pro Cys Lys Val Pro Ala Gln Met Ala Val Asp Met Gln Thr Leu
530 535 540

Thr Pro Val Gly Arg Leu Ile Thr Ala Asn Pro Val Ile Thr Glu Ser
545 550 555 560

Thr Glu Asn Ser Lys Met Met Leu Glu Leu Asp Pro Pro Phe Gly Asp
565 570 575

Ser Tyr Ile Val Ile Gly Val Gly Glu Lys Lys Ile Thr His His Trp
580 585 590

His Arg Ser Gly Ser Thr Ile Gly Lys Ala Phe Glu Ala Thr Val Arg
595 600 605

Gly Ala Lys Arg Met Ala Val Leu Gly Asp Thr Ala Trp Asp Phe Gly
610 615 620

Ser Val Gly Gly Ala Leu Asn Ser Leu Gly Lys Gly Ile His Gln Ile
625 630 635 640

Phe Gly Ala Ala Phe Lys Ser Leu Phe Gly Gly Met Ser Trp Phe Ser
645 650 655

```
Gln Ile Leu Ile Gly Thr Leu Leu Met Trp Leu Gly Leu Asn Thr Lys
            660                 665                 670

Asn Gly Ser Ile Ser Leu Met Cys Leu Ala Leu Gly Gly Val Leu Ile
        675                 680                 685

Phe Leu Ser Thr Ala Val Ser Ala
    690                 695


<210> SEQ ID NO 20
<211> LENGTH: 92
<212> TYPE: PRT
<213> ORGANISM: Zika virus

<400> SEQUENCE: 20

Ala Glu Val Thr Arg Arg Gly Ser Ala Tyr Tyr Met Tyr Leu Asp Arg
1               5                   10                  15

Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90


<210> SEQ ID NO 21
<211> LENGTH: 60
<212> TYPE: PRT
<213> ORGANISM: Zika virus

<400> SEQUENCE: 21

Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60


<210> SEQ ID NO 22
<211> LENGTH: 520
<212> TYPE: PRT
<213> ORGANISM: Zika virus

<400> SEQUENCE: 22

Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
```

-continued

```
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445

Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510
```

```
Phe Leu Ser Thr Ala Val Ser Ala
        515                 520


<210> SEQ ID NO 23
<211> LENGTH: 2091
<212> TYPE: DNA
<213> ORGANISM: Artificial Sequence
<220> FEATURE:
<223> OTHER INFORMATION: recombinant Zika virus antigen construct

<400> SEQUENCE: 23

atgggcaagc ggtccgccgg ctctatcatg tggctggcct ctctggccgt ggtcatcgca     60

tgcgcaggag cagcggaggt caccaggaga ggcagcgcct actatatgta cctggacaga    120

aatgatgccg gcgaggccat cagctttccc accacactgg gcatgaacaa gtgttacatc    180

cagatcatgg acctgggcca catgtgcgat gccaccatgt cctatgagtg tccaatgctg    240

gacgagggcg tggagcccga cgatgtggat tgctggtgta ataccacatc cacatgggtg    300

gtgtacggca cctgccacca caagaaggga gaggcaaggc gctctcggag agcagtgaca    360

ctgccttccc actctacccg gaagctgcag acaagatctc agacctggct ggagagccgg    420

gagtatacaa agcacctgat ccgggtggag aactggatct ttagaaatcc aggattcgca    480

ctggcagcag cagcaatcgc atggctgctg ggcagctcca cctcccagaa agtgatctac    540

ctggtcatga tcctgctgat cgcccctgcc tattccatca ggtgcatcgg cgtgtctaat    600

cgcgacttcg tggagggcat gtctggcggc acctgggtgg atgtggtgct ggagcacggc    660

ggctgcgtga cagtgatggc ccaggacaag ccaaccgtgg acatcgagct ggtgaccaca    720

accgtgagca acatggccga ggtgcggtcc tactgctatg aggccagcat ctccgacatg    780

gcctctgata gcagatgtcc cacccagggc gaggcctacc tggacaagca gtctgataca    840

cagtacgtgt gcaagaggac cctggtggac aggggatggg gaaatggatg tggcctgttt    900

ggcaagggca gcctggtgac atgcgccaag ttcgcctgtt ctaagaagat gaccggcaag    960

agcatccagc cagagaacct ggagtaccgg atcatgctga gcgtgcacgg cagccagcac   1020

tccggcatga tcgtgaacga cacaggccac gagacagatg agaatagggc caaggtggag   1080

atcacaccta acagcccacg cgccgaggcc accctgggag gatttggctc cctgggcctg   1140

gactgcgagc ctagaacagg cctggacttc tccgatctgt actatctgac catgaacaat   1200

aagcactggc tggtgcacaa ggagtggttt cacgacatcc cactgccatg gcacgcagga   1260

gcagatacag gaaccccaca ctggaacaat aaggaggccc tggtggagtt caaggatgcc   1320

cacgccaaga ggcagacagt ggtggtgctg ggcagccagg agggagcagt gcacaccgcc   1380

ctggcaggcg ccctggaggc cgagatggac ggagcaaagg gccgcctgtc tagcggccac   1440

ctgaagtgcc ggctgaagat ggataagctg agactgaagg gcgtgtccta ctctctgtgc   1500

acagccgcct tcaccttcac caagatccct gccgagacac tgcacggcac agtgaccgtg   1560

gaggtgcagt atgccggcac agacggcccc tgtaaggtgc ctgcccagat ggccgtggat   1620

atgcagacac tgacccctgt gggcaggctg atcaccgcca atccagtgat cacagagtcc   1680

accgagaact ctaagatgat gctggagctg gaccccccct ttggcgatag ctatatcgtg   1740

atcggcgtgg gcgagaagaa gatcacacac cactggcacc gcagcggctc caccctgggc   1800

aaggccttta gcaccaccct gaagggagca cagaggctgg ccgccctggg cgacaccgca   1860

tgggatttcg gctccatcgg aggcgtgttc aactctatcg gcaaggccgt gcaccaggtg   1920

ttcggcggcg cctttcggac cctgttcggc ggcatgtctt ggatcaccca gggcctgatg   1980
```

```
ggcgccctgc tgctgtggat gggcgtgaac gcccgggacc ggtctatcgc cctggccttc   2040

ctggccaccg gaggcgtgct ggtgttcctg gccaccaacg tgcacgcctg a            2091


<210> SEQ ID NO 24
<211> LENGTH: 696
<212> TYPE: PRT
<213> ORGANISM: Artificial Sequence
<220> FEATURE:
<223> OTHER INFORMATION: recombinant Zika virus antigen construct

<400> SEQUENCE: 24

Met Gly Lys Arg Ser Ala Gly Ser Ile Met Trp Leu Ala Ser Leu Ala
1               5                   10                  15

Val Val Ile Ala Cys Ala Gly Ala Ala Glu Val Thr Arg Arg Gly Ser
            20                  25                  30

Ala Tyr Tyr Met Tyr Leu Asp Arg Asn Asp Ala Gly Glu Ala Ile Ser
        35                  40                  45

Phe Pro Thr Thr Leu Gly Met Asn Lys Cys Tyr Ile Gln Ile Met Asp
    50                  55                  60

Leu Gly His Met Cys Asp Ala Thr Met Ser Tyr Glu Cys Pro Met Leu
65                  70                  75                  80

Asp Glu Gly Val Glu Pro Asp Asp Val Asp Cys Trp Cys Asn Thr Thr
                85                  90                  95

Ser Thr Trp Val Val Tyr Gly Thr Cys His His Lys Lys Gly Glu Ala
            100                 105                 110

Arg Arg Ser Arg Arg Ala Val Thr Leu Pro Ser His Ser Thr Arg Lys
        115                 120                 125

Leu Gln Thr Arg Ser Gln Thr Trp Leu Glu Ser Arg Glu Tyr Thr Lys
    130                 135                 140

His Leu Ile Arg Val Glu Asn Trp Ile Phe Arg Asn Pro Gly Phe Ala
145                 150                 155                 160

Leu Ala Ala Ala Ala Ile Ala Trp Leu Leu Gly Ser Ser Thr Ser Gln
                165                 170                 175

Lys Val Ile Tyr Leu Val Met Ile Leu Leu Ile Ala Pro Ala Tyr Ser
            180                 185                 190

Ile Arg Cys Ile Gly Val Ser Asn Arg Asp Phe Val Glu Gly Met Ser
        195                 200                 205

Gly Gly Thr Trp Val Asp Val Val Leu Glu His Gly Gly Cys Val Thr
    210                 215                 220

Val Met Ala Gln Asp Lys Pro Thr Val Asp Ile Glu Leu Val Thr Thr
225                 230                 235                 240

Thr Val Ser Asn Met Ala Glu Val Arg Ser Tyr Cys Tyr Glu Ala Ser
                245                 250                 255

Ile Ser Asp Met Ala Ser Asp Ser Arg Cys Pro Thr Gln Gly Glu Ala
            260                 265                 270

Tyr Leu Asp Lys Gln Ser Asp Thr Gln Tyr Val Cys Lys Arg Thr Leu
        275                 280                 285

Val Asp Arg Gly Trp Gly Asn Gly Cys Gly Leu Phe Gly Lys Gly Ser
    290                 295                 300

Leu Val Thr Cys Ala Lys Phe Ala Cys Ser Lys Lys Met Thr Gly Lys
305                 310                 315                 320

Ser Ile Gln Pro Glu Asn Leu Glu Tyr Arg Ile Met Leu Ser Val His
                325                 330                 335

Gly Ser Gln His Ser Gly Met Ile Val Asn Asp Thr Gly His Glu Thr
```

```
            340                 345                 350

Asp Glu Asn Arg Ala Lys Val Glu Ile Thr Pro Asn Ser Pro Arg Ala
        355                 360                 365

Glu Ala Thr Leu Gly Gly Phe Gly Ser Leu Gly Leu Asp Cys Glu Pro
    370                 375                 380

Arg Thr Gly Leu Asp Phe Ser Asp Leu Tyr Tyr Leu Thr Met Asn Asn
385                 390                 395                 400

Lys His Trp Leu Val His Lys Glu Trp Phe His Asp Ile Pro Leu Pro
                405                 410                 415

Trp His Ala Gly Ala Asp Thr Gly Thr Pro His Trp Asn Asn Lys Glu
            420                 425                 430

Ala Leu Val Glu Phe Lys Asp Ala His Ala Lys Arg Gln Thr Val Val
        435                 440                 445

Val Leu Gly Ser Gln Glu Gly Ala Val His Thr Ala Leu Ala Gly Ala
    450                 455                 460

Leu Glu Ala Glu Met Asp Gly Ala Lys Gly Arg Leu Ser Ser Gly His
465                 470                 475                 480

Leu Lys Cys Arg Leu Lys Met Asp Lys Leu Arg Leu Lys Gly Val Ser
                485                 490                 495

Tyr Ser Leu Cys Thr Ala Ala Phe Thr Phe Thr Lys Ile Pro Ala Glu
            500                 505                 510

Thr Leu His Gly Thr Val Thr Val Glu Val Gln Tyr Ala Gly Thr Asp
        515                 520                 525

Gly Pro Cys Lys Val Pro Ala Gln Met Ala Val Asp Met Gln Thr Leu
    530                 535                 540

Thr Pro Val Gly Arg Leu Ile Thr Ala Asn Pro Val Ile Thr Glu Ser
545                 550                 555                 560

Thr Glu Asn Ser Lys Met Met Leu Glu Leu Asp Pro Pro Phe Gly Asp
                565                 570                 575

Ser Tyr Ile Val Ile Gly Val Gly Glu Lys Lys Ile Thr His His Trp
            580                 585                 590

His Arg Ser Gly Ser Thr Leu Gly Lys Ala Phe Ser Thr Thr Leu Lys
        595                 600                 605

Gly Ala Gln Arg Leu Ala Ala Leu Gly Asp Thr Ala Trp Asp Phe Gly
    610                 615                 620

Ser Ile Gly Gly Val Phe Asn Ser Ile Gly Lys Ala Val His Gln Val
625                 630                 635                 640

Phe Gly Gly Ala Phe Arg Thr Leu Phe Gly Gly Met Ser Trp Ile Thr
                645                 650                 655

Gln Gly Leu Met Gly Ala Leu Leu Leu Trp Met Gly Val Asn Ala Arg
            660                 665                 670

Asp Arg Ser Ile Ala Leu Ala Phe Leu Ala Thr Gly Gly Val Leu Val
        675                 680                 685

Phe Leu Ala Thr Asn Val His Ala
    690                 695


<210> SEQ ID NO 25
<211> LENGTH: 92
<212> TYPE: PRT
<213> ORGANISM: Zika virus

<400> SEQUENCE: 25

Ala Glu Val Thr Arg Arg Gly Ser Ala Tyr Tyr Met Tyr Leu Asp Arg
1               5                   10                  15
```

```
Asn Asp Ala Gly Glu Ala Ile Ser Phe Pro Thr Thr Leu Gly Met Asn
            20                  25                  30

Lys Cys Tyr Ile Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg
                85                  90


<210> SEQ ID NO 26
<211> LENGTH: 60
<212> TYPE: PRT
<213> ORGANISM: Zika virus

<400> SEQUENCE: 26

Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60


<210> SEQ ID NO 27
<211> LENGTH: 520
<212> TYPE: PRT
<213> ORGANISM: Artificial Sequence
<220> FEATURE:
<223> OTHER INFORMATION: hybrid Zika-JEV E protein

<400> SEQUENCE: 27

Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
```

```
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285

Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Leu Gly Lys Ala Phe Ser Thr Thr Leu Lys
            420                 425                 430

Gly Ala Gln Arg Leu Ala Ala Leu Gly Asp Thr Ala Trp Asp Phe Gly
        435                 440                 445

Ser Ile Gly Gly Val Phe Asn Ser Ile Gly Lys Ala Val His Gln Val
    450                 455                 460

Phe Gly Gly Ala Phe Arg Thr Leu Phe Gly Gly Met Ser Trp Ile Thr
465                 470                 475                 480

Gln Gly Leu Met Gly Ala Leu Leu Leu Trp Met Gly Val Asn Ala Arg
                485                 490                 495

Asp Arg Ser Ile Ala Leu Ala Phe Leu Ala Thr Gly Gly Val Leu Val
            500                 505                 510

Phe Leu Ala Thr Asn Val His Ala
        515                 520


<210> SEQ ID NO 28
<211> LENGTH: 2082
<212> TYPE: DNA
<213> ORGANISM: Artificial Sequence
<220> FEATURE:
<223> OTHER INFORMATION: recombinant Zika virus antigen construct

<400> SEQUENCE: 28

atgggcaagc ggtccgccgg ctctatcatg tggctggcct ctctggccgt ggtcatcgca     60

tgcgcaggag caaccaggag aggcagcgcc tactatatgt acctggacag aaatgatgcc    120
```

-continued

```
ggcgaggcca tcagctttcc caccacactg ggcatgaaca agtgttacat ccagatcatg    180
gacctgggcc acatgtgcga tgccaccatg tcctatgagt gtccaatgct ggacgagggc    240
gtggagcccg acgatgtgga ttgctggtgt aataccacat ccacatgggt ggtgtacggc    300
acctgccacc acaagaaggg agaggcaagg cgctctcgga gagcagtgac actgccttcc    360
cactctaccc ggaagctgca gacaagatct cagacctggc tggagagccg ggagtataca    420
aagcacctga tccgggtgga gaactggatc tttagaaatc caggattcgc actggcagca    480
gcagcaatcg catggctgct gggcagctcc acctcccaga aagtgatcta cctggtcatg    540
atcctgctga tcgcccctgc ctattccatc aggtgcatcg gcgtgtctaa tcgcgacttc    600
gtggagggca tgtctggcgg cacctgggtg gatgtggtgc tggagcacgg cggctgcgtg    660
acagtgatgg cccaggacaa gccaaccgtg gacatcgagc tggtgaccac aaccgtgagc    720
aacatggccg aggtgcggtc ctactgctat gaggccagca tctccgacat ggcctctgat    780
agcagatgtc ccacccaggg cgaggcctac ctggacaagc agtctgatac acagtacgtg    840
tgcaagagga ccctggtgga caggggatgg ggaaatggat gtggcctgtt tggcaagggc    900
agcctggtga catgcgccaa gttcgcctgt tctaagaaga tgaccggcaa gagcatccag    960
ccagagaacc tggagtaccg gatcatgctg agcgtgcacg gcagccagca ctccggcatg   1020
atcgtgaacg acacaggcca cgagacagat gagaataggg ccaaggtgga gatcacacct   1080
aacagcccac gcgccgaggc caccctggga ggatttggct ccctgggcct ggactgcgag   1140
cctagaacag gcctggactt ctccgatctg tactatctga ccatgaacaa taagcactgg   1200
ctggtgcaca aggagtggtt tcacgacatc ccactgccat ggcacgcagg agcagataca   1260
ggaaccccac actggaacaa taaggaggcc ctggtggagt tcaaggatgc ccacgccaag   1320
aggcagacag tggtggtgct gggcagccag gagggagcag tgcacaccgc cctggcaggc   1380
gccctggagg ccgagatgga cggagcaaag ggccgcctgt ctagcggcca cctgaagtgc   1440
cggctgaaga tggataagct gagactgaag ggcgtgtcct actctctgtg cacagccgcc   1500
ttcaccttca ccaagatccc tgccgagaca ctgcacggca cagtgaccgt ggaggtgcag   1560
tatgccggca cagacggccc ctgtaaggtg cctgcccaga tggccgtgga tatgcagaca   1620
ctgacccctg tgggcaggct gatcaccgcc aatccagtga tcacagagtc caccgagaac   1680
tctaagatga tgctggagct ggaccccccct tttggcgata gctatatcgt gatcggcgtg   1740
ggcgagaaga agatcacaca ccactggcac cgcagcggct ccacaatcgg caaggccttt   1800
gaggccaccg tgaggggagc aaagaggatg gccgtgctgg gcgacaccgc atgggatttc   1860
ggctccgtgg gaggcgccct gaactctctg ggcaagggca tccaccagat cttcggcgcc   1920
gcctttaagt ccctgttcgg cggcatgtct tggtttagcc agatcctgat cggcacactg   1980
ctgatgtggc tgggcctgaa caccaagaat ggctctatca gcctgatgtg cctggccctg   2040
ggaggcgtgc tgatcttcct gagcaccgcc gtgtccgcct ga                      2082
```

<210> SEQ ID NO 29
<211> LENGTH: 693
<212> TYPE: PRT
<213> ORGANISM: Artificial Sequence
<220> FEATURE:
<223> OTHER INFORMATION: recombinant Zika virus antigen construct

<400> SEQUENCE: 29

```
Met Gly Lys Arg Ser Ala Gly Ser Ile Met Trp Leu Ala Ser Leu Ala
1               5                   10                  15
```

```
Val Val Ile Ala Cys Ala Gly Ala Thr Arg Arg Gly Ser Ala Tyr Tyr
            20                  25                  30

Met Tyr Leu Asp Arg Asn Asp Ala Gly Glu Ala Ile Ser Phe Pro Thr
        35                  40                  45

Thr Leu Gly Met Asn Lys Cys Tyr Ile Gln Ile Met Asp Leu Gly His
    50                  55                  60

Met Cys Asp Ala Thr Met Ser Tyr Glu Cys Pro Met Leu Asp Glu Gly
65                  70                  75                  80

Val Glu Pro Asp Asp Val Asp Cys Trp Cys Asn Thr Thr Ser Thr Trp
                85                  90                  95

Val Val Tyr Gly Thr Cys His His Lys Lys Gly Glu Ala Arg Arg Ser
            100                 105                 110

Arg Arg Ala Val Thr Leu Pro Ser His Ser Thr Arg Lys Leu Gln Thr
        115                 120                 125

Arg Ser Gln Thr Trp Leu Glu Ser Arg Glu Tyr Thr Lys His Leu Ile
    130                 135                 140

Arg Val Glu Asn Trp Ile Phe Arg Asn Pro Gly Phe Ala Leu Ala Ala
145                 150                 155                 160

Ala Ala Ile Ala Trp Leu Leu Gly Ser Ser Thr Ser Gln Lys Val Ile
                165                 170                 175

Tyr Leu Val Met Ile Leu Leu Ile Ala Pro Ala Tyr Ser Ile Arg Cys
            180                 185                 190

Ile Gly Val Ser Asn Arg Asp Phe Val Glu Gly Met Ser Gly Gly Thr
        195                 200                 205

Trp Val Asp Val Val Leu Glu His Gly Gly Cys Val Thr Val Met Ala
    210                 215                 220

Gln Asp Lys Pro Thr Val Asp Ile Glu Leu Val Thr Thr Thr Val Ser
225                 230                 235                 240

Asn Met Ala Glu Val Arg Ser Tyr Cys Tyr Glu Ala Ser Ile Ser Asp
                245                 250                 255

Met Ala Ser Asp Ser Arg Cys Pro Thr Gln Gly Glu Ala Tyr Leu Asp
            260                 265                 270

Lys Gln Ser Asp Thr Gln Tyr Val Cys Lys Arg Thr Leu Val Asp Arg
        275                 280                 285

Gly Trp Gly Asn Gly Cys Gly Leu Phe Gly Lys Gly Ser Leu Val Thr
    290                 295                 300

Cys Ala Lys Phe Ala Cys Ser Lys Lys Met Thr Gly Lys Ser Ile Gln
305                 310                 315                 320

Pro Glu Asn Leu Glu Tyr Arg Ile Met Leu Ser Val His Gly Ser Gln
                325                 330                 335

His Ser Gly Met Ile Val Asn Asp Thr Gly His Glu Thr Asp Glu Asn
            340                 345                 350

Arg Ala Lys Val Glu Ile Thr Pro Asn Ser Pro Arg Ala Glu Ala Thr
        355                 360                 365

Leu Gly Gly Phe Gly Ser Leu Gly Leu Asp Cys Glu Pro Arg Thr Gly
    370                 375                 380

Leu Asp Phe Ser Asp Leu Tyr Tyr Leu Thr Met Asn Asn Lys His Trp
385                 390                 395                 400

Leu Val His Lys Glu Trp Phe His Asp Ile Pro Leu Pro Trp His Ala
                405                 410                 415

Gly Ala Asp Thr Gly Thr Pro His Trp Asn Asn Lys Glu Ala Leu Val
            420                 425                 430

Glu Phe Lys Asp Ala His Ala Lys Arg Gln Thr Val Val Val Leu Gly
```

```
        435                 440                 445

Ser Gln Glu Gly Ala Val His Thr Ala Leu Ala Gly Ala Leu Glu Ala
    450                 455                 460

Glu Met Asp Gly Ala Lys Gly Arg Leu Ser Ser Gly His Leu Lys Cys
465                 470                 475                 480

Arg Leu Lys Met Asp Lys Leu Arg Leu Lys Gly Val Ser Tyr Ser Leu
                485                 490                 495

Cys Thr Ala Ala Phe Thr Phe Thr Lys Ile Pro Ala Glu Thr Leu His
            500                 505                 510

Gly Thr Val Thr Val Glu Val Gln Tyr Ala Gly Thr Asp Gly Pro Cys
        515                 520                 525

Lys Val Pro Ala Gln Met Ala Val Asp Met Gln Thr Leu Thr Pro Val
    530                 535                 540

Gly Arg Leu Ile Thr Ala Asn Pro Val Ile Thr Glu Ser Thr Glu Asn
545                 550                 555                 560

Ser Lys Met Met Leu Glu Leu Asp Pro Pro Phe Gly Asp Ser Tyr Ile
                565                 570                 575

Val Ile Gly Val Gly Glu Lys Lys Ile Thr His His Trp His Arg Ser
            580                 585                 590

Gly Ser Thr Ile Gly Lys Ala Phe Glu Ala Thr Val Arg Gly Ala Lys
        595                 600                 605

Arg Met Ala Val Leu Gly Asp Thr Ala Trp Asp Phe Gly Ser Val Gly
    610                 615                 620

Gly Ala Leu Asn Ser Leu Gly Lys Gly Ile His Gln Ile Phe Gly Ala
625                 630                 635                 640

Ala Phe Lys Ser Leu Phe Gly Gly Met Ser Trp Phe Ser Gln Ile Leu
                645                 650                 655

Ile Gly Thr Leu Leu Met Trp Leu Gly Leu Asn Thr Lys Asn Gly Ser
            660                 665                 670

Ile Ser Leu Met Cys Leu Ala Leu Gly Gly Val Leu Ile Phe Leu Ser
        675                 680                 685

Thr Ala Val Ser Ala
    690


<210> SEQ ID NO 30
<211> LENGTH: 89
<212> TYPE: PRT
<213> ORGANISM: Zika virus

<400> SEQUENCE: 30

Thr Arg Arg Gly Ser Ala Tyr Tyr Met Tyr Leu Asp Arg Asn Asp Ala
1               5                   10                  15

Gly Glu Ala Ile Ser Phe Pro Thr Thr Leu Gly Met Asn Lys Cys Tyr
            20                  25                  30

Ile Gln Ile Met Asp Leu Gly His Met Cys Asp Ala Thr Met Ser Tyr
        35                  40                  45

Glu Cys Pro Met Leu Asp Glu Gly Val Glu Pro Asp Asp Val Asp Cys
    50                  55                  60

Trp Cys Asn Thr Thr Ser Thr Trp Val Val Tyr Gly Thr Cys His His
65                  70                  75                  80

Lys Lys Gly Glu Ala Arg Arg Ser Arg
                85


<210> SEQ ID NO 31
<211> LENGTH: 60
```

```
<212> TYPE: PRT
<213> ORGANISM: Zika virus

<400> SEQUENCE: 31

Arg Ala Val Thr Leu Pro Ser His Ser Thr Arg Lys Leu Gln Thr Arg
1               5                   10                  15

Ser Gln Thr Trp Leu Glu Ser Arg Glu Tyr Thr Lys His Leu Ile Arg
            20                  25                  30

Val Glu Asn Trp Ile Phe Arg Asn Pro Gly Phe Ala Leu Ala Ala Ala
        35                  40                  45

Ala Ile Ala Trp Leu Leu Gly Ser Ser Thr Ser Gln
    50                  55                  60


<210> SEQ ID NO 32
<211> LENGTH: 520
<212> TYPE: PRT
<213> ORGANISM: Zika virus

<400> SEQUENCE: 32

Lys Val Ile Tyr Leu Val Met Ile Leu Leu Ile Ala Pro Ala Tyr Ser
1               5                   10                  15

Ile Arg Cys Ile Gly Val Ser Asn Arg Asp Phe Val Glu Gly Met Ser
            20                  25                  30

Gly Gly Thr Trp Val Asp Val Val Leu Glu His Gly Gly Cys Val Thr
        35                  40                  45

Val Met Ala Gln Asp Lys Pro Thr Val Asp Ile Glu Leu Val Thr Thr
    50                  55                  60

Thr Val Ser Asn Met Ala Glu Val Arg Ser Tyr Cys Tyr Glu Ala Ser
65                  70                  75                  80

Ile Ser Asp Met Ala Ser Asp Ser Arg Cys Pro Thr Gln Gly Glu Ala
                85                  90                  95

Tyr Leu Asp Lys Gln Ser Asp Thr Gln Tyr Val Cys Lys Arg Thr Leu
            100                 105                 110

Val Asp Arg Gly Trp Gly Asn Gly Cys Gly Leu Phe Gly Lys Gly Ser
        115                 120                 125

Leu Val Thr Cys Ala Lys Phe Ala Cys Ser Lys Lys Met Thr Gly Lys
    130                 135                 140

Ser Ile Gln Pro Glu Asn Leu Glu Tyr Arg Ile Met Leu Ser Val His
145                 150                 155                 160

Gly Ser Gln His Ser Gly Met Ile Val Asn Asp Thr Gly His Glu Thr
                165                 170                 175

Asp Glu Asn Arg Ala Lys Val Glu Ile Thr Pro Asn Ser Pro Arg Ala
            180                 185                 190

Glu Ala Thr Leu Gly Gly Phe Gly Ser Leu Gly Leu Asp Cys Glu Pro
        195                 200                 205

Arg Thr Gly Leu Asp Phe Ser Asp Leu Tyr Tyr Leu Thr Met Asn Asn
    210                 215                 220

Lys His Trp Leu Val His Lys Glu Trp Phe His Asp Ile Pro Leu Pro
225                 230                 235                 240

Trp His Ala Gly Ala Asp Thr Gly Thr Pro His Trp Asn Asn Lys Glu
                245                 250                 255

Ala Leu Val Glu Phe Lys Asp Ala His Ala Lys Arg Gln Thr Val Val
            260                 265                 270

Val Leu Gly Ser Gln Glu Gly Ala Val His Thr Ala Leu Ala Gly Ala
        275                 280                 285
```

```
Leu Glu Ala Glu Met Asp Gly Ala Lys Gly Arg Leu Ser Ser Gly His
    290                 295                 300

Leu Lys Cys Arg Leu Lys Met Asp Lys Leu Arg Leu Lys Gly Val Ser
305                 310                 315                 320

Tyr Ser Leu Cys Thr Ala Ala Phe Thr Phe Thr Lys Ile Pro Ala Glu
                325                 330                 335

Thr Leu His Gly Thr Val Thr Val Glu Val Gln Tyr Ala Gly Thr Asp
            340                 345                 350

Gly Pro Cys Lys Val Pro Ala Gln Met Ala Val Asp Met Gln Thr Leu
        355                 360                 365

Thr Pro Val Gly Arg Leu Ile Thr Ala Asn Pro Val Ile Thr Glu Ser
    370                 375                 380

Thr Glu Asn Ser Lys Met Met Leu Glu Leu Asp Pro Pro Phe Gly Asp
385                 390                 395                 400

Ser Tyr Ile Val Ile Gly Val Gly Glu Lys Lys Ile Thr His His Trp
                405                 410                 415

His Arg Ser Gly Ser Thr Ile Gly Lys Ala Phe Glu Ala Thr Val Arg
            420                 425                 430

Gly Ala Lys Arg Met Ala Val Leu Gly Asp Thr Ala Trp Asp Phe Gly
        435                 440                 445

Ser Val Gly Gly Ala Leu Asn Ser Leu Gly Lys Gly Ile His Gln Ile
    450                 455                 460

Phe Gly Ala Ala Phe Lys Ser Leu Phe Gly Gly Met Ser Trp Phe Ser
465                 470                 475                 480

Gln Ile Leu Ile Gly Thr Leu Leu Met Trp Leu Gly Leu Asn Thr Lys
                485                 490                 495

Asn Gly Ser Ile Ser Leu Met Cys Leu Ala Leu Gly Gly Val Leu Ile
            500                 505                 510

Phe Leu Ser Thr Ala Val Ser Ala
        515                 520
```

<210> SEQ ID NO 33
<211> LENGTH: 12090
<212> TYPE: DNA
<213> ORGANISM: Artificial Sequence
<220> FEATURE:
<223> OTHER INFORMATION: SAM vector backbone with ZIka antigen insert

<400> SEQUENCE: 33

```
ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720
```

-continued

```
ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaagccgatg   1620

tcgacttgat gttacaagag gctggggccg gctcagtgga gacacctcgt ggcttgataa   1680

aggttaccag ctacgatggc gaggacaaga tcggctctta cgctgtgctt tctccgcagg   1740

ctgtactcaa gagtgaaaaa ttatcttgca tccaccctct cgctgaacaa gtcatagtga   1800

taacacactc tggccgaaaa gggcgttatg ccgtggaacc ataccatggt aaagtagtgg   1860

tgccagaggg acatgcaata cccgtccagg actttcaagc tctgagtgaa agtgccacca   1920

ttgtgtacaa cgaacgtgag ttcgtaaaca ggtacctgca ccatattgcc acacatggag   1980

gagcgctgaa cactgatgaa gaatattaca aaactgtcaa gcccagcgag cacgacggcg   2040

aatacctgta cgacatcgac aggaaacagt gcgtcaagaa agaactagtc actgggctag   2100

ggctcacagg cgagctggtg gatcctccct tccatgaatt cgcctacgag agtctgagaa   2160

cacgaccagc cgctccttac caagtaccaa ccataggggt gtatggcgtg ccaggatcag   2220

gcaagtctgg catcattaaa agcgcagtca ccaaaaaaga tctagtggtg agcgccaaga   2280

aagaaaactg tgcagaaatt ataagggacg tcaagaaaat gaaagggctg gacgtcaatg   2340

ccagaactgt ggactcagtg ctcttgaatg gatgcaaaca ccccgtagag accctgtata   2400

ttgacgaagc ttttgcttgt catgcaggta ctctcagagc gctcatagcc attataagac   2460

ctaaaaaggc agtgctctgc ggggatccca aacagtgcgg tttttttaac atgatgtgcc   2520

tgaaagtgca ttttaaccac gagatttgca cacaagtctt ccacaaaagc atctctcgcc   2580

gttgcactaa atctgtgact tcggtcgtct caaccttgtt ttacgacaaa aaaatgagaa   2640

cgacgaatcc gaaagagact aagattgtga ttgacactac cggcagtacc aaacctaagc   2700

aggacgatct cattctcact tgtttcagag ggtgggtgaa gcagttgcaa atagattaca   2760

aaggcaacga aataatgacg gcagctgcct ctcaagggct gacccgtaaa ggtgtgtatg   2820

ccgttcggta caaggtgaat gaaaatcctc tgtacgcacc cacctcagaa catgtgaacg   2880

tcctactgac ccgcacggag gaccgcatcg tgtggaaaac actagccggc gacccatgga   2940

taaaaacact gactgccaag taccctggga atttcactgc cacgatagag gagtggcaag   3000

cagagcatga tgccatcatg aggcacatct tggagagacc ggaccctacc gacgtcttcc   3060

agaataaggc aaacgtgtgt tgggccaagg ctttagtgcc ggtgctgaag accgctggca   3120
```

tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgagggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460

-continued gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720
acattcatac actgtttgat atgtcggctg aagactttga cgctattata gccgagcact 6780
tccagcctgg ggattgtgtt ctggaaactg acatcgcgtc gtttgataaa agtgaggacg 6840
acgccatggc tctgaccgcg ttaatgattc tggaagactt aggtgtggac gcagagctgt 6900
tgacgctgat tgaggcggct ttcggcgaaa tttcatcaat acatttgccc actaaaacta 6960
aatttaaatt cggagccatg atgaaatctg gaatgttcct cacactgttt gtgaacacag 7020
tcattaacat tgtaatcgca agcagagtgt tgagagaacg gctaaccgga tcaccatgtg 7080
cagcattcat tggagatgac aatatcgtga aaggagtcaa atcggacaaa ttaatggcag 7140
acaggtgcgc cacctggttg aatatggaag tcaagattat agatgctgtg gtgggcgaga 7200
aagcgcctta tttctgtgga gggtttattt tgtgtgactc cgtgaccggc acagcgtgcc 7260
gtgtggcaga cccccctaaaa aggctgttta agcttggcaa acctctggca gcagacgatg 7320
aacatgatga tgacaggaga agggcattgc atgaagagtc aacacgctgg aaccgagtgg 7380
gtattctttc agagctgtgc aaggcagtag aatcaaggta tgaaaccgta ggaacttcca 7440
tcatagttat ggccatgact actctagcta gcagtgttaa atcattcagc tacctgagag 7500
gggcccctat aactctctac ggctaacctg aatggactac gacatagtct agtccgccaa 7560
gatgggcaag cggtccgccg gctctatcat gtggctggcc tctctggccg tggtcatcgc 7620
atgcgcagga gcagcggagg tcaccaggag aggcagcgcc tactatatgt acctggacag 7680
aaatgatgcc ggcgaggcca tcagctttcc caccacactg ggcatgaaca agtgttacat 7740
ccagatcatg gacctgggcc acatgtgcga tgccaccatg tcctatgagt gtccaatgct 7800
ggacgagggc gtggagcccg acgatgtgga ttgctggtgt aataccacat ccacatgggt 7860
ggtgtacggc acctgccacc acaagaaggg agaggcaagg cgctctcgga gagcagtgac 7920
actgccttcc cactctaccc ggaagctgca gacaagatct cagacctggc tggagagccg 7980
ggagtataca aagcacctga tccgggtgga gaactggatc tttagaaatc caggattcgc 8040
actggcagca gcagcaatcg catggctgct gggcagctcc acctcccaga aagtgatcta 8100
cctggtcatg atcctgctga tcgcccctgc ctattccatc aggtgcatcg gcgtgtctaa 8160
tcgcgacttc gtggagggca tgtctggcgg cacctgggtg gatgtggtgc tggagcacgg 8220
cggctgcgtg acagtgatgg cccaggacaa gccaaccgtg gacatcgagc tggtgaccac 8280
aaccgtgagc aacatggccg aggtgcggtc ctactgctat gaggccagca tctccgacat 8340
ggcctctgat agcagatgtc ccacccaggg cgaggcctac ctggacaagc agtctgatac 8400
acagtacgtg tgcaagagga ccctggtgga caggggatgg ggaaatggat gtggcctgtt 8460
tggcaagggc agcctggtga catgcgccaa gttcgcctgt tctaagaaga tgaccggcaa 8520
gagcatccag ccagagaacc tggagtaccg gatcatgctg agcgtgcacg gcagccagca 8580
ctccggcatg atcgtgaacg acacaggcca cgagacagat gagaataggg ccaaggtgga 8640
gatcacacct aacagcccac gcgccgaggc caccctggga ggatttggct ccctgggcct 8700
ggactgcgag cctagaacag gcctggactt ctccgatctg tactatctga ccatgaacaa 8760
taagcactgg ctggtgcaca aggagtggtt tcacgacatc ccactgccat ggcacgcagg 8820
agcagataca ggaaccccac actggaacaa taaggaggcc ctggtggagt tcaaggatgc 8880
ccacgccaag aggcagacag tggtggtgct gggcagccag gagggagcag tgcacaccgc 8940
cctggcaggc gccctggagg ccgagatgga cggagcaaag ggccgcctgt ctagcggcca 9000
cctgaagtgc cggctgaaga tggataagct gagactgaag ggcgtgtcct actctctgtg 9060
cacagccgcc ttcaccttca ccaagatccc tgccgagaca ctgcacggca cagtgaccgt 9120
ggaggtgcag tatgccggca cagacggccc ctgtaaggtg cctgcccaga tggccgtgga 9180
tatgcagaca ctgacccctg tgggcaggct gatcaccgcc aatccagtga tcacagagtc 9240
caccgagaac tctaagatga tgctggagct ggaccccccct tttggcgata gctatatcgt 9300
gatcggcgtg ggcgagaaga agatcacaca ccactggcac cgcagcggct ccacaatcgg 9360
caaggccttt gaggccaccg tgaggggagc aaagaggatg gccgtgctgg gcgacaccgc 9420
atgggatttc ggctccgtgg gaggcgccct gaactctctg ggcaagggca tccaccagat 9480
cttcggcgcc gcctttaagt ccctgttcgg cggcatgtct tggtttagcc agatcctgat 9540
cggcacactg ctgatgtggc tgggcctgaa caccaagaat ggctctatca gcctgatgtg 9600
cctggccctg ggaggcgtgc tgatcttcct gagcaccgcc gtgtccgcct gatgataagg 9660
cgcgcccacc cagcggccgc atacagcagc aattggcaag ctgcttacat agaactcgcg 9720
gcgattggca tgccgcctta aaatttttat tttatttttc ttttcttttc cgaatcggat 9780
tttgttttta atatttcaaa aaaaaaaaaa aaaaaaaaaa aaaaaaaaaa aaaaaaagaa 9840
gagcgtttaa acacgtgata tctggcctca tgggccttcc tttcactgcc cgctttccag 9900
tcgggaaacc tgtcgtgcca gctgcattaa catggtcata gctgtttcct tgcgtattgg 9960
gcgctctccg cttcctcgct cactgactcg ctgcgctcgg tcgttcgggt aaagcctggg 10020
gtgcctaatg agcaaaaggc cagcaaaagg ccaggaaccg taaaaaggcc gcgttgctgg 10080
cgtttttcca taggctccgc ccccctgacg agcatcacaa aaatcgacgc tcaagtcaga 10140
ggtggcgaaa cccgacagga ctataaagat accaggcgtt tcccccctgga agctccctcg 10200

```
tgcgctctcc tgttccgacc ctgccgctta ccggatacct gtccgccttt ctcccttcgg  10260
gaagcgtggc gctttctcat agctcacgct gtaggtatct cagttcggtg taggtcgttc  10320
gctccaagct gggctgtgtg cacgaacccc ccgttcagcc cgaccgctgc gccttatccg  10380
gtaactatcg tcttgagtcc aacccggtaa gacacgactt atcgccactg gcagcagcca  10440
ctggtaacag gattagcaga gcgaggtatg taggcggtgc tacagagttc ttgaagtggt  10500
ggcctaacta cggctacact agaagaacag tatttggtat ctgcgctctg ctgaagccag  10560
ttaccttcgg aaaaagagtt ggtagctctt gatccggcaa acaaaccacc gctggtagcg  10620
gtggtttttt tgtttgcaag cagcagatta cgcgcagaaa aaaaggatct caagaagatc  10680
ctttgatctt ttctacgggg tctgacgctc agtggaacga aaactcacgt taagggattt  10740
tggtcatgaa tacacggtgc ctgactgcgt tagcaattta actgtgataa actaccgcat  10800
taaagcttat cgatgataag ctgtcaaaca tgagaattct tagaaaaact catcgagcat  10860
caaatgaaac tgcaatttat tcatatcagg attatcaata ccatattttt gaaaaagccg  10920
tttctgtaat gaaggagaaa actcaccgag gcagttccat aggatggcaa gatcctggta  10980
tcggtctgcg attccgactc gtccaacatc aatacaacct attaatttcc cctcgtcaaa  11040
aataaggtta tcaagtgaga aatcaccatg agtgacgact gaatccggtg agaatggcaa  11100
aagcttatgc atttctttcc agacttgttc aacaggccag ccattacgct cgtcatcaaa  11160
atcactcgca tcaaccaaac cgttattcat tcgtgattgc gcctgagcga gacgaaatac  11220
gcgatcgctg ttaaaaggac aattacaaac aggaatcgaa tgcaaccggc gcaggaacac  11280
tgccagcgca tcaacaatat tttcacctga atcaggatat tcttctaata cctggaatgc  11340
tgttttcccg gggatcgcag tggtgagtaa ccatgcatca tcaggagtac ggataaaatg  11400
cttgatggtc ggaagaggca taaattccgt cagccagttt agtctgacca tctcatctgt  11460
aacatcattg gcaacgctac ctttgccatg tttcagaaac aactctggcg catcgggctt  11520
cccatacaat cgatagattg tcgcacctga ttgcccgaca ttatcgcgag cccatttata  11580
cccatataaa tcagcatcca tgttggaatt taatcgcggc ctcgagcaag acgtttcccg  11640
ttgaatatgg ctcataacac cccttgtatt actgtttatg taagcagaca gttttattgt  11700
tcatgagcgg atacatattt gaatgtattt agaaaaataa acaaataggg gttccgcgca  11760
catttccccg aaaagtgcca cctaaattgt aagcgttaat attttgttaa aattcgcgtt  11820
aaatttttgt taaatcagct cattttttaa ccaataggcc gaaatcggca aaatccctta  11880
taaatcaaaa gaatagaccg agatagggtt gagtggccgc tacagggcgc tcccattcgc  11940
cattcaggct gcgcaactgt tgggaagggc gtttcggtgc gggcctcttc gctattacgc  12000
cagctggcga aagggggatg tgctgcaagg cgattaagtt gggtaacgcc agggttttcc  12060
cagtcacacg cgtaatacga ctcactatag                                  12090
```

```
<210> SEQ ID NO 34
<211> LENGTH: 12090
<212> TYPE: DNA
<213> ORGANISM: Artificial Sequence
<220> FEATURE:
<223> OTHER INFORMATION: SAM vector backbone with ZIka antigen insert

<400> SEQUENCE: 34
ataggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
```

-continued

```
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccataggggt gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaaagggctg gacgtcaatg   2340
ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca aacagtgcgg ttttttttaac atgatgtgcc   2520
```

tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920

-continued

```
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
```

-continued

```
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgggcaag cggtccgccg gctctatcat gtggctggcc tctctggccg tggtcatcgc   7620
atgcgcagga gcagcggagg tcaccaggag aggcagcgcc tactatatgt acctggacag   7680
aaatgatgcc ggcgaggcca tcagctttcc caccacactg ggcatgaaca agtgttacat   7740
ccagatcatg gacctgggcc acatgtgcga tgccaccatg tcctatgagt gtccaatgct   7800
ggacgagggc gtggagcccg acgatgtgga ttgctggtgt aataccacat ccacatgggt   7860
ggtgtacggc acctgccacc acaagaaggg agaggcaagg cgctctcgga gagcagtgac   7920
actgccttcc cactctaccc ggaagctgca gacaagatct cagacctggc tggagagccg   7980
ggagtataca aagcacctga tccgggtgga gaactggatc tttagaaatc caggattcgc   8040
actggcagca gcagcaatcg catggctgct gggcagctcc acctcccaga aagtgatcta   8100
cctggtcatg atcctgctga tcgcccctgc ctattccatc aggtgcatcg gcgtgtctaa   8160
tcgcgacttc gtggagggca tgtctggcgg cacctgggtg gatgtggtgc tggagcacgg   8220
cggctgcgtg acagtgatgg cccaggacaa gccaaccgtg gacatcgagc tggtgaccac   8280
aaccgtgagc aacatggccg aggtgcggtc ctactgctat gaggccagca tctccgacat   8340
ggcctctgat agcagatgtc ccacccaggg cgaggcctac ctggacaagc agtctgatac   8400
acagtacgtg tgcaagagga ccctggtgga caggggatgg ggaaatggat gtggcctgtt   8460
tggcaagggc agcctggtga catgcgccaa gttcgcctgt tctaagaaga tgaccggcaa   8520
gagcatccag ccagagaacc tggagtaccg gatcatgctg agcgtgcacg gcagccagca   8580
ctccggcatg atcgtgaacg acacaggcca cgagacagat gagaataggg ccaaggtgga   8640
gatcacacct aacagcccac gcgccgaggc caccctggga ggatttggct ccctgggcct   8700
ggactgcgag cctagaacag gcctggactt ctccgatctg tactatctga ccatgaacaa   8760
taagcactgg ctggtgcaca aggagtggtt tcacgacatc ccactgccat ggcacgcagg   8820
agcagataca ggaaccccac actggaacaa taaggaggcc ctggtggagt tcaaggatgc   8880
ccacgccaag aggcagacag tggtggtgct gggcagccag gagggagcag tgcacaccgc   8940
cctggcaggc gccctggagg ccgagatgga cggagcaaag ggccgcctgt ctagcggcca   9000
cctgaagtgc cggctgaaga tggataagct gagactgaag ggcgtgtcct actctctgtg   9060
cacagccgcc ttcaccttca ccaagatccc tgccgagaca ctgcacggca cagtgaccgt   9120
ggaggtgcag tatgccggca cagacggccc ctgtaaggtg cctgcccaga tggccgtgga   9180
tatgcagaca ctgacccctg tgggcaggct gatcaccgcc aatccagtga tcacagagtc   9240
caccgagaac tctaagatga tgctggagct ggaccccccct tttggcgata gctatatcgt   9300
gatcggcgtg ggcgagaaga agatcacaca ccactggcac cgcagcggct ccaccctggg   9360
caaggccttt agcaccaccc tgaagggagc acagaggctg gccgccctgg gcgacaccgc   9420
atgggatttc ggctccatcg gaggcgtgtt caactctatc ggcaaggccg tgcaccaggt   9480
gttcggcggc gcctttcgga ccctgttcgg cggcatgtct tggatcaccc agggcctgat   9540
gggcgccctg ctgctgtgga tgggcgtgaa cgcccgggac cggtctatcg ccctggcctt   9600
cctggccacc ggaggcgtgc tggtgttcct ggccaccaac gtgcacgcct gatgataagg   9660
```

```
cgcgcccacc cagcggccgc atacagcagc aattggcaag ctgcttacat agaactcgcg   9720
gcgattggca tgccgcctta aaatttttat tttatttttc ttttcttttc cgaatcggat   9780
tttgttttta atatttcaaa aaaaaaaaaa aaaaaaaaaa aaaaaaaaaa aaaaaaagaa   9840
gagcgtttaa acacgtgata tctggcctca tgggccttcc tttcactgcc cgctttccag   9900
tcgggaaacc tgtcgtgcca gctgcattaa catggtcata gctgtttcct tgcgtattgg   9960
gcgctctccg cttcctcgct cactgactcg ctgcgctcgg tcgttcgggt aaagcctggg  10020
gtgcctaatg agcaaaaggc cagcaaaagg ccaggaaccg taaaaaggcc gcgttgctgg  10080
cgtttttcca taggctccgc ccccctgacg agcatcacaa aaatcgacgc tcaagtcaga  10140
ggtggcgaaa cccgacagga ctataaagat accaggcgtt tccccctgga agctccctcg  10200
tgcgctctcc tgttccgacc ctgccgctta ccggatacct gtccgccttt ctcccttcgg  10260
gaagcgtggc gctttctcat agctcacgct gtaggtatct cagttcggtg taggtcgttc  10320
gctccaagct gggctgtgtg cacgaacccc ccgttcagcc cgaccgctgc gccttatccg  10380
gtaactatcg tcttgagtcc aacccggtaa gacacgactt atcgccactg gcagcagcca  10440
ctggtaacag gattagcaga gcgaggtatg taggcggtgc tacagagttc ttgaagtggt  10500
ggcctaacta cggctacact agaagaacag tatttggtat ctgcgctctg ctgaagccag  10560
ttaccttcgg aaaaagagtt ggtagctctt gatccggcaa acaaaccacc gctggtagcg  10620
gtggtttttt tgtttgcaag cagcagatta cgcgcagaaa aaaaggatct caagaagatc  10680
ctttgatctt ttctacgggg tctgacgctc agtggaacga aaactcacgt taagggattt  10740
tggtcatgaa tacacggtgc ctgactgcgt tagcaattta actgtgataa actaccgcat  10800
taaagcttat cgatgataag ctgtcaaaca tgagaattct tagaaaaact catcgagcat  10860
caaatgaaac tgcaatttat tcatatcagg attatcaata ccatattttt gaaaaagccg  10920
tttctgtaat gaaggagaaa actcaccgag gcagttccat aggatggcaa gatcctggta  10980
tcggtctgcg attccgactc gtccaacatc aatacaacct attaatttcc cctcgtcaaa  11040
aataaggtta tcaagtgaga aatcaccatg agtgacgact gaatccggtg agaatggcaa  11100
aagcttatgc atttctttcc agacttgttc aacaggccag ccattacgct cgtcatcaaa  11160
atcactcgca tcaaccaaac cgttattcat tcgtgattgc gcctgagcga gacgaaatac  11220
gcgatcgctg ttaaaaggac aattacaaac aggaatcgaa tgcaaccggc gcaggaacac  11280
tgccagcgca tcaacaatat tttcacctga atcaggatat tcttctaata cctggaatgc  11340
tgttttcccg gggatcgcag tggtgagtaa ccatgcatca tcaggagtac ggataaaatg  11400
cttgatggtc ggaagaggca taaattccgt cagccagttt agtctgacca tctcatctgt  11460
aacatcattg gcaacgctac ctttgccatg tttcagaaac aactctggcg catcgggctt  11520
cccatacaat cgatagattg tcgcacctga ttgcccgaca ttatcgcgag cccatttata  11580
cccatataaa tcagcatcca tgttggaatt taatcgcggc ctcgagcaag acgtttcccg  11640
ttgaatatgg ctcataacac cccttgtatt actgtttatg taagcagaca gttttattgt  11700
tcatgagcgg atacatattt gaatgtattt agaaaaataa acaaataggg gttccgcgca  11760
catttccccg aaaagtgcca cctaaattgt aagcgttaat attttgttaa aattcgcgtt  11820
aaatttttgt taaatcagct cattttttaa ccaataggcc gaaatcggca aaatccctta  11880
taaatcaaaa gaatagaccg agatagggtt gagtggccgc tacagggcgc tcccattcgc  11940
cattcaggct gcgcaactgt tgggaagggc gtttcggtgc gggcctcttc gctattacgc  12000
```

```
cagctggcga aagggggatg tgctgcaagg cgattaagtt gggtaacgcc agggttttcc  12060

cagtcacacg cgtaatacga ctcactatag                                   12090


<210> SEQ ID NO 35
<211> LENGTH: 12081
<212> TYPE: DNA
<213> ORGANISM: Artificial Sequence
<220> FEATURE:
<223> OTHER INFORMATION: SAM vector backbone with ZIka antigen insert.

<400> SEQUENCE: 35

ataggcggcg catgagagaa gcccagacca attacctacc caaaatggag aaagttcacg     60

ttgacatcga ggaagacagc ccattcctca gagctttgca gcggagcttc ccgcagtttg    120

aggtagaagc caagcaggtc actgataatg accatgctaa tgccagagcg ttttcgcatc    180

tggcttcaaa actgatcgaa acggaggtgg acccatccga cacgatcctt gacattggaa    240

gtgcgcccgc ccgcagaatg tattctaagc acaagtatca ttgtatctgt ccgatgagat    300

gtgcggaaga tccggacaga ttgtataagt atgcaactaa gctgaagaaa aactgtaagg    360

aaataactga taaggaattg gacaagaaaa tgaaggagct cgccgccgtc atgagcgacc    420

ctgacctgga aactgagact atgtgcctcc acgacgacga gtcgtgtcgc tacgaagggc    480

aagtcgctgt ttaccaggat gtatacgcgg ttgacggacc gacaagtctc tatcaccaag    540

ccaataaggg agttagagtc gcctactgga taggctttga caccacccct tttatgttta    600

agaacttggc tggagcatat ccatcatact ctaccaactg ggccgacgaa accgtgttaa    660

cggctcgtaa cataggccta tgcagctctg acgttatgga gcggtcacgt agagggatgt    720

ccattcttag aaagaagtat ttgaaaccat ccaacaatgt tctattctct gttggctcga    780

ccatctacca cgagaagagg gacttactga ggagctggca cctgccgtct gtatttcact    840

tacgtggcaa gcaaaattac acatgtcggt gtgagactat agttagttgc gacgggtacg    900

tcgttaaaag aatagctatc agtccaggcc tgtatgggaa gccttcaggc tatgctgcta    960

cgatgcaccg cgagggattc ttgtgctgca aagtgacaga cacattgaac ggggagaggg   1020

tctcttttcc cgtgtgcacg tatgtgccag ctacattgtg tgaccaaatg actggcatac   1080

tggcaacaga tgtcagtgcg gacgacgcgc aaaaactgct ggttgggctc aaccagcgta   1140

tagtcgtcaa cggtcgcacc cagagaaaca ccaataccat gaaaaattac cttttgcccg   1200

tagtggccca ggcatttgct aggtgggcaa aggaatataa ggaagatcaa gaagatgaaa   1260

ggccactagg actacgagat agacagttag tcatggggtg ttgttgggct tttagaaggc   1320

acaagataac atctatttat aagcgcccgg atacccaaac catcatcaaa gtgaacagcg   1380

atttccactc attcgtgctg cccaggatag gcagtaacac attggagatc gggctgagaa   1440

caagaatcag gaaaatgtta gaggagcaca aggagccgtc acctctcatt accgccgagg   1500

acgtacaaga agctaagtgc gcagccgatg aggctaagga ggtgcgtgaa gccgaggagt   1560

tgcgcgcagc tctaccacct ttggcagctg atgttgagga gcccactctg gaagccgatg   1620

tcgacttgat gttacaagag gctggggccg gctcagtgga gacacctcgt ggcttgataa   1680

aggttaccag ctacgatggc gaggacaaga tcggctctta cgctgtgctt tctccgcagg   1740

ctgtactcaa gagtgaaaaa ttatcttgca tccaccctct cgctgaacaa gtcatagtga   1800

taacacactc tggccgaaaa gggcgttatg ccgtggaacc ataccatggt aaagtagtgg   1860

tgccagaggg acatgcaata cccgtccagg actttcaagc tctgagtgaa agtgccacca   1920

ttgtgtacaa cgaacgtgag ttcgtaaaca ggtacctgca ccatattgcc acacatggag   1980
```

-continued gagcgctgaa cactgatgaa gaatattaca aaactgtcaa gcccagcgag cacgacggcg 2040
aatacctgta cgacatcgac aggaaacagt gcgtcaagaa agaactagtc actgggctag 2100
ggctcacagg cgagctggtg gatcctccct tccatgaatt cgcctacgag agtctgagaa 2160
cacgaccagc cgctccttac caagtaccaa ccatagggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg ttttttaac atgatgtgcc 2520 tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg acttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggaggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440
cagatgtagc catatactgc agggacaaga aatgggaaat gactctcaag gaagcagtgg 4500
ctaggagaga agcagtggag gagatatgca tatccgacga ctcttcagtg acagaacctg 4560
atgcagagct ggtgagggtg catccgaaga gttctttggc tggaaggaag ggctacagca 4620
caagcgatgg caaaactttc tcatatttgg aagggaccaa gtttcaccag gcggccaagg 4680
atatagcaga aattaatgcc atgtggcccg ttgcaacgga ggccaatgag caggtatgca 4740
tgtatatcct cggagaaagc atgagcagta ttaggtcgaa atgccccgtc gaagagtcgg 4800
aagcctccac accacctagc acgctgcctt gcttgtgcat ccatgccatg actccagaaa 4860
gagtacagcg cctaaaagcc tcacgtccag aacaaattac tgtgtgctca tcctttccat 4920
tgccgaagta tagaatcact ggtgtgcaga agatccaatg ctcccagcct atattgttct 4980
caccgaaagt gcctgcgtat attcatccaa ggaagtatct cgtggaaaca ccaccggtag 5040
acgagactcc ggagccatcg gcagagaacc aatccacaga ggggacacct gaacaaccac 5100
cacttataac cgaggatgag accaggacta gaacgcctga gccgatcatc atcgaagagg 5160
aagaagagga tagcataagt ttgctgtcag atggcccgac ccaccaggtg ctgcaagtcg 5220
aggcagacat tcacgggccg ccctctgtat ctagctcatc ctggtccatt cctcatgcat 5280
ccgactttga tgtggacagt ttatccatac ttgacaccct ggagggagct agcgtgacca 5340
gcggggcaac gtcagccgag actaactctt acttcgcaaa gagtatggag tttctggcgc 5400
gaccggtgcc tgcgcctcga acagtattca ggaaccctcc acatcccgct ccgcgcacaa 5460
gaacaccgtc acttgcaccc agcagggcct gctcgagaac cagcctagtt tccaccccgc 5520
caggcgtgaa tagggtgatc actagagagg agctcgaggc gcttaccccg tcacgcactc 5580
ctagcaggtc ggtctcgaga accagcctgg tctccaaccc gccaggcgta aatagggtga 5640
ttacaagaga ggagtttgag gcgttcgtag cacaacaaca atgacggttt gatgcgggtg 5700
catacatctt ttcctccgac accggtcaag ggcatttaca acaaaaatca gtaaggcaaa 5760
cggtgctatc cgaagtggtg ttggagagga ccgaattgga gatttcgtat gccccgcgcc 5820
tcgaccaaga aaaagaagaa ttactacgca agaaattaca gttaaatccc acacctgcta 5880
acagaagcag ataccagtcc aggaaggtgg agaacatgaa agccataaca gctagacgta 5940
ttctgcaagg cctagggcat tatttgaagg cagaaggaaa agtggagtgc taccgaaccc 6000
tgcatcctgt tcctttgtat tcatctagtg tgaaccgtgc cttttcaagc cccaaggtcg 6060
cagtggaagc ctgtaacgcc atgttgaaag agaactttcc gactgtggct tcttactgta 6120
ttattccaga gtacgatgcc tatttggaca tggttgacgg agcttcatgc tgcttagaca 6180
ctgccagttt ttgccctgca aagctgcgca gctttccaaa gaaacactcc tatttggaac 6240
ccacaatacg atcggcagtg ccttcagcga tccagaacac gctccagaac gtcctggcag 6300
ctgccacaaa aagaaattgc aatgtcacgc aaatgagaga attgcccgta ttggattcgg 6360
cggcctttaa tgtggaatgc ttcaagaaat atgcgtgtaa taatgaatat tgggaaacgt 6420
ttaaagaaaa ccccatcagg cttactgaag aaaacgtggt aaattacatt accaaattaa 6480
aaggaccaaa agctgctgct ctttttgcga agacacataa tttgaatatg ttgcaggaca 6540
taccaatgga caggtttgta atggacttaa agagagacgt gaaagtgact ccaggaacaa 6600
aacatactga agaacggccc aaggtacagg tgatccaggc tgccgatccg ctagcaacag 6660
cgtatctgtg cggaatccac cgagagctgg ttaggagatt aaatgcggtc ctgcttccga 6720

-continued

```
acattcatac actgtttgat atgtcggctg aagactttga cgctattata gccgagcact   6780
tccagcctgg ggattgtgtt ctggaaactg acatcgcgtc gtttgataaa agtgaggacg   6840
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgggcaag cggtccgccg gctctatcat gtggctggcc tctctggccg tggtcatcgc   7620
atgcgcagga gcaaccagga gaggcagcgc ctactatatg tacctggaca gaaatgatgc   7680
cggcgaggcc atcagctttc ccaccacact gggcatgaac aagtgttaca tccagatcat   7740
ggacctgggc cacatgtgcg atgccaccat gtcctatgag tgtccaatgc tggacgaggg   7800
cgtggagccc gacgatgtgg attgctggtg taataccaca tccacatggg tggtgtacgg   7860
cacctgccac cacaagaagg gagaggcaag gcgctctcgg agagcagtga cactgccttc   7920
ccactctacc cggaagctgc agacaagatc tcagacctgg ctggagagcc gggagtatac   7980
aaagcacctg atccgggtgg agaactggat ctttagaaat ccaggattcg cactggcagc   8040
agcagcaatc gcatggctgc tgggcagctc cacctcccag aaagtgatct acctggtcat   8100
gatcctgctg atcgcccctg cctattccat caggtgcatc ggcgtgtcta atcgcgactt   8160
cgtggagggc atgtctggcg gcacctgggt ggatgtggtg ctggagcacg gcggctgcgt   8220
gacagtgatg gcccaggaca agccaaccgt ggacatcgag ctggtgacca caaccgtgag   8280
caacatggcc gaggtgcggt cctactgcta tgaggccagc atctccgaca tggcctctga   8340
tagcagatgt cccacccagg gcgaggccta cctggacaag cagtctgata cacagtacgt   8400
gtgcaagagg accctggtgg acaggggatg gggaaatgga tgtggcctgt ttggcaaggg   8460
cagcctggtg acatgcgcca agttcgcctg ttctaagaag atgaccggca agagcatcca   8520
gccagagaac ctggagtacc ggatcatgct gagcgtgcac ggcagccagc actccggcat   8580
gatcgtgaac gacacaggcc acgagacaga tgagaatagg gccaaggtgg agatcacacc   8640
taacagccca cgcgccgagg ccaccctggg aggatttggc tccctgggcc tggactgcga   8700
gcctagaaca ggcctggact tctccgatct gtactatctg accatgaaca ataagcactg   8760
gctggtgcac aaggagtggt ttcacgacat ccccactgcca tggcacgcag gagcagatac   8820
aggaacccca cactggaaca ataaggaggc cctggtggag ttcaaggatg cccacgccaa   8880
gaggcagaca gtggtggtgc tgggcagcca ggagggagca gtgcacaccg ccctggcagg   8940
cgccctggag gccgagatgg acggagcaaa gggccgcctg tctagcggcc acctgaagtg   9000
ccggctgaag atggataagc tgagactgaa gggcgtgtcc tactctctgt gcacagccgc   9060
```

-continued

```
cttcaccttc accaagatcc ctgccgagac actgcacggc acagtgaccg tggaggtgca   9120
gtatgccggc acagacggcc cctgtaaggt gcctgcccag atggccgtgg atatgcagac   9180
actgacccct gtgggcaggc tgatcaccgc caatccagtg atcacagagt ccaccgagaa   9240
ctctaagatg atgctggagc tggacccccc ttttggcgat agctatatcg tgatcggcgt   9300
gggcgagaag aagatcacac accactggca ccgcagcggc tccacaatcg gcaaggcctt   9360
tgaggccacc gtgaggggag caaagaggat ggccgtgctg ggcgacaccg catgggattt   9420
cggctccgtg ggaggcgccc tgaactctct gggcaagggc atccaccaga tcttcggcgc   9480
cgcctttaag tccctgttcg gcggcatgtc ttggtttagc cagatcctga tcggcacact   9540
gctgatgtgg ctgggcctga acaccaagaa tggctctatc agcctgatgt gcctggccct   9600
gggaggcgtg ctgatcttcc tgagcaccgc cgtgtccgcc tgatgataag gcgcgcccac   9660
ccagcggccg catacagcag caattggcaa gctgcttaca tagaactcgc ggcgattggc   9720
atgccgcctt aaaattttta ttttattttt cttttctttt ccgaatcgga ttttgttttt   9780
aatatttcaa aaaaaaaaaa aaaaaaaaaa aaaaaaaaaa aaaaaaaaga agagcgttta   9840
aacacgtgat atctggcctc atgggccttc ctttcactgc ccgctttcca gtcgggaaac   9900
ctgtcgtgcc agctgcatta acatggtcat agctgtttcc ttgcgtattg ggcgctctcc   9960
gcttcctcgc tcactgactc gctgcgctcg gtcgttcggg taaagcctgg ggtgcctaat  10020
gagcaaaagg ccagcaaaag gccaggaacc gtaaaaaggc cgcgttgctg gcgtttttcc  10080
ataggctccg cccccctgac gagcatcaca aaaatcgacg ctcaagtcag aggtggcgaa  10140
acccgacagg actataaaga taccaggcgt ttccccctgg aagctccctc gtgcgctctc  10200
ctgttccgac cctgccgctt accggatacc tgtccgcctt tctcccttcg ggaagcgtgg  10260
cgctttctca tagctcacgc tgtaggtatc tcagttcggt gtaggtcgtt cgctccaagc  10320
tgggctgtgt gcacgaaccc cccgttcagc ccgaccgctg cgccttatcc ggtaactatc  10380
gtcttgagtc caacccggta agacacgact tatcgccact ggcagcagcc actggtaaca  10440
ggattagcag agcgaggtat gtaggcggtg ctacagagtt cttgaagtgg tggcctaact  10500
acggctacac tagaagaaca gtatttggta tctgcgctct gctgaagcca gttaccttcg  10560
gaaaaagagt tggtagctct tgatccggca aacaaaccac cgctggtagc ggtggttttt  10620
ttgtttgcaa gcagcagatt acgcgcagaa aaaaaggatc tcaagaagat cctttgatct  10680
tttctacggg gtctgacgct cagtggaacg aaaactcacg ttaagggatt ttggtcatga  10740
atacacggtg cctgactgcg ttagcaattt aactgtgata aactaccgca ttaaagctta  10800
tcgatgataa gctgtcaaac atgagaattc ttagaaaaac tcatcgagca tcaaatgaaa  10860
ctgcaattta ttcatatcag gattatcaat accatatttt tgaaaaagcc gtttctgtaa  10920
tgaaggagaa aactcaccga ggcagttcca taggatggca agatcctggt atcggtctgc  10980
gattccgact cgtccaacat caatacaacc tattaatttc ccctcgtcaa aaataaggtt  11040
atcaagtgag aaatcaccat gagtgacgac tgaatccggt gagaatggca aaagcttatg  11100
catttctttc cagacttgtt caacaggcca gccattacgc tcgtcatcaa aatcactcgc  11160
atcaaccaaa ccgttattca ttcgtgattg cgcctgagcg agacgaaata cgcgatcgct  11220
gttaaaagga caattacaaa caggaatcga atgcaaccgg cgcaggaaca ctgccagcgc  11280
atcaacaata ttttcacctg aatcaggata ttcttctaat acctggaatg ctgttttccc  11340
ggggatcgca gtggtgagta accatgcatc atcaggagta cggataaaat gcttgatggt  11400
cggaagaggc ataaattccg tcagccagtt tagtctgacc atctcatctg taacatcatt  11460
```

ggcaacgcta cctttgccat gtttcagaaa caactctggc gcatcgggct tcccatacaa 11520
tcgatagatt gtcgcacctg attgcccgac attatcgcga gcccatttat acccatataa 11580
atcagcatcc atgttggaat ttaatcgcgg cctcgagcaa gacgtttccc gttgaatatg 11640
gctcataaca ccccttgtat tactgtttat gtaagcagac agttttattg ttcatgagcg 11700
gatacatatt tgaatgtatt tagaaaaata aacaaatagg ggttccgcgc acatttcccc 11760
gaaaagtgcc acctaaattg taagcgttaa tattttgtta aaattcgcgt taaatttttg 11820
ttaaatcagc tcatttttta accaataggc cgaaatcggc aaaatccctt ataaatcaaa 11880
agaatagacc gagatagggt tgagtggccg ctacagggcg ctcccattcg ccattcaggc 11940
tgcgcaactg ttgggaaggg cgtttcggtg cgggcctctt cgctattacg ccagctggcg 12000
aaagggggat gtgctgcaag gcgattaagt tgggtaacgc cagggttttc ccagtcacac 12060
gcgtaatacg actcactata g 12081

<210> SEQ ID NO 36
<211> LENGTH: 12090
<212> TYPE: RNA
<213> ORGANISM: Artificial Sequence
<220> FEATURE:
<223> OTHER INFORMATION: SAM vector backbone with Zika antigen insert.

<400> SEQUENCE: 36
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380

-continued

```
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccugguggguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
```

ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120

-continued uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gaugggcaag cgguccgccg gcucuaucau guggcuggcc ucucuggccg uggucaucgc 7620
augcgcagga gcagcggagg ucaccaggag aggcagcgcc uacuauaugu accuggacag 7680
aaaugaugcc ggcgaggcca ucagcuuucc caccacacug ggcaugaaca aguguuacau 7740
ccagaucaug gaccugggcc acaugugcga ugccaccaug uccuaugagu guccaaugcu 7800
ggacgagggc guggagcccg acgaugugga uugcuggugu aauaccacau ccacaugggu 7860
gguguacggc accugccacc acaagaaggg agaggcaagg cgcucucgga gagcagugac 7920
acugccuucc cacucuaccc ggaagcugca gacaagaucu cagaccuggc uggagagccg 7980
ggaguauaca aagcaccuga uccgggugga gaacuggauc uuuagaaauc caggauucgc 8040
acuggcagca gcagcaaucg cauggcugcu gggcagcucc accucccaga aagugaucua 8100
ccuggucaug auccugcuga ucgccccugc cuauuccauc aggugcaucg gcgugucuaa 8160
ucgcgacuuc guggagggca ugucuggcgg caccugggug gauguggugc uggagcacgg 8220
cggcugcgug acagugaugg cccaggacaa gccaaccgug gacaucgagc uggugaccac 8280
aaccgugagc aacauggccg aggugcgguc cuacugcuau gaggccagca ucuccgacau 8340
ggccucugau agcagauguc ccacccaggg cgaggccuac cuggacaagc agucugauac 8400
acaguacgug ugcaagagga cccuggugga caggggaugg ggaaauggau guggccuguu 8460
uggcaagggc agccugguga caugcgccaa guucgccugu ucuaagaaga ugaccggcaa 8520

```
gagcauccag ccagagaacc uggaguaccg gaucaugcug agcgugcacg gcagccagca   8580
cuccggcaug aucgugaacg acacaggcca cgagacagau gagaauaggg ccaaggugga   8640
gaucacaccu aacagcccac gcgccgaggc cacccuggga ggauuuggcu cccugggccu   8700
ggacugcgag ccuagaacag gccuggacuu cuccgaucug uacuaucuga ccaugaacaa   8760
uaagcacugg cuggugcaca aggaguggu ucacgacauc ccacugccau ggcacgcagg   8820
agcagauaca ggaaccccac acuggaacaa uaaggaggcc cugguggagu ucaaggaugc   8880
ccacgccaag aggcagacag ugguggugcu gggcagccag gagggagcag ugcacaccgc   8940
ccuggcaggc gcccuggagg ccgagaugga cggagcaaag ggccgccugu cuagcggcca   9000
ccugaagugc cggcugaaga uggauaagcu gagacugaag ggcguguccu acucucugug   9060
cacagccgcc uucaccuuca ccaagauccc ugccgagaca cugcacggca cagugaccgu   9120
ggaggugcag uaugccggca cagacggccc cuguaaggug ccugcccaga uggccgugga   9180
uaugcagaca cugaccccug ugggcaggcu gaucaccgcc aauccaguga ucacagaguc   9240
caccgagaac ucuaagauga ugcuggagcu ggaccccccu uuuggcgaua gcuauaucgu   9300
gaucggcgug ggcgagaaga agaucacaca ccacuggcac cgcagcggcu ccacaaucgg   9360
caaggccuuu gaggccaccg ugaggggagc aaagaggaug gccgugcugg gcgacaccgc   9420
augggauuuc ggcuccgugg gaggcgcccu gaacucucug ggcaagggca uccaccagau   9480
cuucggcgcc gccuuuaagu cccuguucgg cggcaugucu ugguuuagcc agauccugau   9540
cggcacacug cugauguggc ugggccugaa caccaagaau ggcucuauca gccugaugug   9600
ccuggcccug ggaggcgugc ugaucuuccu gagcaccgcc guguccgccu gaugauaagg   9660
cgcgcccacc cagcggccgc auacagcagc aauuggcaag cugcuuacau agaacucgcg   9720
gcgauuggca ugccgccuua aaauuuuuau uuuauuuuuc uuuucuuuuc cgaaucggau   9780
uuuguuuuua auauuucaaa aaaaaaaaaa aaaaaaaaaa aaaaaaaaaa aaaaaaagaa   9840
gagcguuuaa acacgugaua ucuggccuca ugggccuucc uuucacugcc cgcuuuccag   9900
ucgggaaacc ugucgugcca gcugcauuaa cauggucaua gcuguuuccu ugcguauugg   9960
gcgcucuccg cuuccucgcu cacugacucg cugcgcucgg ucguucgggu aaagccuggg  10020
gugccuaaug agcaaaaggc cagcaaaagg ccaggaaccg uaaaaaggcc gcguugcugg  10080
cguuuuucca uaggcuccgc cccccugacg agcaucacaa aaaucgacgc ucaagucaga  10140
gguggcgaaa cccgacagga cuauaaagau accaggcguu ucccccugga agcucccucg  10200
ugcgcucucc uguuccgacc cugccgcuua ccggauaccu guccgccuuu cucccuucgg  10260
gaagcguggc gcuuucucau agcucacgcu guagguaucu caguucggug uaggucguuc  10320
gcuccaagcu gggcugugug cacgaacccc ccguucagcc cgaccgcugc gccuuauccg  10380
guaacuaucg ucuugagucc aacccgguaa gacacgacuu aucgccacug gcagcagcca  10440
cugguaacag gauuagcaga gcgagguaug uaggcggugc uacagaguuc uugaaguggu  10500
ggccuaacua cggcuacacu agaagaacag uauuugguau cugcgcucug cugaagccag  10560
uuaccuucgg aaaaagaguu gguagcucuu gauccggcaa acaaaccacc gcugguagcg  10620
gugguuuuuu uguuugcaag cagcagauua cgcgcagaaa aaaaggaucu caagaagauc  10680
cuuugaucuu uucuacgggg ucugacgcuc aguggaacga aaacucacgu uaagggauuu  10740
uggucaugaa uacacggugc cugacugcgu uagcaauuua acugugauaa acuaccgcau  10800
uaaagcuuau cgaugauaag cugucaaaca ugagaauucu uagaaaaacu caucgagcau  10860
```

-continued caaaugaaac ugcaauuuau ucauaucagg auuaucaaua ccauauuuuu gaaaaagccg 10920
uuucuguaau gaaggagaaa acucaccgag gcaguuccau aggauggcaa gauccuggua 10980
ucggucugcg auuccgacuc guccaacauc aauacaaccu auuaauuucc ccucgucaaa 11040
aauaagguua ucaagugaga aaucaccaug agugacgacu gaauccggug agaauggcaa 11100
aagcuuaugc auuucuuucc agacuuguuc aacaggccag ccauuacgcu cgucaucaaa 11160
aucacucgca ucaaccaaac cguuauucau ucgugauugc gccugagcga gacgaaauac 11220
gcgaucgcug uuaaaaggac aauuacaaac aggaaucgaa ugcaaccggc gcaggaacac 11280
ugccagcgca ucaacaauau uuucaccuga aucaggauau ucuucuaaua ccuggaaugc 11340
uguuuucccg gggaucgcag uggugaguaa ccaugcauca ucaggaguac ggauaaaaug 11400
cuugaugguc ggaagaggca uaaauuccgu cagccaguuu agucugacca ucucaucugu 11460
aacaucauug gcaacgcuac cuuugccaug uuucagaaac aacucuggcg caucgggcuu 11520
cccauacaau cgauagauug ucgcaccuga uugcccgaca uuaucgcgag cccauuuaua 11580
cccauauaaa ucagcaucca uguuggaauu uaaucgcggc cucgagcaag acguuucccg 11640
uugaauaugg cucauaacac cccuuguauu acuguuuaug uaagcagaca guuuuauugu 11700
ucaugagcgg auacauauuu gaauguauuu agaaaaauaa acaaauaggg guuccgcgca 11760
cauuuccccg aaaagugcca ccuaaauugu aagcguuaau auuuuguuaa aauucgcguu 11820
aaauuuuugu uaaaucagcu cauuuuuuaa ccaauaggcc gaaaucggca aaaucccuua 11880
uaaaucaaaa gaauagaccg agauaggguu gaguggccgc uacagggcgc ucccauucgc 11940
cauucaggcu gcgcaacugu ugggaagggc guuucggugc gggccucuuc gcuauuacgc 12000
cagcuggcga aagggggaug ugcugcaagg cgauuaaguu ggguaacgcc aggguuuucc 12060
cagucacacg cguaauacga cucacuauag 12090

<210> SEQ ID NO 37
<211> LENGTH: 12090
<212> TYPE: RNA
<213> ORGANISM: Artificial Sequence
<220> FEATURE:
<223> OTHER INFORMATION: SAM vector background with Zika antigen insert.

<400> SEQUENCE: 37
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840

-continued

```
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
```

-continued

```
cagcagagau aguauugaac caacuaugcg ugagguucuu uggacucgau cuggacuccg   3240

gucuauuuuc ugcacccacu guuccguuau ccauuaggaa uaaucacugg gauaacuccc   3300

cgucgccuaa cauguacggg cugaauaaag aaguggucccg ucagcucucu cgcagguacc   3360

cacaacugcc ucgggcaguu gccacuggaa gagucuauga caugaacacu gguacacugc   3420

gcaauuauga uccgcgcaua aaccuaguac cuguaaacag aagacugccu caugcuuuag   3480

uccuccacca uaaugaacac ccacagagug acuuuucuuc auucgucagc aaauugaagg   3540

gcagaacugu ccuggugguc ggggaaaagu uguccguccc aggcaaaaug guugacuggu   3600

ugucagaccg gccugaggcu accuucagag cucggcugga uuuaggcauc ccaggugaug   3660

ugcccaaaua ugacauaaua uuuguuaaug ugaggacccc auauaaauac caucacuauc   3720

agcaguguga agaccaugcc auuaagcuua gcauguugac caagaaagcu ugucugcauc   3780

ugaaucccgg cggaaccugu gucagcauag guuaugguua cgcugacagg gccagcgaaa   3840

gcaucauugg ugcuauagcg cggcaguuca aguuuucccg gguaugcaaa ccgaaauccu   3900

cacuugaaga gacggaaguu cuguuuguau ucauugggua cgaucgcaag gcccguacgc   3960

acaauccuua caagcuuuca ucaaccuuga ccaacauuua uacagguucc agacuccacg   4020

aagccggaug ugcacccuca uaucaugugg ugcgagggga uauugccacg gccaccgaag   4080

gagugauuau aaaugcugcu aacagcaaag gacaaccugg cggagggggug ugcggagcgc   4140

uguauaagaa auucccggaa agcuucgauu uacagccgau cgaaguagga aaagcgcgac   4200

uggucaaagg ugcagcuaaa cauaucauuc augccguagg accaaacuuc aacaaaguuu   4260

cggagguuga aggugacaaa caguuggcag aggcuuauga guccaucgcu aagauuguca   4320

acgauaacaa uuacaaguca guagcgauuc cacuguuguc caccggcauc uuuuccggga   4380

acaaagaucg acuaacccaa ucauugaacc auuugcugac agcuuuagac accacugaug   4440

cagauguagc cauauacugc agggacaaga aaugggaaau gacucucaag gaagcagugg   4500

cuaggagaga agcaguggag gagauaugca uauccgacga cucuucagug acagaaccug   4560

augcagagcu ggugagggug cauccgaaga guucuuuggc uggaaggaag ggcuacagca   4620

caagcgaugg caaaacuuuc ucauauuugg aagggaccaa guuucaccag gcggccaagg   4680

auauagcaga aauuaaugcc auguggcccg uugcaacgga ggccaaugag cagguaugca   4740

uguauauccu cggagaaagc augagcagua uuaggucgaa augccccguc gaagagucgg   4800

aagccuccac accaccuagc acgcugccuu gcuugugcau ccaugccaug acuccagaaa   4860

gaguacagcg ccuaaaagcc ucacguccag aacaaauuac ugugugcuca uccuuuccau   4920

ugccgaagua uagaaucacu ggugugcaga agauccaaug cucccagccu auauuguucu   4980

caccgaaagu gccugcguau auucauccaa ggaaguaucu cguggaaaca ccaccgguag   5040

acgagacucc ggagccaucg gcagagaacc aauccacaga ggggacaccu gaacaaccac   5100

cacuuauaac cgaggaugag accaggacua gaacgccuga gccgaucauc aucgaagagg   5160

aagaagagga uagcauaagu uugcugucag auggcccgac ccaccaggug cugcaagucg   5220

aggcagacau ucacgggccg cccucuguau cuagcucauc cugguccauu ccucaugcau   5280

ccgacuuuga uguggacagu uuauccauac uugacacccu ggagggagcu agcgugacca   5340

gcggggcaac gucagccgag acuaacucuu acuucgcaaa gaguauggag uuucuggcgc   5400

gaccggugcc ugcgccucga acaguauuca ggaacccucc acaucccgcu ccgcgcacaa   5460

gaacaccguc acuugcaccc agcagggccu gcucgagaac cagccuaguu uccaccccgc   5520

caggcgugaa uagggugauc acuagagagg agcucgaggc gcuuaccccg ucacgcacuc   5580
```

-continued

```
cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu aggugugggac gcagagcugu   6900
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
gaugggcaag cgguccgccg gcucuaucau guggcuggcc ucucuggccg uggucaucgc   7620
augcgcagga gcagcggagg ucaccaggag aggcagcgcc uacuauaugu accuggacag   7680
aaaugaugcc ggcgaggcca ucagcuuucc caccacacug ggcaugaaca aguguuacau   7740
ccagaucaug gaccugggcc acaugugcga ugccaccaug uccuaugagu guccaaugcu   7800
ggacgagggc guggagcccg acgaugugga uugcuggugu aauaccacau ccacaugggu   7860
gguguacggc accugccacc acaagaaggg agaggcaagg cgcucucgga gagcagugac   7920
```

-continued acugccuucc cacucuaccc ggaagcugca gacaagaucu cagaccuggc uggagagccg 7980
ggaguauaca aagcaccuga uccgggugga gaacuggauc uuuagaaauc caggauucgc 8040
acuggcagca gcagcaaucg cauggcugcu gggcagcucc accucccaga aagugaucua 8100
ccuggucaug auccugcuga ucgccccugc cuauuccauc aggugcaucg gcgugucuaa 8160
ucgcgacuuc guggagggca ugucuggcgg caccugggug gauguggugc uggagcacgg 8220
cggcugcgug acagugaugg cccaggacaa gccaaccgug gacaucgagc uggugaccac 8280
aaccgugagc aacauggccg aggugcgguc cuacugcuau gaggccagca ucuccgacau 8340
ggccucugau agcagauguc ccacccaggg cgaggccuac cuggacaagc agucugauac 8400
acaguacgug ugcaagagga cccuggugga caggggaugg ggaaauggau guggccuguu 8460
uggcaagggc agccugguga caugcgccaa guucgccugu ucuaagaaga ugaccggcaa 8520
gagcauccag ccagagaacc uggaguaccg gaucaugcug agcgugcacg gcagccagca 8580
cuccggcaug aucgugaacg acacaggcca cgagacagau gagaauaggg ccaaggugga 8640
gaucacaccu aacagcccac gcgccgaggc cacccuggga ggauuuggcu cccugggccu 8700
ggacugcgag ccuagaacag gccuggacuu cuccgaucug uacuaucuga ccaugaacaa 8760
uaagcacugg cuggugcaca aggagugguu ucacgacauc ccacugccau ggcacgcagg 8820
agcagauaca ggaaccccac acuggaacaa uaaggaggcc cugguggagu ucaaggaugc 8880
ccacgccaag aggcagacag ugguggugcu gggcagccag gagggagcag ugcacaccgc 8940
ccuggcaggc gcccuggagg ccgagaugga cggagcaaag ggccgccugu cuagcggcca 9000
ccugaagugc cggcugaaga uggauaagcu gagacugaag ggcguguccu acucucugug 9060
cacagccgcc uucaccuuca ccaagauccc ugccgagaca cugcacggca cagugaccgu 9120
ggaggugcag uaugccggca cagacggccc cuguaaggug ccugcccaga uggccgugga 9180
uaugcagaca cugaccccug ugggcaggcu gaucaccgcc aauccaguga ucacagaguc 9240
caccgagaac ucuaagauga ugcuggagcu ggacccccccu uuuggcgaua gcuauaucgu 9300
gaucggcgug ggcgagaaga agaucacaca ccacuggcac cgcagcggcu ccacccuggg 9360
caaggccuuu agcaccaccc ugaagggagc acagaggcug gccgcccugg gcgacaccgc 9420
augggauuuc ggcuccaucg gaggcguguu caacucuauc ggcaaggccg ugcaccaggu 9480
guucggcggc gccuuucgga cccuguucgg cggcaugucu uggaucaccc agggccugau 9540
gggcgcccug cugcugugga ugggcgugaa cgcccgggac cggucuaucg cccuggccuu 9600
ccuggccacc ggaggcgugc ugguguuccu ggccaccaac gugcacgccu gaugauaagg 9660
cgcgcccacc cagcggccgc auacagcagc aauuggcaag cugcuuacau agaacucgcg 9720
gcgauuggca ugccgccuua aaauuuuuau uuuauuuuuc uuuucuuuuc cgaaucggau 9780
uuuguuuuua auauuucaaa aaaaaaaaaa aaaaaaaaaa aaaaaaaaaa aaaaaaagaa 9840
gagcguuuaa acacgugaua ucuggccuca ugggccuucc uuucacugcc cgcuuuccag 9900
ucgggaaacc ugucgugcca gcugcauuaa cauggucaua gcuguuuccu ugcguauugg 9960
gcgcucuccg cuuccucgcu cacugacucg cugcgcucgg ucguucgggu aaagccuggg 10020
gugccuaaug agcaaaaggc cagcaaaagg ccaggaaccg uaaaaaggcc gcguugcugg 10080
cguuuuucca uaggcuccgc ccccccugacg agcaucacaa aaaucgacgc ucaagucaga 10140
gguggcgaaa cccgacagga cuauaaagau accaggcguu ucccccugga agcucccucg 10200
ugcgcucucc uguuccgacc cugccgcuua ccggauaccu guccgccuuu cucccuucgg 10260
gaagcguggc gcuuucucau agcucacgcu guagguaucu caguucggug uaggucguuc 10320
gcuccaagcu gggcugugug cacgaacccc ccguucagcc cgaccgcugc gccuuauccg 10380
guaacuaucg ucuugagucc aacccgguaa gacacgacuu aucgccacug gcagcagcca 10440
cugguaacag gauuagcaga gcgagguaug uaggcggugc uacagaguuc uugaaguggu 10500
ggccuaacua cggcuacacu agaagaacag uauuugguau cugcgcucug cugaagccag 10560
uuaccuucgg aaaaagaguu gguagcucuu gauccggcaa acaaaccacc gcugguagcg 10620
gugguuuuuu uguuugcaag cagcagauua cgcgcagaaa aaaaggaucu caagaagauc 10680
cuuugaucuu uucuacgggg ucugacgcuc aguggaacga aaacucacgu uaagggauuu 10740
uggucaugaa uacacggugc cugacugcgu uagcaauuua acugugauaa acuaccgcau 10800
uaaagcuuau cgaugauaag cugucaaaca ugagaauucu uagaaaaacu caucgagcau 10860
caaaugaaac ugcaauuuau ucauaucagg auuaucaaua ccauauuuuu gaaaaagccg 10920
uuucuguaau gaaggagaaa acucaccgag gcaguuccau aggauggcaa gauccuggua 10980
ucggucugcg auuccgacuc guccaacauc aauacaaccu auuaauuucc ccucgucaaa 11040
aauaagguua ucaagugaga aaucaccaug agugacgacu gaauccggug agaauggcaa 11100
aagcuuaugc auuucuuucc agacuuguuc aacaggccag ccauuacgcu cgucaucaaa 11160
aucacucgca ucaaccaaac cguuauucau ucgugauugc gccugagcga gacgaaauac 11220
gcgaucgcug uuaaaaggac aauuacaaac aggaaucgaa ugcaaccggc gcaggaacac 11280
ugccagcgca ucaacaauau uuucaccuga aucaggauau ucuucuaaua ccuggaaugc 11340
uguuuucccg gggaucgcag uggugaguaa ccaugcauca ucaggaguac ggauaaaaug 11400
cuugaugguc ggaagaggca uaaauuccgu cagccaguuu agucugacca ucucaucugu 11460
aacaucauug gcaacgcuac cuuugccaug uuucagaaac aacucuggcg caucgggcuu 11520
cccauacaau cgauagauug ucgcaccuga uugcccgaca uuaucgcgag cccauuuaua 11580
cccauauaaa ucagcaucca uguuggaauu uaaucgcggc cucgagcaag acguuucccg 11640
uugaauaugg cucauaacac cccuuguauu acuguuuaug uaagcagaca guuuuauugu 11700
ucaugagcgg auacauauuu gaauguauuu agaaaaauaa acaaauaggg guuccgcgca 11760
cauuuccccg aaaagugcca ccuaaauugu aagcguuaau auuuuguuaa aauucgcguu 11820
aaauuuuugu uaaaucagcu cauuuuuuaa ccaauaggcc gaaaucggca aaaucccuua 11880
uaaaucaaaa gaauagaccg agauaggguu gaguggccgc uacagggcgc ucccauucgc 11940
cauucaggcu gcgcaacugu ugggaagggc guuucggugc gggccucuuc gcuauuacgc 12000
cagcuggcga aaggggggaug ugcugcaagg cgauuaaguu ggguaacgcc aggguuuucc 12060
cagucacacg cguaauacga cucacuauag 12090

<210> SEQ ID NO 38
<211> LENGTH: 12081
<212> TYPE: RNA
<213> ORGANISM: Artificial Sequence
<220> FEATURE:
<223> OTHER INFORMATION: SAM vector background with Zika antigen insert.

<400> SEQUENCE: 38
auaggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240

-continued

```
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu cgccgccguc augagcgacc    420
cugaccugga aacugagacu augugccucc acgacgacga gucgugucgc uacgaagggc    480
aagucgcugu uuaccaggau guauacgcgg uugacggacc gacaagucuc uaucaccaag    540
ccaauaaggg aguuagaguc gccuacugga uaggcuuuga caccaccccu uuuauguuua    600
agaacuuggc uggagcauau ccaucauacu cuaccaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgauggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
```

```
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugauag   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aagugguccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuucccg gguaugcaaa ccgaaauccu    3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggaggggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
```

-continued

```
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccaccccgc   5520
caggcgugaa uagggugauc acuagagagg agcucgaggc gcuuaccccg ucacgcacuc   5580
cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu aggugugggac gcagagcugu   6900
ugacgcugau ugaggcggcu uucggcgaaa uuucaucaau acauuugccc acuaaaacua   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
```

guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
gaugggcaag cgguccgccg gcucuaucau guggcuggcc ucucuggccg uggucaucgc 7620
augcgcagga gcaaccagga gaggcagcgc cuacuauaug uaccuggaca gaaaugaugc 7680
cggcgaggcc aucagcuuuc ccaccacacu gggcaugaac aaguguuaca uccagaucau 7740
ggaccugggc cacaugugcg augccaccau guccuaugag uguccaaugc uggacgaggg 7800
cguggagccc gacgaugugg auugcuggug uaauaccaca uccacauggg ugguguacgg 7860
caccugccac cacaagaagg gagaggcaag gcgcucucgg agagcaguga cacugccuuc 7920
ccacucuacc cggaagcugc agacaagauc ucagaccugg cuggagagcc gggaguauac 7980
aaagcaccug auccgggugg agaacuggau cuuuagaaau ccaggauucg cacuggcagc 8040
agcagcaauc gcauggcugc ugggcagcuc caccucccag aaagugaucu accuggucau 8100
gauccugcug aucgccccug ccuauuccau caggugcauc ggcgugucua aucgcgacuu 8160
cguggagggc augucuggcg gcaccugggu ggauguggug cuggagcacg gcggcugcgu 8220
gacagugaug gcccaggaca agccaaccgu ggacaucgag cuggugacca caaccgugag 8280
caacauggcc gaggugcggu ccuacugcua ugaggccagc aucuccgaca uggccucuga 8340
uagcagaugu cccacccagg gcgaggccua ccuggacaag cagucugaua cacaguacgu 8400
gugcaagagg acccuggugg acaggggaug gggaaaugga uguggccugu uuggcaaggg 8460
cagccuggug acaugcgcca aguucgccug uucuaagaag augaccggca agagcaucca 8520
gccagagaac cuggaguacc ggaucaugcu gagcgugcac ggcagccagc acuccggcau 8580
gaucgugaac gacacaggcc acgagacaga ugagaauagg gccaaggugg agaucacacc 8640
uaacagccca cgcgccgagg ccacccuggg aggauuuggc ucccugggcc uggacugcga 8700
gccuagaaca ggccuggacu ucuccgaucu guacuaucug accaugaaca auaagcacug 8760
gcuggugcac aaggaguggu uucacgacau cccacugcca uggcacgcag gagcagauac 8820
aggaacccca cacuggaaca auaaggaggc ccugguggag uucaaggaug cccacgccaa 8880
gaggcagaca guggugguggc ugggcagcca ggagggagca gugcacaccg cccuggcagg 8940
cgcccuggag gccgagaugg acggagcaaa gggccgccug ucuagcggcc accugaagug 9000
ccggcugaag auggauaagc ugagacugaa gggcgugucc uacucucugu gcacagccgc 9060
cuucaccuuc accaagaucc cugccgagac acugcacggc acagugaccg uggaggugca 9120
guaugccggc acagacggcc ccuguaaggu gccugcccag auggccgugg auaugcagac 9180
acugaccccu gugggcaggc ugaucaccgc caauccagug aucacagagu ccaccgagaa 9240
cucuaagaug augcuggagc uggacccccc uuuuggcgau agcuauaucg ugaucggcgu 9300
gggcgagaag aagaucacac accacuggca ccgcagcggc uccacaaucg gcaaggccuu 9360
ugaggccacc gugaggggag caaagaggau ggccgugcug ggcgacaccg caugggauuu 9420
cggcuccgug ggaggcgccc ugaacucucu gggcaagggc auccaccaga ucuucggcgc 9480
cgccuuuaag ucccuguucg gcggcauguc uugguuuagc cagauccuga ucggcacacu 9540
gcugaugugg cugggccuga acaccaagaa uggcucuauc agccugaugu gccuggcccu 9600
gggaggcgug cugaucuucc ugagcaccgc cguguccgcc ugaugauaag gcgcgcccac 9660
ccagcggccg cauacagcag caauuggcaa gcugcuuaca uagaacucgc ggcgauuggc 9720

-continued

```
augccgccuu aaaauuuuua uuuuauuuuu cuuuucuuuu ccgaaucgga uuuuguuuuu    9780
aauauuucaa aaaaaaaaaa aaaaaaaaaa aaaaaaaaaa aaaaaaaaga agagcguuua    9840
aacacgugau aucuggccuc augggccuuc cuuucacugc ccgcuuucca gucgggaaac    9900
cugucgugcc agcugcauua acauggucau agcuguuucc uugcguauug ggcgcucucc    9960
gcuuccucgc ucacugacuc gcugcgcucg gucguucggg uaaagccugg ggugccuaau   10020
gagcaaaagg ccagcaaaag gccaggaacc guaaaaaggc cgcguugcug gcguuuuucc   10080
auaggcuccg ccccccugac gagcaucaca aaaaucgacg cucaagucag agguggcgaa   10140
acccgacagg acuauaaaga uaccaggcgu uuccccccugg aagcucccuc gugcgcucuc  10200
cuguuccgac ccugccgcuu accggauacc uguccgccuu ucucccuucg ggaagcgugg   10260
cgcuuucuca uagcucacgc uguagguauc ucaguucggu guaggucguu cgcuccaagc   10320
ugggcugugu gcacgaaccc cccguucagc ccgaccgcug cgccuuaucc gguaacuauc   10380
gucuugaguc caacccggua agacacgacu uaucgccacu ggcagcagcc acugguaaca   10440
ggauuagcag agcgagguau guaggcggug cuacagaguu cuugaagugg uggccuaacu   10500
acggcuacac uagaagaaca guauuuggua ucugcgcucu gcugaagcca guuaccuucg   10560
gaaaaagagu ugguagcucu ugauccggca aacaaaccac cgcugguagc gguggauuuu   10620
uuguuugcaa gcagcagauu acgcgcagaa aaaaaggauc ucaagaagau ccuuugaucu   10680
uuucuacggg gucugacgcu caguggaacg aaaacucacg uuaagggauu uuggucauga   10740
auacacggug ccugacugcg uuagcaauuu aacugugaua aacuaccgca uuaaagcuua   10800
ucgaugauaa gcugucaaac augagaauuc uuagaaaaac ucaucgagca ucaaaugaaa   10860
cugcaauuua uucauaucag gauuaucaau accauauuuu ugaaaaagcc guuucuguaa   10920
ugaaggagaa aacucaccga ggcaguucca uaggauggca agauccuggu aucggucugc   10980
gauuccgacu cguccaacau caauacaacc uauuaauuuc cccucgucaa aaauaagguu   11040
aucaagugag aaaucaccau gagugacgac ugaauccggu gagaauggca aaagcuuaug   11100
cauuucuuuc cagacuuguu caacaggcca gccauuacgc ucgucaucaa aaucacucgc   11160
aucaaccaaa ccguuauuca uucgugauug cgccugagcg agacgaaaua cgcgaucgcu   11220
guuaaaagga caauuacaaa caggaaucga augcaaccgg cgcaggaaca cugccagcgc   11280
aucaacaaua uuuucaccug aaucaggaua uucuucuaau accuggaaug cuguuuuccc   11340
ggggaucgca guggugagua accaugcauc aucaggagua cggauaaaau gcuugauggu   11400
cggaagaggc auaaauuccg ucagccaguu uagucugacc aucucaucug uaacaucauu   11460
ggcaacgcua ccuuugccau guuucagaaa caacucuggc gcaucgggcu ucccauacaa   11520
ucgauagauu gucgcaccug auugcccgac auuaucgcga gcccauuuau acccauauaa   11580
aucagcaucc auguuggaau uuaaucgcgg ccucgagcaa gacguuuccc guugaauaug   11640
gcucauaaca ccccuuguau uacuguuuau guaagcagac aguuuuauug uucaugagcg   11700
gauacauauu ugaauguauu uagaaaaaua aacaaauagg gguuccgcgc acauuucccc   11760
gaaaagugcc accuaaauug uaagcguuaa uauuuuguua aaauucgcgu uaaauuuuug   11820
uuaaaucagc ucauuuuuua accaauaggc cgaaaucggc aaaaucccuu auaaaucaaa   11880
agaauagacc gagauagggu ugaguggccg cuacagggcg cucccauucg ccauucaggc   11940
ugcgcaacug uugggaaggg cguuucggug cgggccucuu cgcuauuacg ccagcuggcg   12000
aaagggggau gugcugcaag gcgauuaagu uggguaacgc caggguuuuc ccagucacac   12060
gcguaauacg acucacuaua g                                             12081
```

<210> SEQ ID NO 39
<211> LENGTH: 2091
<212> TYPE: RNA
<213> ORGANISM: Artificial Sequence
<220> FEATURE:
<223> OTHER INFORMATION: recombinant Zika virus antigen construct

<400> SEQUENCE: 39
augggcaagc gguccgccgg cucuaucaug uggcuggccu cucuggccgu ggucaucgca 60
ugcgcaggag cagcggaggu caccaggaga ggcagcgccu acuauaugua ccuggacaga 120
aaugaugccg gcgaggccau cagcuuuccc accacacugg gcaugaacaa guguuacauc 180
cagaucaugg accugggcca caugugcgau gccaccaugu ccuaugagug uccaaugcug 240
gacgagggcg uggagcccga cgauguggau ugcuggugua auaccacauc cacaugggug 300
guguacggca ccugccacca caagaaggga gaggcaaggc gcucucggag agcagugaca 360
cugccuuccc acucuacccg gaagcugcag acaagaucuc agaccuggcu ggagagccgg 420
gaguauacaa agcaccugau ccggguggag aacuggaucu uuagaaaucc aggauucgca 480
cuggcagcag cagcaaucgc auggcugcug ggcagcucca ccucccagaa agugaucuac 540
cuggucauga uccugcugau cgccccugcc uauuccauca ggugcaucgg cgugucuaau 600
cgcgacuucg uggagggcau gucuggcggc accugggugg augguggcu ggagcacggc 660 ggcugcguga cagugauggc ccaggacaag ccaaccgugg acaucgagcu ggugaccaca 720
accgugagca acauggccga ggugcggucc uacugcuaug aggccagcau cuccgacaug 780
gccucugaua gcagaugucc cacccagggc gaggccuacc uggacaagca gucugauaca 840
caguacgugu gcaagaggac ccugguggac aggggauggg gaaauggaug uggccuguuu 900
ggcaagggca gccuggugac augcgccaag uucgccuguu cuaagaagau gaccggcaag 960
agcauccagc cagagaaccu ggaguaccgg aucaugcuga gcgugcacgg cagccagcac 1020
uccggcauga ucgugaacga cacaggccac gagacagaug agaauagggc caagguggag 1080
aucacaccua acagcccacg cgccgaggcc acccugggag gauuuggcuc ccugggccug 1140
gacugcgagc cuagaacagg ccuggacuuc uccgaucugu acuaucugac caugaacaau 1200
aagcacuggc uggugcacaa ggaguggguuu cacgacaucc cacugccaug gcacgcagga 1260
gcagauacag gaaccccaca cuggaacaau aaggaggccc ugguggaguu caaggaugcc 1320
cacgccaaga ggcagacagu gguggugcug ggcagccagg agggagcagu gcacaccgcc 1380
cuggcaggcg cccuggaggc cgagauggac ggagcaaagg gccgccuguc uagcggccac 1440
cugaagugcc ggcugaagau ggauaagcug agacugaagg gcguguccua cucucugugc 1500
acagccgccu ucaccuucac caagaucccu gccgagacac ugcacggcac agugaccgug 1560
gaggugcagu augccggcac agacggcccc uguaaggugc cugcccagau ggccguggau 1620
augcagacac ugaccccugu gggcaggcug aucaccgcca auccagugau cacagagucc 1680
accgagaacu cuaagaugau gcuggagcug gacccccuu uuggcgauag cuauaucgug 1740
aucggcgugg gcgagaagaa gaucacacac cacuggcacc gcagcggcuc cacaaucggc 1800
aaggccuuug aggccaccgu gaggggagca aagaggaugg ccgugcuggg cgacaccgca 1860
ugggauuucg gcuccguggg aggcgcccug aacucucugg gcaagggcau ccaccagauc 1920
uucggcgccg ccuuuaaguc ccuguucggc ggcaugucuu gguuuagcca gauccugauc 1980
ggcacacugc ugauguggcu gggccugaac accaagaaug gcucuaucag ccugaugugc 2040
cuggcccugg gaggcgugcu gaucuuccug agcaccgccg uguccgccug a 2091

<210> SEQ ID NO 40
<211> LENGTH: 2091
<212> TYPE: RNA
<213> ORGANISM: Artificial Sequence
<220> FEATURE:
<223> OTHER INFORMATION: recombinant Zika virus antigen construct

<400> SEQUENCE: 40
augggcaagc gguccgccgg cucuaucaug uggcuggccu cucuggccgu ggucaucgca 60
ugcgcaggag cagcggaggu caccaggaga ggcagcgccu acuauaugua ccuggacaga 120
aaugaugccg gcgaggccau cagcuuuccc accacacugg gcaugaacaa guguuacauc 180
cagaucaugg accugggcca caugugcgau gccaccaugu ccuaugagug uccaaugcug 240
gacgagggcg uggagcccga cgauguggau ugcuggugua auaccacauc cacaugggug 300
guguacggca ccugccacca caagaaggga gaggcaaggc gcucucggag agcagugaca 360
cugccuuccc acucuacccg gaagcugcag acaagaucuc agaccuggcu ggagagccgg 420
gaguauacaa agcaccugau ccggguggag aacuggaucu uuagaaaucc aggauucgca 480
cuggcagcag cagcaaucgc auggcugcug ggcagcucca ccucccagaa agugaucuac 540
cuggucauga uccugcugau cgccccugcc uauuccauca ggugcaucgg cgugucuaau 600
cgcgacuucg uggagggcau gucuggcggc accugggugg auguggugcu ggagcacggc 660
ggcugcguga cagugauggc ccaggacaag ccaaccgugg acaucgagcu ggugaccaca 720
accgugagca acauggccga ggugcggucc uacugcuaug aggccagcau cuccgacaug 780
gccucugaua gcagaugucc cacccagggc gaggccuacc uggacaagca gucugauaca 840
caguacgugu gcaagaggac ccugguggac aggggauggg gaaauggaug uggccuguuu 900
ggcaagggca gccuggugac augcgccaag uucgccuguu cuaagaagau gaccggcaag 960
agcauccagc cagagaaccu ggaguaccgg aucaugcuga gcgugcacgg cagccagcac 1020
uccggcauga ucgugaacga cacaggccac gagacagaug agaauagggc caagguggag 1080
aucacaccua acagcccacg cgccgaggcc acccugggag gauuuggcuc ccugggccug 1140
gacugcgagc cuagaacagg ccuggacuuc uccgaucugu acuaucugac caugaacaau 1200
aagcacuggc uggugcacaa ggaguggguuu cacgacaucc cacugccaug gcacgcagga 1260
gcagauacag gaaccccaca cuggaacaau aaggaggccc ugguggaguu caaggaugcc 1320
cacgccaaga ggcagacagu gguggugcug ggcagccagg agggagcagu gcacaccgcc 1380
cuggcaggcg cccuggaggc cgagauggac ggagcaaagg gccgccuguc uagcggccac 1440
cugaagugcc ggcugaagau ggauaagcug agacugaagg gcguguccua cucucugugc 1500
acagccgccu ucaccuucac caagaucccu gccgagacac ugcacggcac agugaccgug 1560
gaggugcagu augccggcac agacggcccc uguaaggugc cugcccagau ggccguggau 1620
augcagacac ugaccccugu gggcaggcug aucaccgcca auccagugau cacagagucc 1680
accgagaacu cuaagaugau gcuggagcug gacccccuu uuggcgauag cuauaucgug 1740
aucggcgugg gcgagaagaa gaucacacac cacuggcacc gcagcggcuc cacccugggc 1800
aaggccuuua gcaccacccu gaagggagca cagaggcugg ccgcccuggg cgacaccgca 1860
ugggauuucg gcuccaucgg aggcguguuc aacucuaucg gcaaggccgu gcaccaggug 1920
uucggcggcg ccuuucggac ccuguucggc ggcaugucuu ggaucaccca gggccugaug 1980
ggcgcccugc ugcuguggau gggcgugaac gcccgggacc ggucuaucgc ccuggccuuc 2040
cuggccaccg gaggcgugcu gguguuccug gccaccaacg ugcacgccug a 2091

<210> SEQ ID NO 41
<211> LENGTH: 2082
<212> TYPE: RNA
<213> ORGANISM: Artificial Sequence
<220> FEATURE:
<223> OTHER INFORMATION: recombinant Zika virus antigen construct

<400> SEQUENCE: 41
augggcaagc gguccgccgg cucuaucaug uggcuggccu cucuggccgu ggucaucgca 60
ugcgcaggag caaccaggag aggcagcgcc uacuauaugu accuggacag aaaugaugcc 120
ggcgaggcca ucagcuuucc caccacacug ggcaugaaca aguguuacau ccagaucaug 180
gaccugggcc acaugugcga ugccaccaug uccuaugagu guccaaugcu ggacgagggc 240
guggagcccg acgaugugga uugcuggugu aauaccacau ccacaugggu gguguacggc 300
accugccacc acaagaaggg agaggcaagg cgcucucgga gagcagugac acugccuucc 360
cacucuaccc ggaagcugca gacaagaucu cagaccuggc uggagagccg ggaguauaca 420
aagcaccuga uccgggugga gaacuggauc uuuagaaauc caggauucgc acuggcagca 480
gcagcaaucg cauggcugcu gggcagcucc accucccaga aagugaucua ccuggucaug 540
auccugcuga ucgccccugc cuauuccauc aggugcaucg gcgugucuaa ucgcgacuuc 600
guggagggca ugucuggcgg caccugggug gauguggugc uggagcacgg cggcugcgug 660
acagugaugg cccaggacaa gccaaccgug gacaucgagc uggugaccac aaccgugagc 720
aacauggccg aggugcgguc cuacugcuau gaggccagca ucuccgacau ggccucugau 780
agcagauguc ccacccaggg cgaggccuac cuggacaagc agucugauac acaguacgug 840
ugcaagagga cccuggugga caggggaugg ggaaauggau guggccuguu uggcaagggc 900
agccugguga caugcgccaa guucgccugu ucuaagaaga ugaccggcaa gagcauccag 960
ccagagaacc uggaguaccg gaucaugcug agcgugcacg gcagccagca cuccggcaug 1020
aucgugaacg acacaggcca cgagacagau gagaauaggg ccaaggugga gaucacaccu 1080
aacagcccac gcgccgaggc cacccuggga ggauuuggcu cccugggccu ggacugcgag 1140
ccuagaacag gccuggacuu cuccgaucug uacuaucuga ccaugaacaa uaagcacugg 1200
cuggugcaca aggagugguu ucacgacauc ccacugccau ggcacgcagg agcagauaca 1260
ggaaccccac acuggaacaa uaaggaggcc cugguggagu ucaaggaugc ccacgccaag 1320
aggcagacag ugguggugcu gggcagccag gagggagcag ugcacaccgc ccuggcaggc 1380
gcccuggagg ccgagaugga cggagcaaag ggccgccugu cuagcggcca ccugaagugc 1440
cggcugaaga uggauaagcu gagacugaag ggcguguccu acucucugug cacagccgcc 1500
uucaccuuca ccaagauccc ugccgagaca cugcacggca cagugaccgu ggaggugcag 1560
uaugccggca cagacggccc cuguaaggug ccugcccaga uggccgugga uaugcagaca 1620
cugaccccug ugggcaggcu gaucaccgcc aauccaguga ucacagaguc caccgagaac 1680
ucuaagauga ugcuggagcu ggaccccccu uuuggcgaua gcuauaucgu gaucggcgug 1740
ggcgagaaga agaucacaca ccacuggcac cgcagcggcu ccacaaucgg caaggccuuu 1800
gaggccaccg ugaggggagc aaagaggaug gccgugcugg gcgacaccgc augggauuuc 1860
ggcuccgugg gaggcgcccu gaacucucug ggcaagggca uccaccagau cuucggcgcc 1920
gccuuuaagu cccuguucgg cggcaugucu ugguuuagcc agauccugau cggcacacug 1980

-continued

| | |
|---|---|
| cugauguggc ugggccugaa caccaagaau ggcucuauca gccugaugug ccuggcccug | 2040 |
| ggaggcgugc ugaucuuccu gagcaccgcc guguccgccu ga | 2082 |